United States Patent
Yabunouchi et al.

(10) Patent No.: US 9,139,522 B2
(45) Date of Patent: Sep. 22, 2015

(54) AROMATIC AMINE DERIVATIVE AND ORGANIC ELECTROLUMINESCENT DEVICE USING THE SAME

(75) Inventors: Nobuhiro Yabunouchi, Sodegaura (JP); Michiru Sekiguchi, Sodegaura (JP); Takahiko Ochi, Sodegaura (JP); Yoshiyuki Totani, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 602 days.

(21) Appl. No.: 13/124,759

(22) PCT Filed: Oct. 17, 2008

(86) PCT No.: PCT/JP2008/002957
§ 371 (c)(1),
(2), (4) Date: Apr. 18, 2011

(87) PCT Pub. No.: WO2010/044130
PCT Pub. Date: Apr. 22, 2010

(65) Prior Publication Data
US 2011/0198581 A1    Aug. 18, 2011

(51) Int. Cl.
| | |
|---|---|
| H01L 51/54 | (2006.01) |
| C07D 209/82 | (2006.01) |
| C07D 209/86 | (2006.01) |
| C07D 209/56 | (2006.01) |
| C09K 11/06 | (2006.01) |
| H05B 33/14 | (2006.01) |
| C09B 57/00 | (2006.01) |
| H01L 51/00 | (2006.01) |
| H01L 51/50 | (2006.01) |

(52) U.S. Cl.
CPC ............ *C07D 209/86* (2013.01); *C07D 209/56* (2013.01); *C09B 57/00* (2013.01); *C09B 57/008* (2013.01); *C09K 11/06* (2013.01); *H01L 51/0061* (2013.01); *H01L 51/0072* (2013.01); *H05B 33/14* (2013.01); *C09K 2211/1011* (2013.01); *C09K 2211/1029* (2013.01); *H01L 51/006* (2013.01); *H01L 51/5048* (2013.01)

(58) Field of Classification Search
CPC .... C07D 209/56; C07D 209/86; C09B 57/00; C09B 57/008; C09K 11/06; C09K 2211/1011; C09K 2211/1029; H01L 51/006; H01L 51/0061; H01L 51/0072; H01L 51/5048; H05B 33/14
See application file for complete search history.

(56) References Cited

U.S. PATENT DOCUMENTS

| | | | |
|---|---|---|---|
| 4,720,432 A | 1/1988 | VanSlyke et al. | |
| 5,061,569 A | 10/1991 | VanSlyke et al. | |
| 6,242,115 B1 | 6/2001 | Thomson et al. | |
| 2006/0159957 A1 | 7/2006 | Yabunouchi et al. | |
| 2007/0055085 A1 | 3/2007 | Kubota et al. | |
| 2007/0224449 A1 | 9/2007 | Kato et al. | |
| 2007/0296331 A1 | 12/2007 | Yabunouchi et al. | |
| 2008/0014464 A1 | 1/2008 | Kawamura et al. | |
| 2008/0091025 A1 | 4/2008 | Morishita et al. | |
| 2011/0315964 A1* | 12/2011 | Eida et al. ........................ | 257/40 |
| 2012/0091438 A1* | 4/2012 | Yabunouchi et al. ........... | 257/40 |
| 2012/0292606 A1* | 11/2012 | Kato ............................... | 257/40 |

FOREIGN PATENT DOCUMENTS

| | | |
|---|---|---|
| EP | 1 864 965 A1 | 12/2007 |
| JP | 11-144873 A | 5/1999 |
| JP | 11-273860 A | 10/1999 |

(Continued)

OTHER PUBLICATIONS

Translation for JP 2005-120030 (publication date: May 2005).*

(Continued)

*Primary Examiner* — Dawn Garrett
(74) *Attorney, Agent, or Firm* — Buchanan, Ingersoll & Rooney PC

(57) ABSTRACT

Disclosed is a long-life organic EL device having high luminous efficiency even after storage at high temperatures. Also disclosed is an aromatic amine derivative which enables to realize such an organic EL device. The aromatic amine derivative is represented by the following general formula (1).

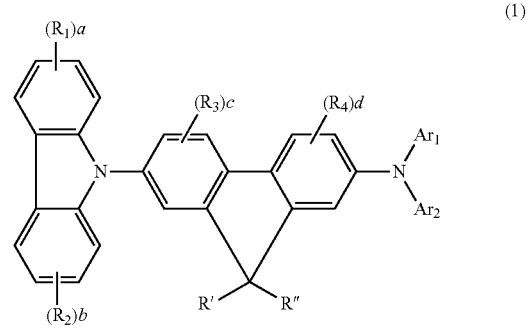

(In the formula (1), Ar1 is represented by the general formula (2) below, and Ar2 is represented by the general formula (3) below.)

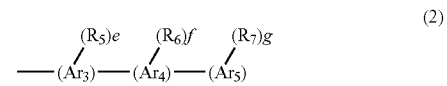

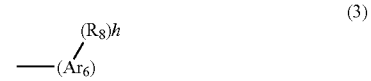

15 Claims, No Drawings

(56) References Cited

FOREIGN PATENT DOCUMENTS

| | | |
|---|---|---|
| JP | 2000-302756 A | 10/2000 |
| JP | 2004-103467 A | 4/2004 |
| JP | 2004-339064 A | 12/2004 |
| JP | 2004-345960 A | 12/2004 |
| JP | 2005-120030 A | 5/2005 |
| JP | 2007-246399 A | 9/2007 |
| JP | 2007-266046 A | 10/2007 |
| JP | 2007-284431 A | 11/2007 |
| JP | 2007-291061 A | 11/2007 |
| JP | 2008-069120 A | 3/2008 |
| JP | 2008-120769 A | 5/2008 |
| WO | WO 2005/054162 A1 | 6/2005 |
| WO | WO 2006/006505 A1 | 1/2006 |
| WO | WO 2006/112166 A1 | 10/2006 |
| WO | WO 2007/102361 A1 | 9/2007 |
| WO | WO 2007/105783 A1 | 9/2007 |
| WO | WO 2007/114038 A1 | 10/2007 |
| WO | WO 2007/148660 A1 | 12/2007 |
| WO | WO 2008/001551 A1 | 1/2008 |

OTHER PUBLICATIONS

International Search Report (PCT/ISA/210) issued on Dec. 16, 2008, by Japanese Patent Office as the International Searching Authority for International Application No. PCT/JP2008/002957.

* cited by examiner

AROMATIC AMINE DERIVATIVE AND ORGANIC ELECTROLUMINESCENT DEVICE USING THE SAME

TECHNICAL FIELD

The present invention relates to aromatic amine derivatives and organic electroluminescent (EL) devices using the same. More specifically, the present invention relates to aromatic amine derivatives that can improve the luminous efficiency and prolong the life of organic EL devices after high temperature storage.

BACKGROUND ART

Organic EL devices are a class of self-emission devices that make use of the principle of electroluminescence—when an electric field is applied, a fluorescent material emits light because of the energy released from the recombination of electrons and holes injected from the cathode and anode, respectively. C. W. Tang et al. of Eastman Kodak Company reported a low-voltage-driven organic EL device using a double layered structure (C. W. Tang, S. A. Vanslyke, Applied Physics Letters, Vol. 51, 913 (1987), etc.). Since then, extensive research has been undertaken on organic EL devices that utilize organic EL materials. Well-known device structures for organic EL devices include a double layer structure composed of a hole transport (injection) layer and an electron transport/emitting layer; and a triple layer structure composed of a hole transport (injection) layer, an emitting layer, and an electron transport (injection) layer. Aiming to increase the recombination efficiency of injected holes and electrons, various improvements have been made on the device structure and fabrication process of such stack-type organic EL devices.

Driving or storing organic EL devices under high temperature conditions generally leads to adverse consequences, including changes in emitted light color, reduced luminous efficiency, elevated driving voltage, and shorter emission lifetime. To avoid these drawbacks it has been required in the art to increase the glass transition temperatures (Tg) of hole transport materials, requiring molecules of hole transport materials to have many aromatic groups (see, e.g., aromatic diamine derivatives disclosed in Patent Literature 1 and aromatic condensed ring diamine derivatives disclosed in Patent Literature 2). Typically, hole transport materials that have 8 to 12 benzene rings per molecule are preferably used.

However, manufacturing of an organic EL device by forming a thin film of hole transport material that has many aromatic groups in its molecule has encountered problems, such as clogging of the opening of the vapor deposition crucible by the crystallized material, and reduction in manufacturing yield caused by defects in the deposited thin film due to crystallization. Compounds that have many aromatic groups in their molecules generally have high glass transition temperatures (Tg), but at the same time have high sublimation temperatures, which is considered to be responsible for the material decomposition during vapor evaporation, non-uniform thickness in the deposited films and other phenomena, leading to shorter device life.

Meanwhile, as hole transport materials, carbazole-containing monoamine derivatives are also known (see Patent Literatures 3 to 7). These compounds, however, cannot sufficiently prolong the life and improve the luminous efficiency of organic EL devices, especially after high temperature storage. Additionally, amine derivatives are known in which carbazole and amine are linked together with fluorene (see Patent Literatures 8 and 9), but the effects of prolonging life and improving luminous efficiency have likewise been needed for these compounds.

Although some hole transport materials for realizing long-life, high-efficient organic EL devices have been reported so far as described above, there is strong demand for device materials that can provide organic EL devices with more excellent performance.

CITATION LIST

Patent Literature

PTL 1: U.S. Pat. No. 4,720,432
PTL 2: U.S. Pat. No. 5,061,569
PTL 3: U.S. Pat. No. 6,242,115
PTL 4: Japanese Patent Application Laid-Open No. 2007-284431
PTL 5: Japanese Patent Application Laid-Open No. 2004-103467
PTL 6: Japanese Patent Application Laid-Open No. 2008-120769
PTL 7: Japanese Patent Application Laid-Open No. 11-273860
PTL 8: Japanese Patent Application Laid-Open No. 11-144873
PTL 9: Japanese Patent Application Laid-Open No. 2000-302756

SUMMARY OF INVENTION

Technical Problem

The present invention has been accomplished in order to overcome the foregoing problems pertinent in the art. An object of the present invention is therefore to provide organic EL devices that offer high luminous efficiency and long life even after high temperature storage, and aromatic amine derivatives for realizing such organic EL devices.

Solution to Problem

The inventors conducted extensive studies aiming to achieve the foregoing object, and established that the object can be achieved by employing a novel aromatic amine derivative with a specific structure, which is represented by general formula (1), as an organic EL device material, especially as a hole transport material. The inventors thus completed the present invention.

First, the inventors attributed the life-prolonging effect to the stability of amine derivatives, which have carbazole bonded to the amino group via fluorene, against both oxidization and reduction. In search of amino group structures that provide higher stability against reduction, the inventors then conducted various studies and as a consequence found that an appropriately sterically hindered amino group reduces the interaction among molecules and thus suppresses crystallization, as well as is effective in increasing Tg.

The inventors also found that the asymmetric structure of the compound of the present invention enables to lower its vapor deposition temperature and therefore to suppress material decomposition during vapor deposition, and further that the compounds' high packing ability, interactions with the emitting layer or other factors bring about the effects of prolonging the life and enhancing the luminous efficiency of resulting an organic EL device, particularly when the compounds is used in a blue light-emitting device. The inventors thus completed the present invention.

Specifically, a first aspect of the present invention provides an aromatic amine derivative represented by general formula (1):

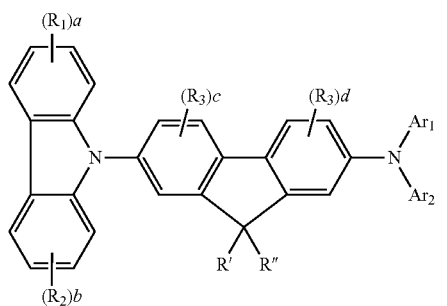

(1)

A second aspect of the present invention provides an organic electroluminescent device which includes a cathode, an anode, and one or more organic thin layers interposed between the anode and cathode, the organic thin layers including at least an emitting layer, wherein at least one of the organic thin layers contains the aromatic amine derivative either alone or as a component of a mixture.

Advantageous Effects of Invention

An organic EL device manufactured using an aromatic amine derivative of the present invention offers high luminous efficiency and long life even after high temperature storage.

DESCRIPTION OF EMBODIMENTS

An aromatic amine derivative of the present invention is represented by general formula (1):

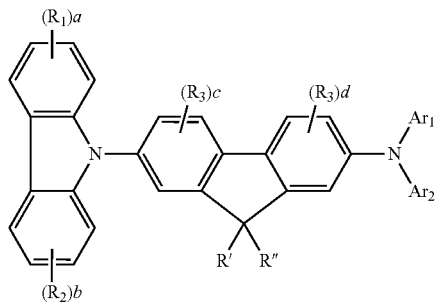

(1)

where $R_1$ to $R_4$ represent a straight or branched $C_{1-10}$ alkyl group, $C_{3-10}$ cycloalkyl group, $C_{1-10}$ alkoxy group, $C_{3-10}$ trialkylsilyl group, $C_{18-30}$ triarylsilyl group, $C_{8-15}$ alkylarylsilyl group, or aryl group having 6 to 14 nuclear carbon atoms;

a and b each independently represent an integer of 0 to 4;

c and d each independently represent an integer of 0 to 3;

adjacent groups of $R_1(s)$, $R_2(s)$, $R_3(s)$ and $R_4(s)$ may be joined together to form a saturated or unsaturated ring, provided that $R_3$ and $R_4$ do not join together to form an aromatic ring;

R' and R" represent a straight or branched $C_{1-12}$ alkyl group or $C_{3-10}$ cycloalkyl group;

$Ar_1$ is represented by the following general formula (2); and $Ar_2$ is represented by the following general formula (3).

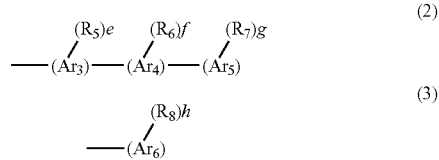

In general formulas (2) and (3), $Ar_3$ to $Ar_6$ each independently represent an arylene group having 6 to 14 nuclear carbon atoms;

$R_5$ to $R_8$ represent a hydrogen atom, straight, branched or cyclic $C_{1-10}$ alkyl group, $C_{1-10}$ alkoxy group, $C_{3-10}$ trialkylsilyl group, $C_{18-30}$ triarylsilyl group, $C_{8-15}$ alkylarylsilyl group, aryl group having 6 to 14 nuclear carbon atoms, or biphenyl group;

e and f each independently represent an integer of 1 to 4;

g and h each independently represent an integer of 1 to 5;

when e, f, g or h represents an integer of 2 or larger, $R_5$s, $R_6$s, $R_7$s or $R_8$s may be the same or different;

adjacent groups of $R_5(s)$, $R_6(s)$, $R_7(s)$ and $R_8(s)$ may be joined together to form a saturated ring, provided that $R_8$ is not an aryl having 6 nuclear carbon atoms; and $Ar_5$ may or may not be present in general formula (2), but where not present, $Ar_4$ is not an arylene group having 6 nuclear carbon atoms.

In the aromatic amine derivative represented by general formula (1), $R_1$ to $R_4$ represent a straight or branched $C_{1-10}$ alkyl group, $C_{3-10}$ cycloalkyl group, $C_{1-10}$ alkoxy group, $C_{3-10}$ trialkylsilyl group, $C_{18-30}$ triarylsilyl group, $C_{8-15}$ alkylarylsilyl group, or aryl group having 6 to 14 nuclear carbon atoms.

$R_1$ to $R_4$ preferably represent a straight or branched $C_{1-6}$ alkyl group, $C_{5-7}$ cycloalkyl group, $C_{1-6}$ alkoxy group, $C_{3-6}$ trialkylsilyl group, $C_{18-21}$ triarylsilyl group, $C_{8-12}$ alkylarylsilyl group, or aryl group having 6 to 10 nuclear carbon atoms; more preferably a straight or branched $C_{1-6}$ alkyl group, $C_{5-7}$ cycloalkyl group, or aryl group having 6 to 10 nuclear carbon atoms.

Specific examples of straight or branched $C_{1-10}$ alkyl groups for $R_1$ to $R_4$ include methyl group, ethyl group, propyl group, isopropyl group, n-butyl group, s-butyl group, isobutyl group, t-butyl group, n-pentyl group, n-hexyl group, n-heptyl group, n-octyl group, 1-methylpentyl group, 4-methyl-2-pentyl group, 2-ethylbutyl group, n-heptyl group, 1-methylhexyl group, n-octyl group, 1-methylheptyl group, 2-ethylhexyl group, 2-propylpentyl group, n-nonyl group, 2,2-dimethylheptyl group, 2,6-dimethyl-4-heptyl group, 3,5,5-trimethylhexyl group, and n-decyl group. Among them, methyl group, ethyl group, propyl group, isopropyl group, n-butyl group, s-butyl group, isobutyl group, and t-butyl group are preferable.

Specific examples of $C_{3-10}$ cycloalkyl groups for $R_1$ to $R_4$ include cyclopropyl group, cycloheptyl group, cyclopentyl group, cyclohexyl group, cycloheptyl group, 4-methylcyclohexyl group, 1-adamantyl group, 2-adamantyl group, 1-norbornyl group, 2-norbornyl group, and bicycloocta[2.2.2]octyl group. Among them, cyclopentyl group, cyclohexyl group, and cycloheptyl group are preferable.

Specific examples of $C_{1-10}$ alkoxy groups for $R_1$ to $R_4$ include methoxy group, ethoxy group, n-propoxy group, isopropoxy group, n-propoxy group, s-butoxy group, t-butoxy group, n-pentoxy group, n-hexyloxy group, and n-octyloxy group. Among them, methoxy group, ethoxy group, n-propoxy group, isopropoxy group, n-butoxy group, s-butoxy group, and t-butoxy group are preferable.

Specific examples of $C_{3-10}$ trialkylsilyl groups for $R_1$ to $R_4$ include trimethylsilyl group, triethylsilyl group, tripropylsilyl group, and t-butyl-dimethylsilyl group. Among them, trimethylsilyl group and triethylsilyl group are preferable.

Specific examples of $C_{18-30}$ triarylsilyl groups for $R_1$ and $R_4$ include triphenylsilyl group, tris(4-methylphenyl)silyl group, tris(3-methylphenyl)silyl group, tris(2-methylphenyl)silyl group, and trinaphthylsilyl group. Among them, triphenylsilyl group and tris(4-methylphenyl)silyl group are preferable.

Specific examples of $C_{8-15}$ alkylarylsilyl groups for $R_1$ to $R_4$ include dimethylphenylsilyl group, diphenylmethylsilyl group, and dimethyl(4-methylphenyl)silyl group.

Specific examples of aryl groups having 6 to 14 nuclear carbon atoms for $R_1$ to $R_4$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 4-methylphenyl group, 3-methylphenyl group, 2-methylphenyl group, 4-ethylphenyl group, 3-ethylphenyl group, 2-ethylphenyl group, 4-n-propylphenyl group, 4-isopropylphenyl group, 2-isopropylphenyl group, 4-n-butylphenyl group, 4-isobutylphenyl group, 4-s-butylphenyl group, 2-s-butylphenyl group, 4-t-butylphenyl group, 3-t-butylphenyl group, 2-t-butylphenyl group, 4-n-pentylphenyl group, 4-isopentylphenyl group, 4-t-pentylphenyl group, 4-n-hexylphenyl group, 4-n-heptylphenyl group, 4-n-octylphenyl group, 4-(2'-ethylhexyl)phenyl group, 4-t-octylphenyl group, 4-cyclopentylphenyl group, 4-cyclohexylphenyl group, 4-(4'-methylcyclohexyl)phenyl group, 3-cyclohexylphenyl group, 2-cyclohexylphenyl group;

4-ethyl-1-naphthyl group, 6-n-butyl-2-naphthyl group;

2,3-dimethylphenyl group, 2,4-dimethylphenyl group, 2,5-dimethylphenyl group, 3,4-dimethylphenyl group, 3,5-dimethylphenyl group, 2,6-dimethylphenyl group, 2,3,5-trimethylphenyl group, 3,4,5-trimethylphenyl group, 2,4-diethylphenyl group, 2,4,6-trimethylphenyl group, 2,6-diethylphenyl group, 2,6-diisopropylphenyl group, 2,6-diisobutylphenyl group, 2,4-di-t-butylphenyl group, 2,5-di-t-butylphenyl group, 3,5-di-t-butylphenyl group, 2,4-dineopentylphenyl group, 2,2,3,5,6-tetramethylphenyl group;

4-methoxyphenyl group, 3-methoxyphenyl group, 2-methoxyphenyl group, 4-ethoxyphenyl group, 2-ethoxyphenyl group, 3-n-propoxyphenyl group, 4-isopropoxyphenyl group, 2-isopropoxyphenyl group, 4-n-butoxyphenyl group, 4-isobutoxyphenyl group, 2-isobutoxyphenyl group, 2-s-butoxyphenyl group, 4-n-pentyloxyphenyl group, 4-isopentyloxyphenyl group, 2-isopentyloxyphenyl group, 2-neopentyloxyphenyl group, 4-n-hexyloxyphenyl group, 2-(2'-ethylbutyl)oxyphenyl group, 4-n-octyloxyphenyl group, 4-cyclohexyloxyphenyl group, 2-cyclohexyloxyphenyl group, 2-methoxy-1-naphthyl group, 4-methoxy-1-naphthyl group, 4-n-butoxy-1-naphthyl group, 5-ethoxy-1-naphthyl group, 6-ethoxy-2-naphthyl group, 6-n-butoxy-2-naphthyl group, 7-methoxy-2-naphthyl group, 7-n-butoxy-2-naphthyl group;

2,3-dimethoxyphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 3,5-di-n-butoxyphenyl group, 3,5-diethoxyphenyl group, 2-methoxy-4-methylphenyl group, 2-methoxy-5-methylphenyl group, 2-methyl-4-methoxyphenyl group, 3-methyl-4-methoxyphenyl group, 3-methyl-5-methoxyphenyl group, 3-ethyl-5-methoxyphenyl group, 2-methoxy-4-ethoxyphenyl group, 2-methoxy-6-ethoxyphenyl group, 3,4,5-trimethoxyphenyl group;

4-fluorophenyl group, 3-fluorophenyl group, 2-fluorophenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 3,4,5-trifluorophenyl group;

2-fluoro-4-methylphenyl group, 2-fluoro-5-methylphenyl group, 3-fluoro-2-methylphenyl group, 3-fluoro-4-methylphenyl group, 4-fluoro-2-methylphenyl group, 5-fluoro-2-methylphenyl group, 2-chloro-4-methylphenyl group, 2-chloro-5-methylphenyl group, 2-chloro-6-methylphenyl group, 3-chloro-2-methylphenyl group, 4-chloro-2-methylphenyl group, 4-chloro-3-methylphenyl group, 2-chloro-4,6-dimethylphenyl group, 2-fluoro-4-methoxyphenyl group, 2-fluoro-6-methoxyphenyl group, 3-fluoro-4-ethoxyphenyl group;

4-trifluoromethylphenyl group, 3-trifluoromethylphenyl group, 2-trifluoromethylphenyl group, 3,5-bis(trifluoromethyl)phenyl group;

4-trifluoromethyloxyphenyl group;

p-(2-phenylpropyl)phenyl group, 3-methyl-2-naphthyl group, and 4-methyl-1-naphthyl group.

Among them, substituted or unsubstituted phenyl groups and naphthyl groups are preferable.

Symbols a and b each independently represent an integer of 0 to 4, preferably 0, Symbols c and d each independently represent an integer of 0 to 3, preferably 0.

In an aromatic amine derivative represented by general formula (1), adjacent groups of $R_1(s)$, $R_2(s)$, $R_3(s)$ and $R_4(s)$ may be joined together to form a saturated or unsaturated ring, provided that $R_3$ and $R_4$ do not join together to form an aromatic ring. The following shows specific examples in which adjacent groups of $R_1(s)$, $R_2(s)$, $R_3(s)$ and $R_4(s)$ are joined together to a saturated or unsaturated ring.

(Specific Examples of Saturated or Unsaturated Rings Attached to the Carbazole)

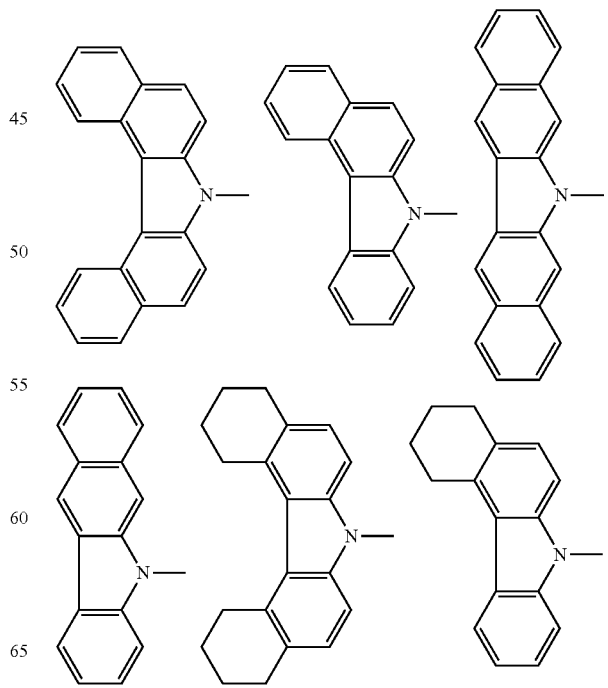

-continued
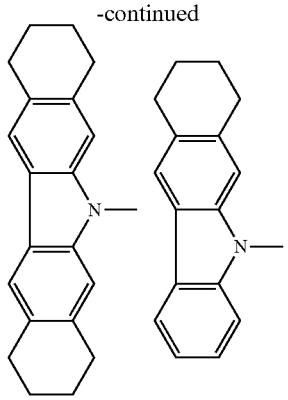
(Specific Examples of Saturated or Unsaturated Rings Attached to the Fluorene)
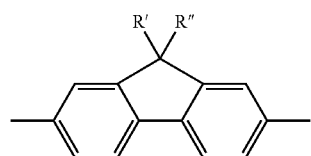
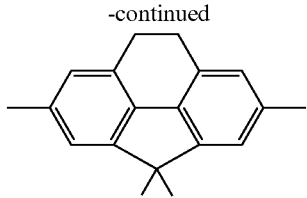
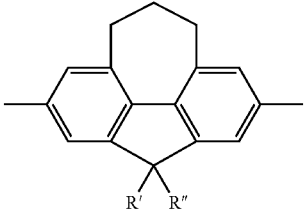
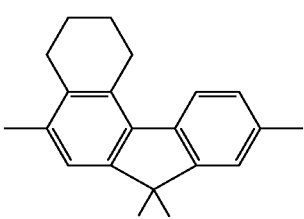
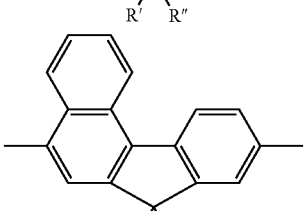
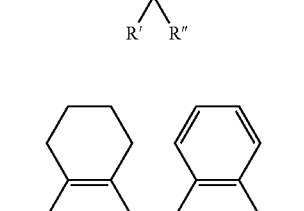
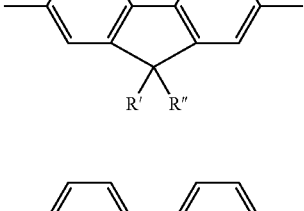
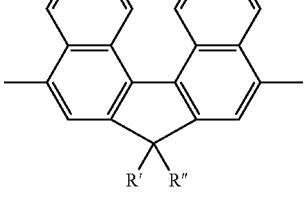
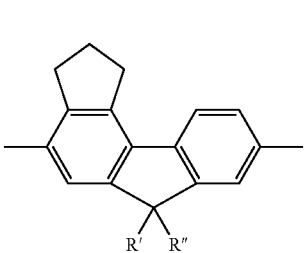

-continued

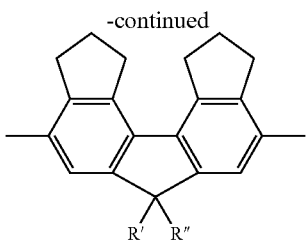

R' and R" represent a straight or branched $C_{1-12}$ alkyl group or $C_{3-10}$ cycloalkyl group, preferably a straight or branched $C_{1-6}$ alkyl group or $C_{5-7}$ cycloalkyl group.

For specific examples of straight or branched $C_{1-12}$ alkyl groups, the straight and branched alkyl groups cited as specific examples of straight or branched alkyl groups for $R_1$ to $R_4$ above can be cited.

For specific examples of $C_{3-10}$ cycloalkyl groups, the cycloalkyl groups cited as specific examples of cycloalkyl groups for $R_1$ to $R_4$ above can be cited.

In an aromatic amine derivative of the present invention represented by general formula (1), $Ar_1$ is represented by the following general formula (2), and $Ar_2$ is represented by the following general formula (3):

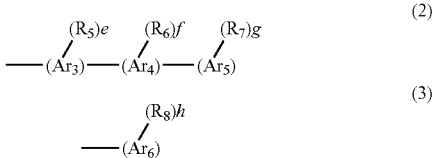

In general formulas (2) and (3), $Ar_3$ to $Ar_6$ each independently represent an arylene group having 6 to 14 nuclear carbon atoms;

$R_5$ to $R_8$ represent a hydrogen atom, straight, branched or cyclic $C_{1-10}$ alkyl group, $C_{1-10}$ alkoxy group, $C_{3-10}$ trialkylsilyl group, $C_{18-30}$ triarylsilyl group, $C_{8-15}$ alkylarylsilyl group, aryl group having 6 to 14 nuclear carbon atoms, or biphenyl group;

e and f each independently represent an integer of 1 to 4; g and h each independently represent an integer of 1 to 5; when e, f, g or h represents an integer of 2 or larger, $R_5$s, $R_6$s, $R_7$s or $R_8$s may be the same or different; adjacent groups of $R_5$(s), $R_6$(s), $R_7$(s) and $R_8$(s) may be joined together to form a saturated ring, provided that $R_8$ is not an aryl group having 6 nuclear carbon atoms; and $Ar_5$ may or may not be present in general formula (2), but where not present, $Ar_4$ is not an arylene group having 6 nuclear carbon atoms.

In general formulas (2) and (3), $Ar_3$ to $Ar_6$ each independently represent an arylene group having 6 to 14 nuclear carbon atoms, preferably an arylene group having 6 to 10 nuclear carbon atoms.

Specific examples $Ar_3$ to $Ar_6$ include residual divalent groups of benzene, naphthalene, anthracene, phenanthrene, toluene, p-t-butylbenzene, p-(2-phenylpropyl)benzene, 3-methylnaphthalene, and 4-methylnaphthalene. Preferably, $Ar_3$ to $Ar_6$ represent a residual divalent group of benzene or naphthalene.

In general formula (2), $Ar_5$ may or may not be present, but where not present, $Ar_4$ is not an arylene group having 6 nuclear carbon atoms.

In general formulas (2) and (3), $R_5$ to $R_8$ represent a hydrogen atom, straight, branched or cyclic $C_{1-10}$ alkyl group, $C_{1-10}$ alkoxy group, $C_{3-10}$ trialkylsilyl group, $C_{18-30}$ triarylsilyl group, $C_{8-15}$ alkylarylsilyl group, aryl group having 6 to 14 nuclear carbon atoms, or biphenyl group.

For specific examples of straight, branched or cyclic $C_{1-10}$ alkyl groups for $R_5$ to $R_8$, the straight and branched alkyl groups and cycloalkyl groups cited as specific examples of straight or branched $C_{1-10}$ alkyl groups or $C_{3-10}$ cycloalkyl groups for $R_1$ to $R_4$ in general formula (1) above can be cited.

For specific examples of $C_{1-10}$ alkoxy groups for $R_5$ to $R_8$, the alkoxy groups cited as specific examples of $C_{1-10}$ alkoxy groups for $R_1$ to $R_4$ in general formula (1) above can be cited.

For specific examples of $C_{3-10}$ trialkylsilyl groups for $R_5$ to $R_8$, the trialkylsilyl groups cited as specific examples of $C_{3-10}$ trialkylsilyl groups for $R_1$ to $R_4$ in general formula (1) above can be cited.

For specific examples of $C_{18-30}$ triarylsilyl groups for $R_5$ to $R_8$, the triarylsilyl groups cited as specific examples of $C_{18-30}$ triarylsilyl groups for $R_1$ to $R_4$ in general formula (1) above can be cited.

For specific examples of $C_{8-15}$ alkylarylsilyl groups for $R_5$ to $R_8$, the alkylarylsilyl groups cited as specific examples of $C_{8-15}$ alkylarylsilyl groups for $R_1$ to $R_4$ in general formula (1) above can be cited.

For specific examples of aryls having 6 to 14 nuclear carbon atoms for $R_5$ to $R_8$ the aryl groups cited as specific examples of aryl groups having 6 to 14 nuclear carbon atoms for $R_1$ to $R_4$ in general formula (1) above can be cited.

In general formula (2), $R_5$ to $R_7$ preferably represent a hydrogen atom, straight, branched or cyclic $C_{1-6}$ alkyl group, $C_{1-6}$ alkoxy group, $C_{3-6}$ trialkylsilyl group or aryl group having 6 to 14 nuclear carbon atoms; more preferably a hydrogen atom, straight, branched or cyclic $C_{1-4}$ alkyl group or aryl group having 6 to 10 nuclear carbon atoms. Yet preferably, $R_5$ and $R_6$ represent a hydrogen atom, and $R_7$ represents a hydrogen atom or aryl group having 6 to 10 nuclear carbon atoms.

In general formula (3), $R_8$ preferably represents a hydrogen atom, straight, branched or cyclic $C_{1-6}$ alkyl group, $C_{1-6}$ alkoxy group, $C_{3-6}$ trialkylsilyl group, aryl group having 10 to 14 nuclear carbon atoms or biphenyl group; more preferably a hydrogen atom, aryl group having 10 nuclear carbon atoms or biphenyl group. Note that $R_8$ is not an aryl group having 6 nuclear carbon atoms.

In general formulas (2) and (3), e and f each independently represent an integer of 1 to 4, and g and h each independently represent an integer of 1 to 5.

When e, f, g or h represents an integer of 2 or larger, $R_5$s, $R_6$s, $R_7$s or $R_8$s may be the same or different, and adjacent groups of $R_5$(s), $R_6$(s), $R_7$(s) and $R_8$(s) may be joined together to form a saturated ring. Specific examples of moieties in which adjacent groups of $R_5$(s), $R_6$(s), $R_7$(s) and $R_8$(s) are joined together to form a saturated ring are as follows:

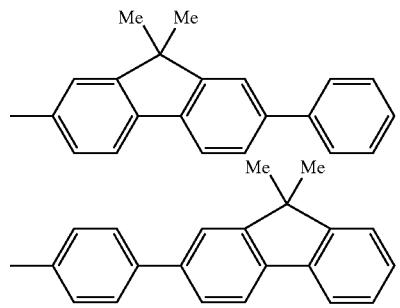

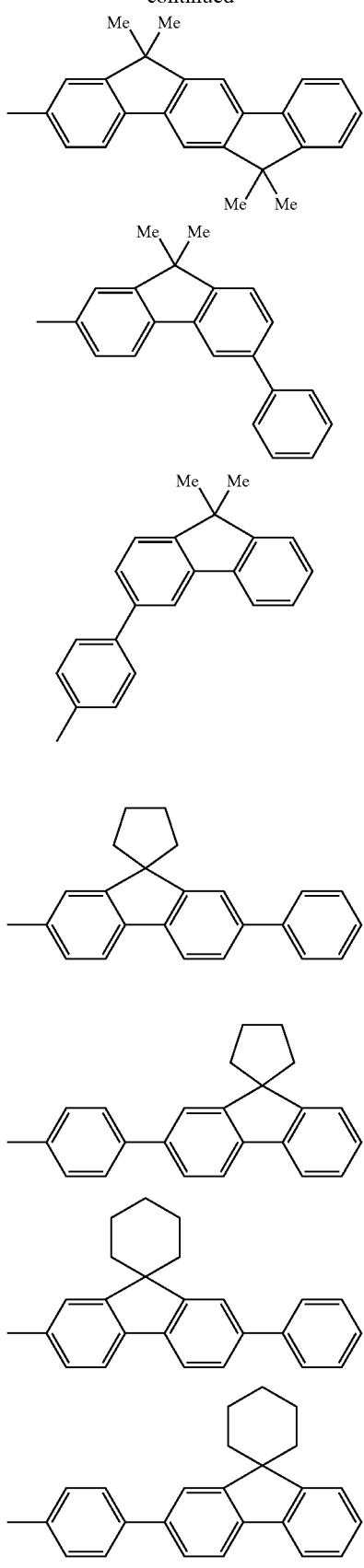

-continued
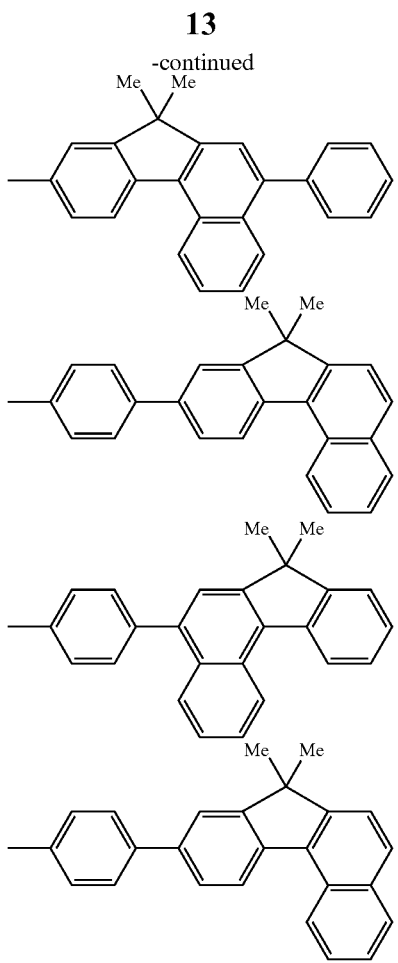
(Specific Examples of Saturated Rings)
For specific examples of moieties represented by general formula (2), those listed in the following Groups 1 to 6 can be cited.
(2) Group 1:
-continued
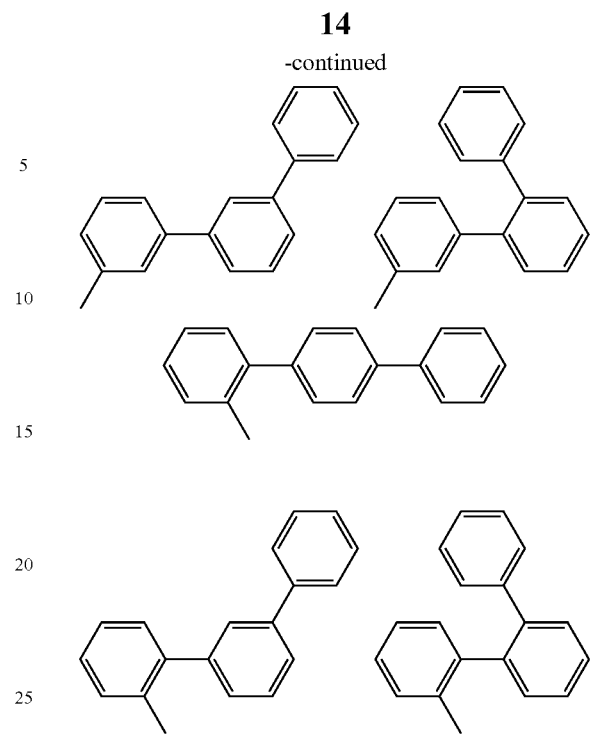
(2) Group 2:
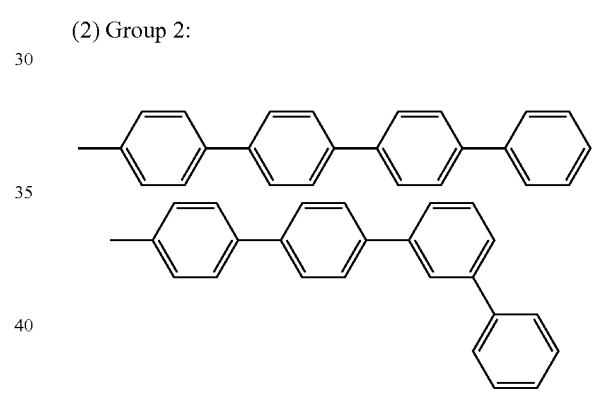
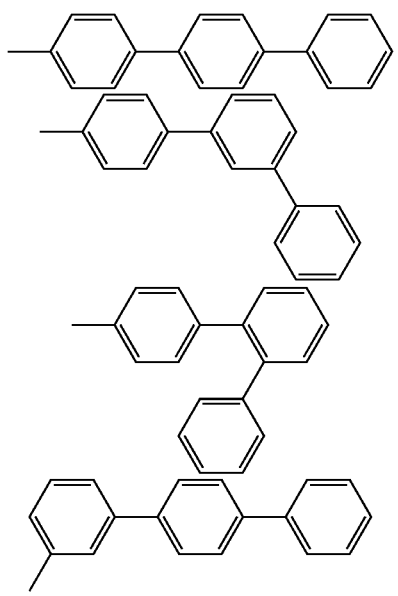
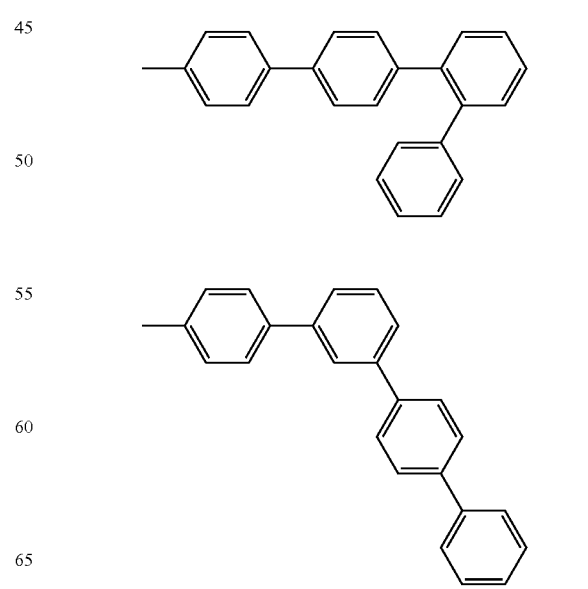

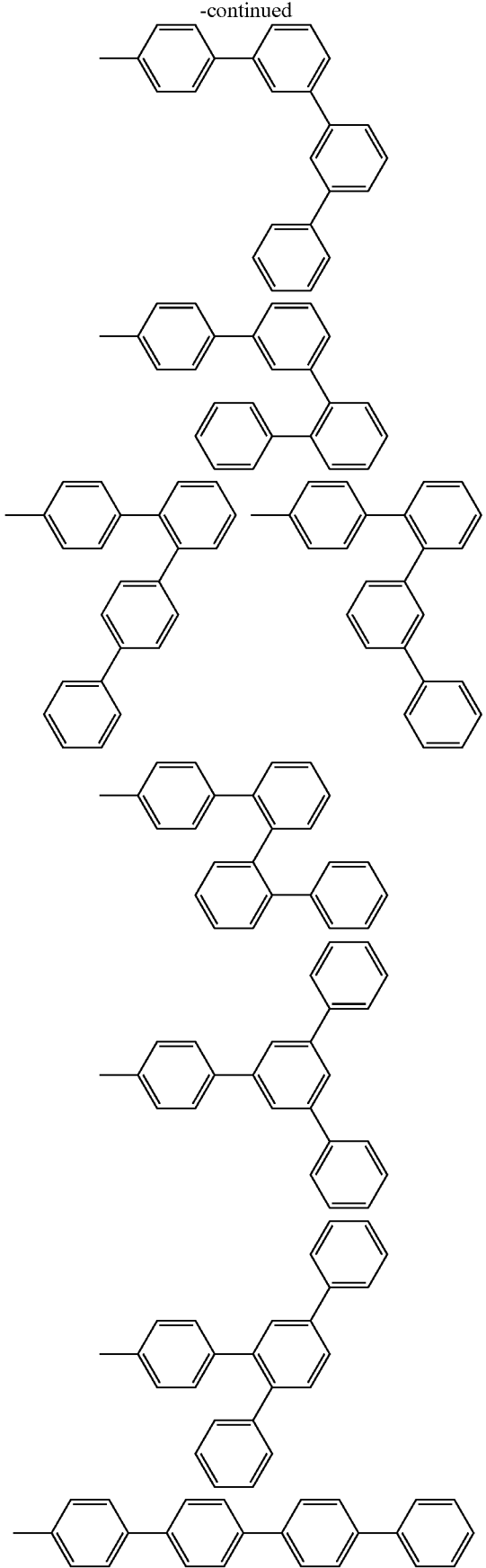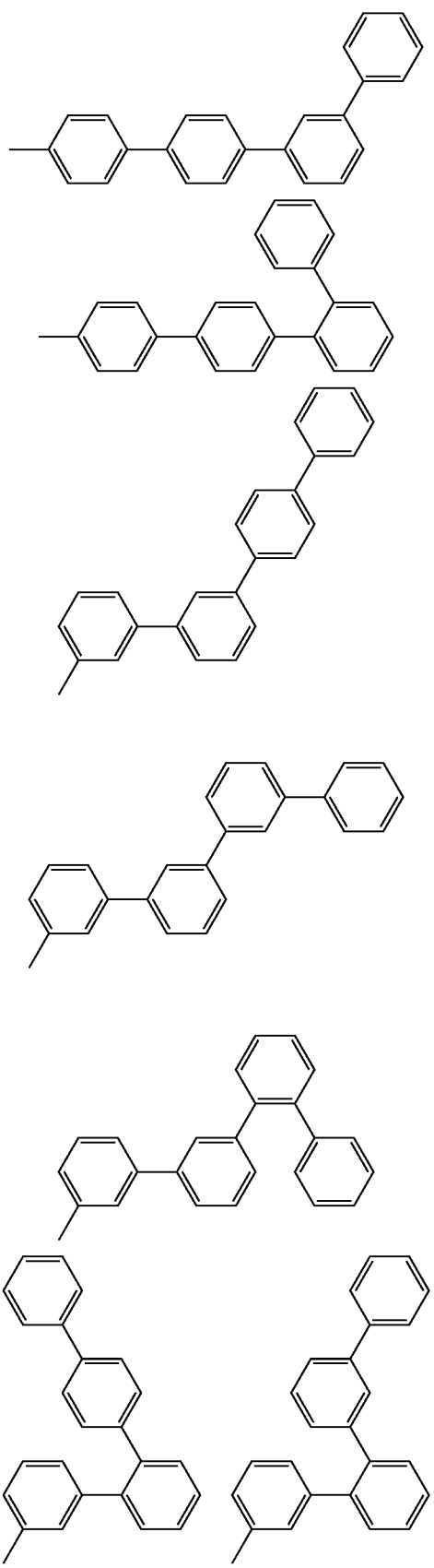

-continued
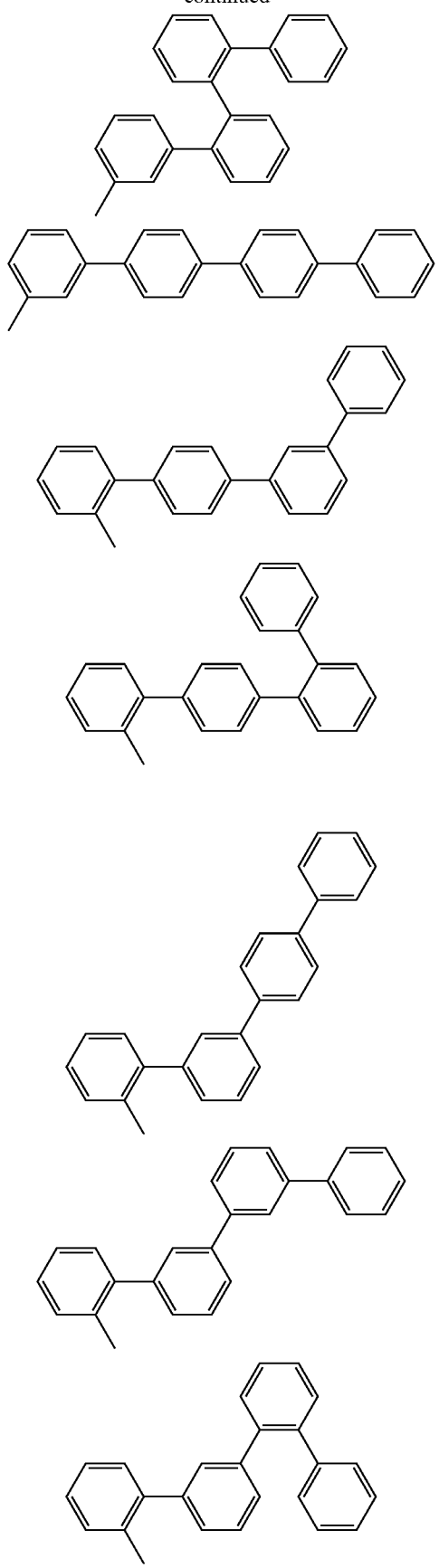
-continued
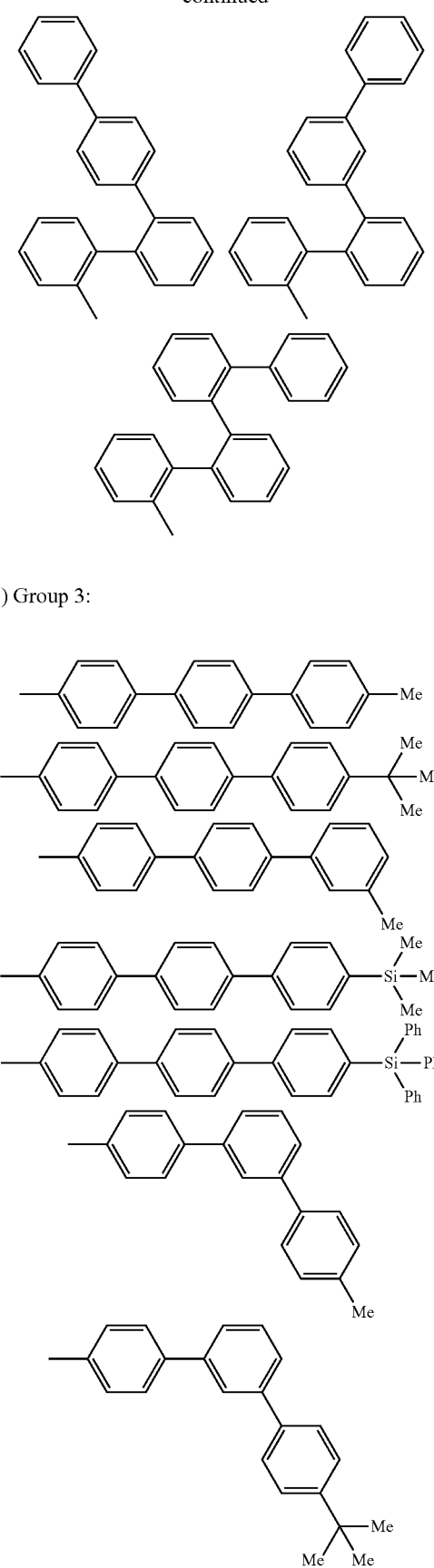
(2) Group 3:

-continued
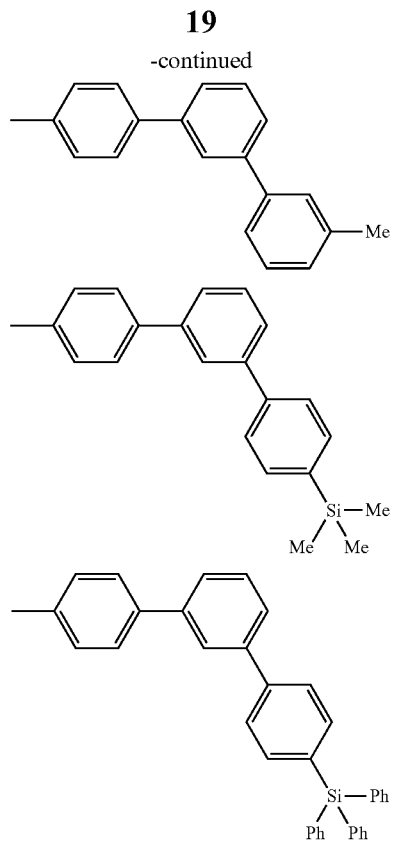
(2) Group 4:
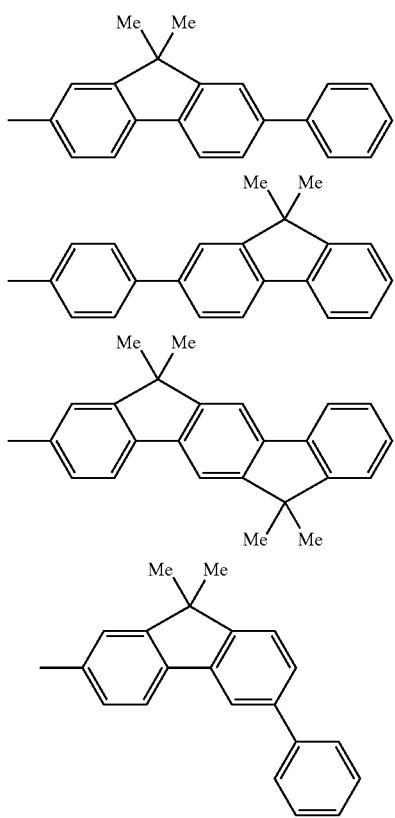
-continued
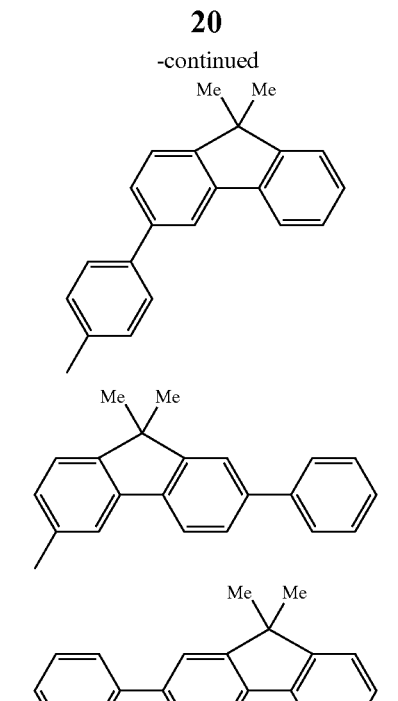
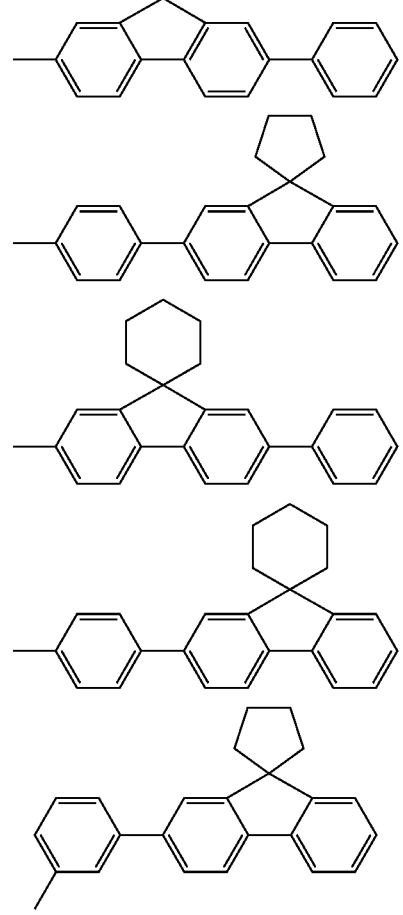

-continued
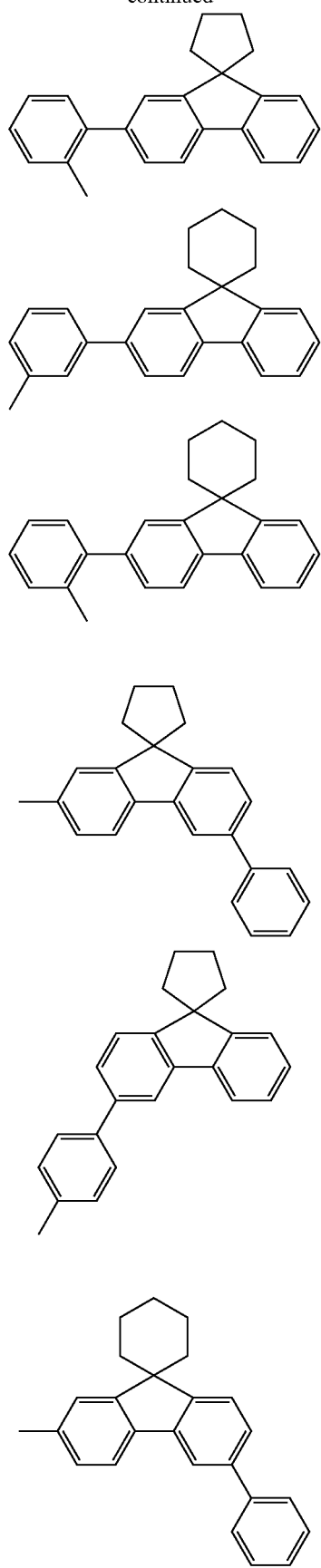
-continued
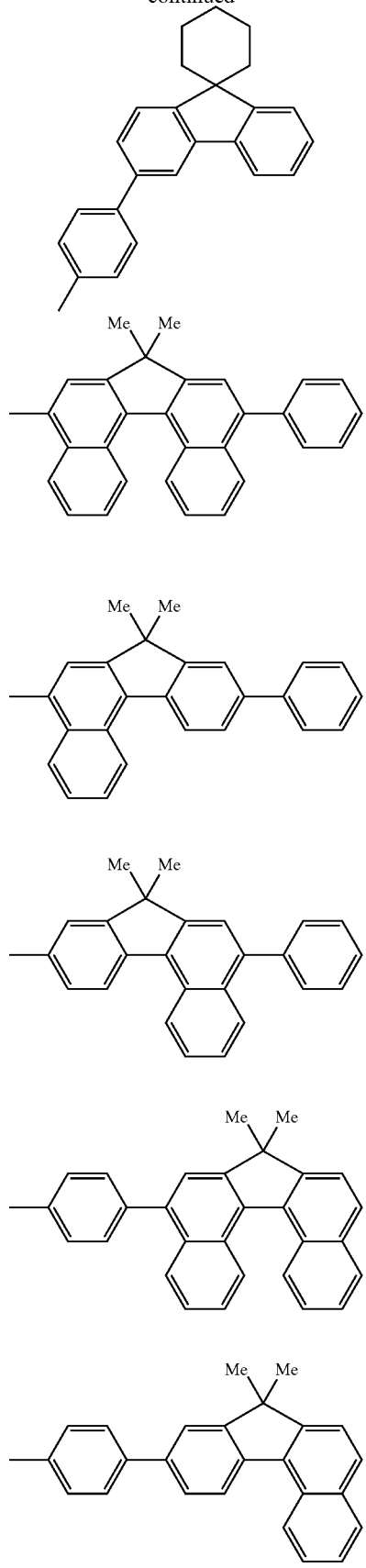

(2) Group 5:
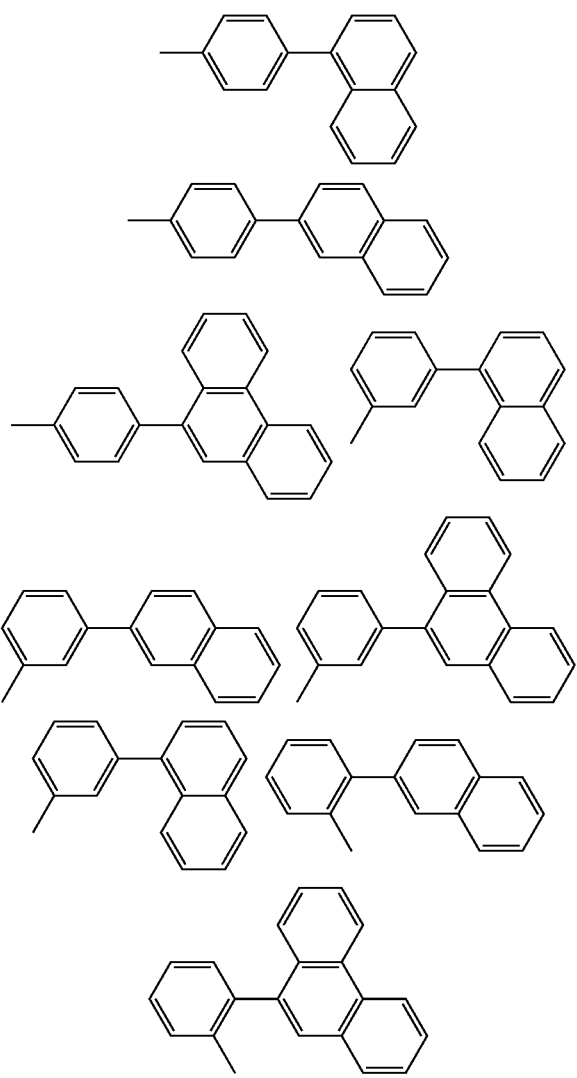
(2) Group 6:
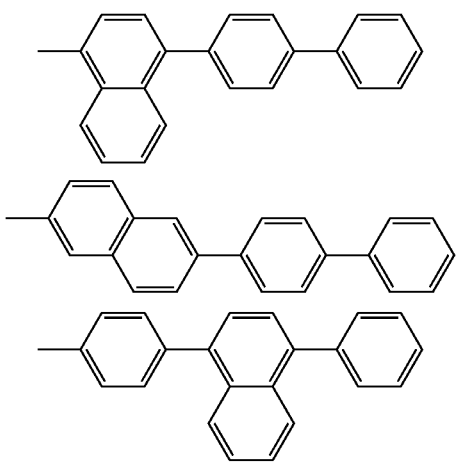
-continued
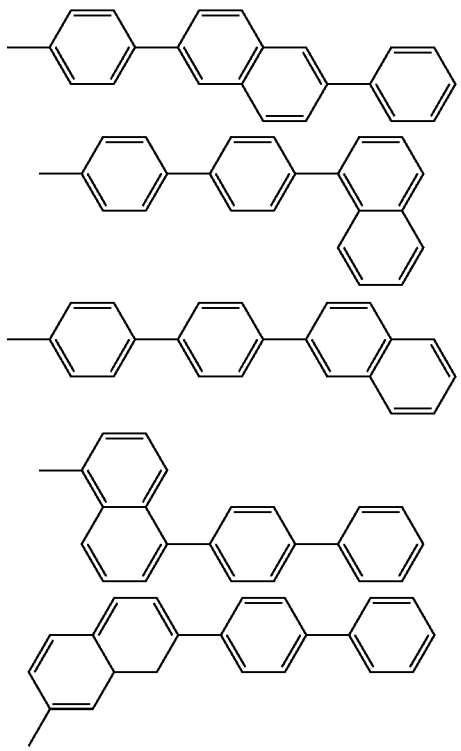
For specific examples of moieties represented by general formula (3), those listed in the following Groups 1 to 4 can be cited.
(3) Group 1:
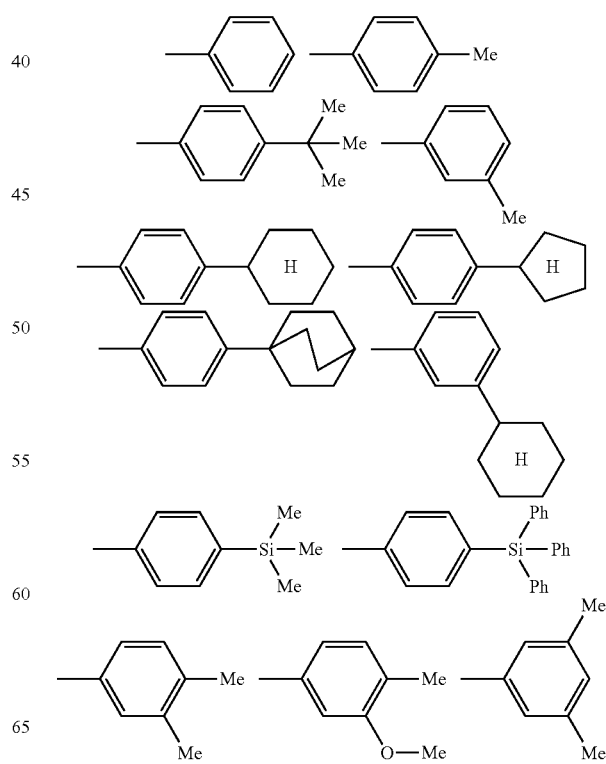

-continued
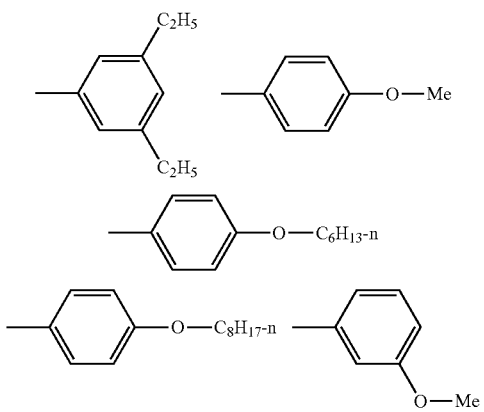
(3) Group 2:
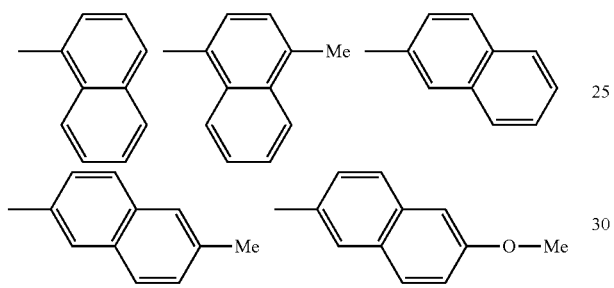
(3) Group 3:
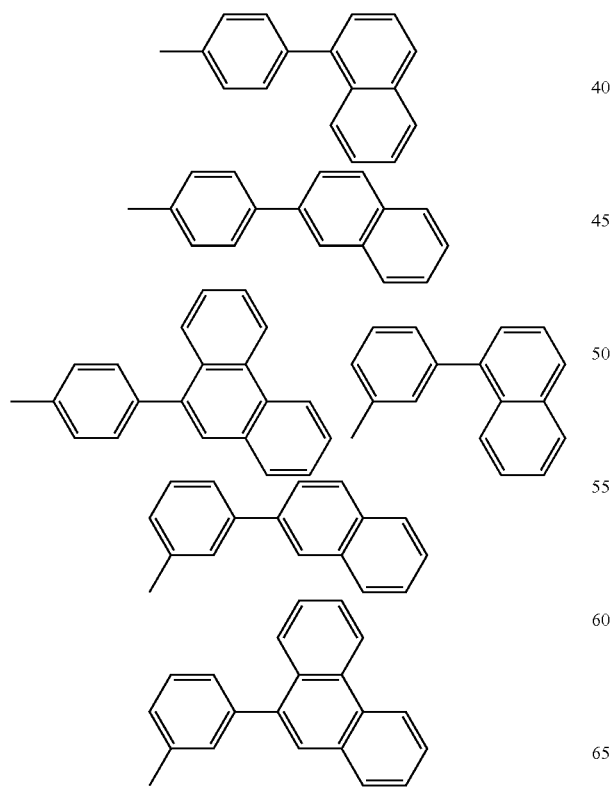
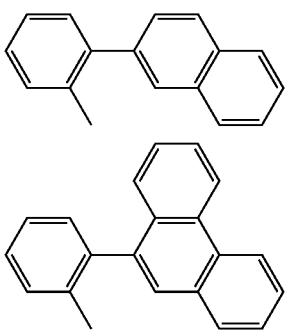
(3) Group 4:
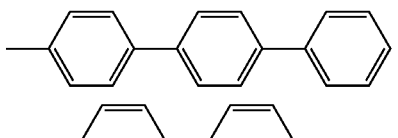
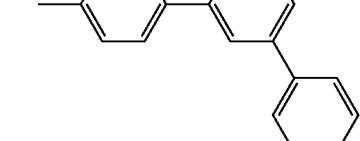
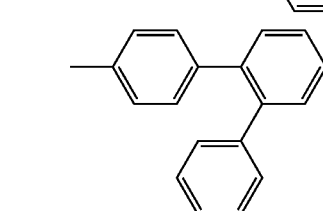
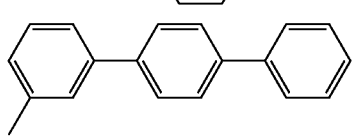
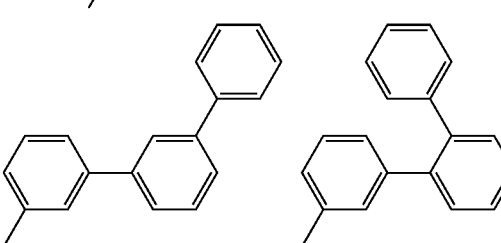
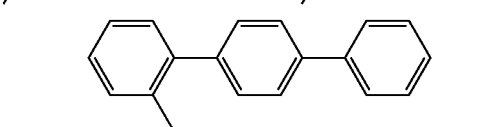
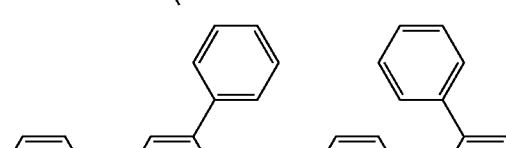
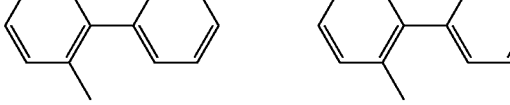

-continued

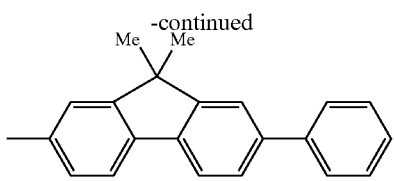

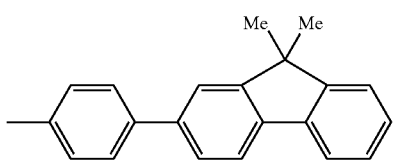

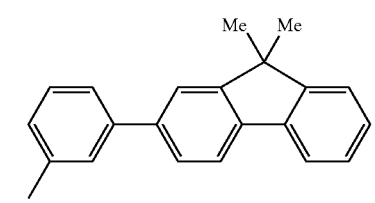

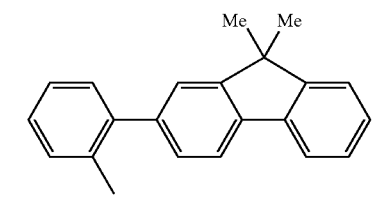

In an aromatic amine derivative of the present invention represented by general formula (1), examples of preferable combinations of $Ar_1$ and $Ar_2$, in terms of combinations of general formulas (1) and (2), are as follows:

(2) Group 1/(3) Group 1, (2) Group 1/(3) Group 2, (2) Group 1/(3) Group 3, (2) Group 1/(3) Group 4, (2) Group 2/(3) Group 1, (2) Group 2/(3) Group 2, (2) Group 3/(3) Group 1, (2) Group 3/(3) Group 2, (2) Group 3/(3) Group 3, (2) Group 3/(3) Group 4, (2) Group 4/(3) Group 1, (2) Group 4/(3) Group 2, (2) Group 5/(3) Group 1, (2) Group 5/(3) Group 2, (2) Group 5/(3) Group 3, (2) Group 5/(3) Group 4, (2) Group 6/(3) Group 1, and (2) Group 6/(3) Group 2. More preferable combinations are (2) Group 1/(3) Group 1, (2) Group 1/(3) Group 2, (2) Group 1/(3) Group 4, (2) Group 2/(3) Group 1, (2) Group 4/(3) Group 1, (2) Group 5/(3) Group 1, (2) Group 5/(3) Group 2, and (2) Group 5/(3) Group 3. Yet preferable combinations are (2) Group 1/(3) Group 1, and (2) Group 1/(3) Group 4.

In an aromatic amine derivative represented by general formula (1) of the present invention, $Ar_1$ and $Ar_2$ are preferably different groups.

The total number of carbon atoms of $Ar_1$ plus $Ar_2$ is preferably 36 to 22, more preferably 34 to 22, yet preferably 30 to 22.

In an aromatic amine derivative represented by general formula (1) of the present invention, when $Ar_1$ and $Ar_2$ represent the same group, R' and R" preferably represent a straight or branched $C_{2-12}$ alkyl group or $C_{3-10}$ cycloalkyl group, more preferably a straight or branched $C_{3-12}$ alkyl group or $C_{5-10}$ cycloalkyl group.

In an aromatic amine derivative represented by general formula (1) of the present invention, among groups represented by general formula (2), preferable are those represented by general formula (4), and those represented by general formulas (6) and (7) are also preferable.

Moreover, among groups represented by general formula (3), preferable are those represented by general formula (5).

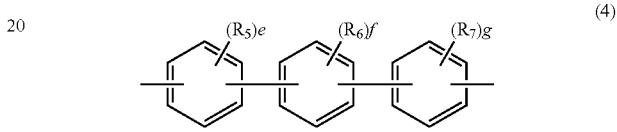

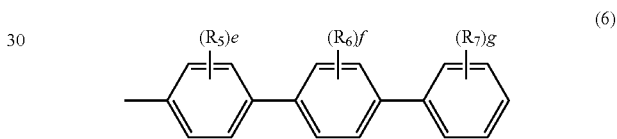

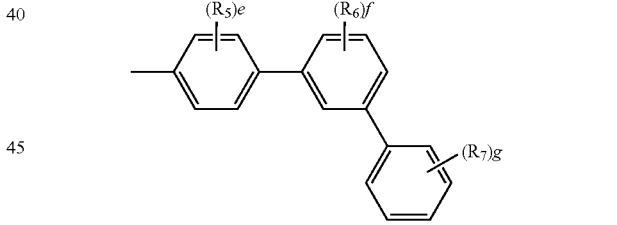

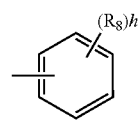

In general formulas (4) and (5), $R_5$ to $R_8$, and e, f, g and h are defined the same as those in general formulas (2) and (3).

In general formulas (6) and (7), $R_5$ to $R_7$, and e, f and g are defined the same as those in general formula (2).

Specific examples of aromatic amine derivatives of the present invention represented by general formula (1) are as follows:

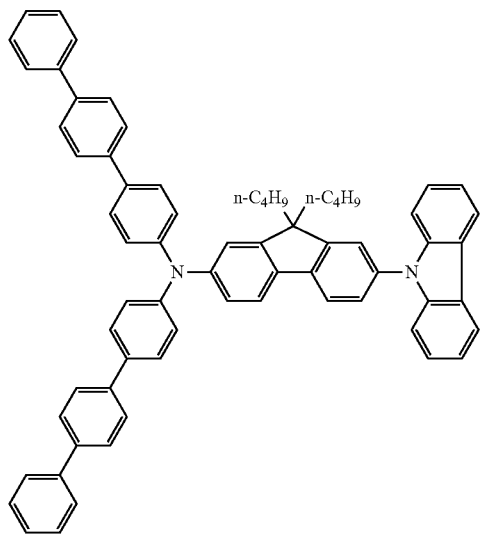
[A-1]
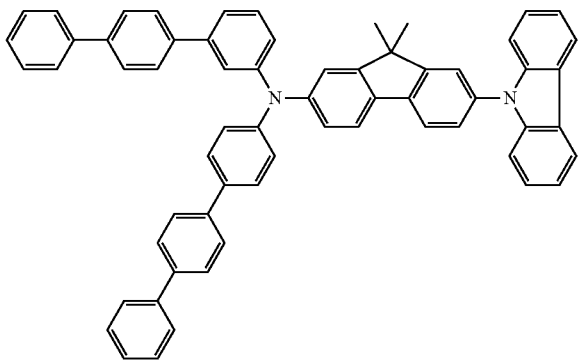
[A-2]
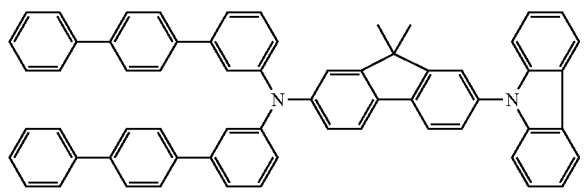
[A-3]
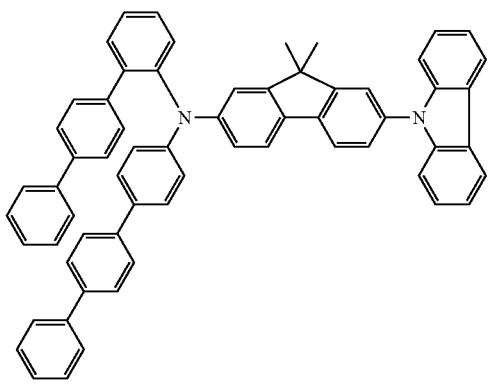
[A-4]
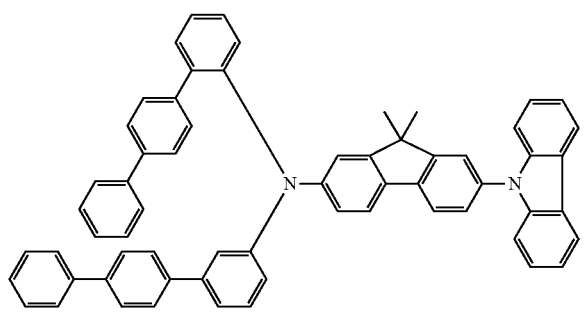
[A-5]
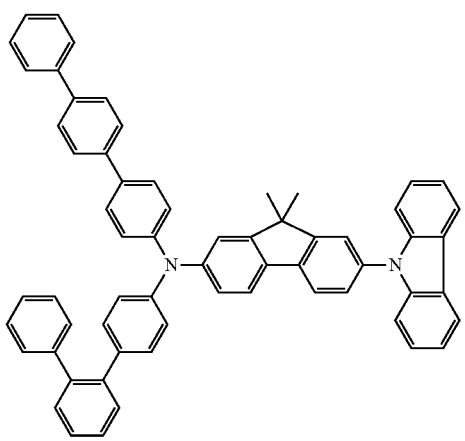
[A-6]

-continued
[A-7]
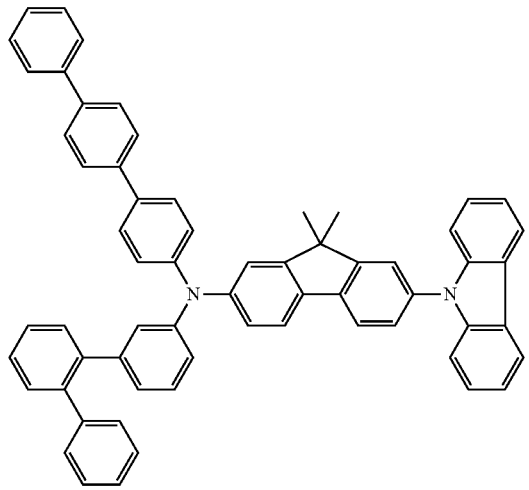
[A-8]
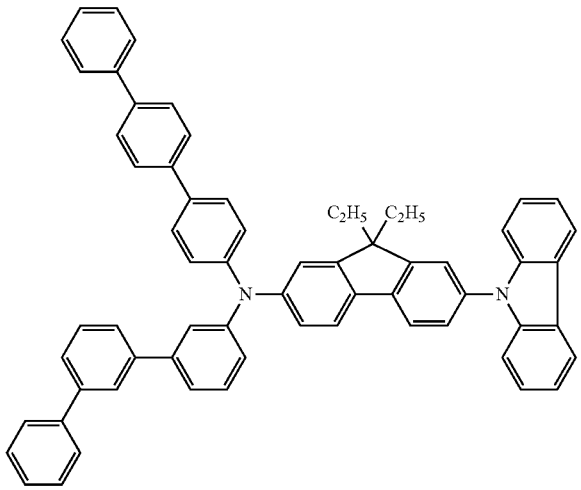
[A-9]
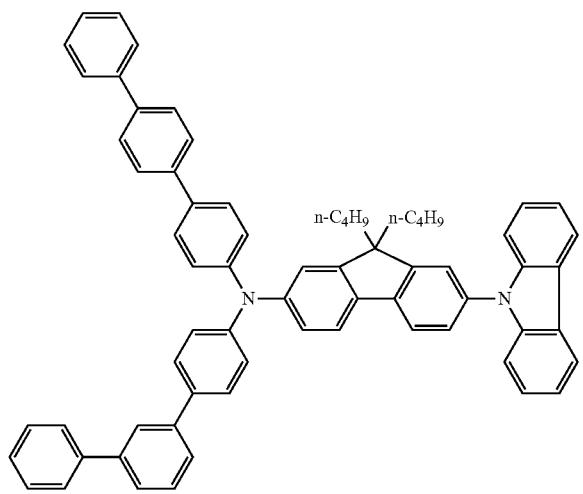
[A-10]
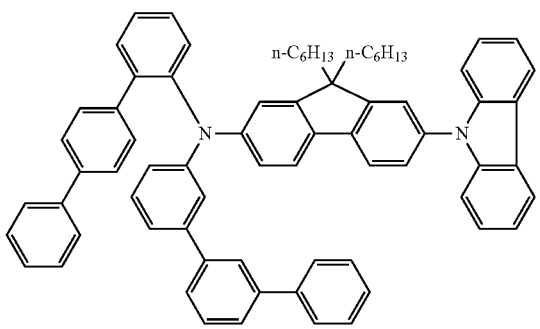
[A-11]
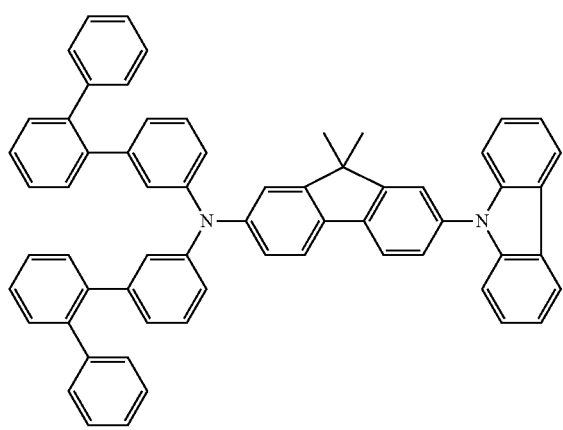
[A-12]
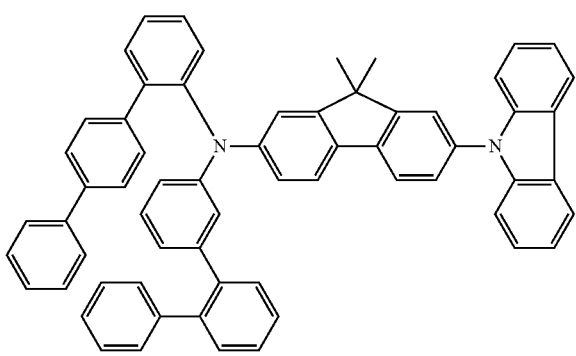

-continued
[A-13]
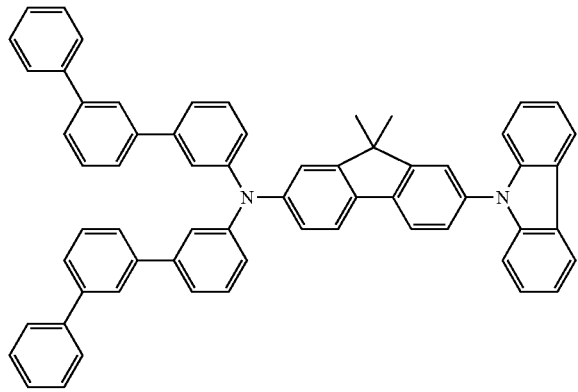
[A-14]
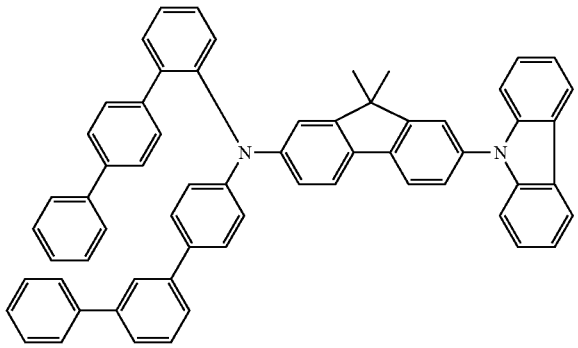
[A-15]
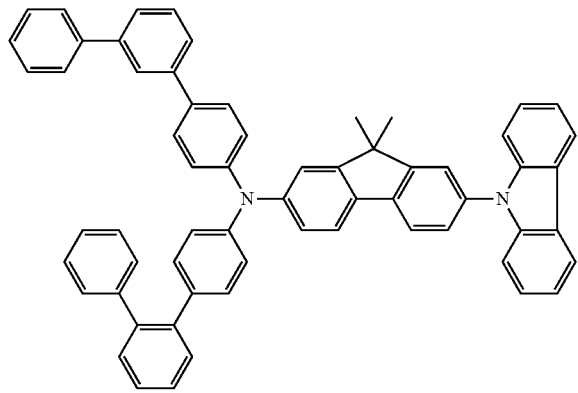
[A-16]
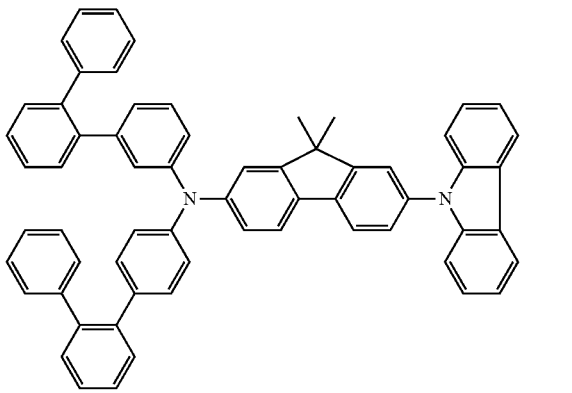
[A-17]
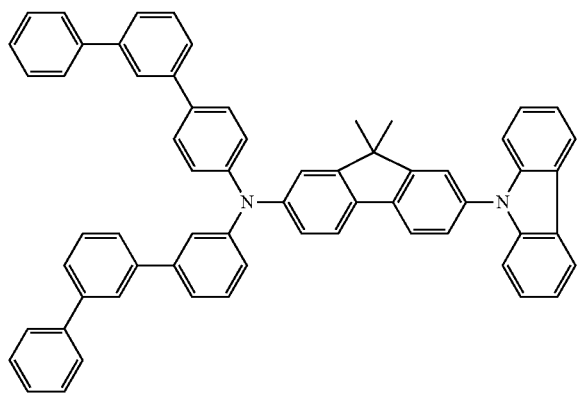
[A-18]
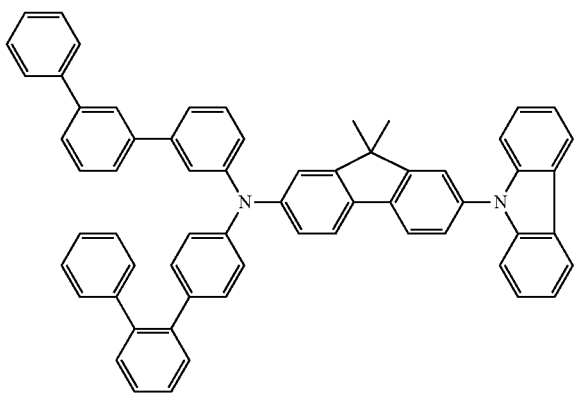
[A-19]
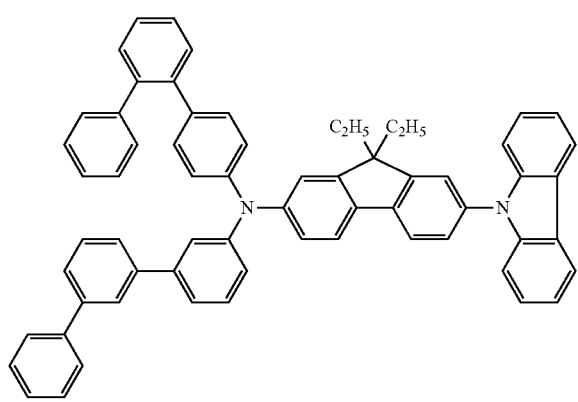
[A-20]
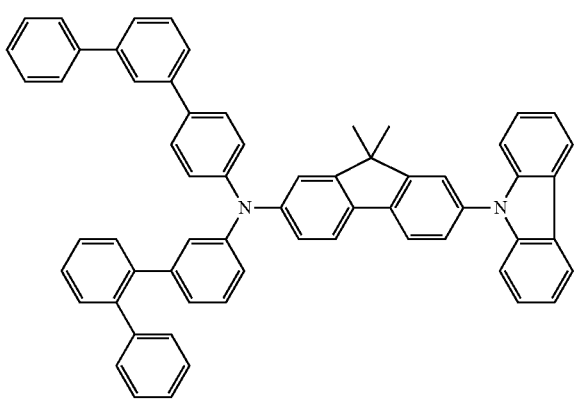

-continued
[A-21]
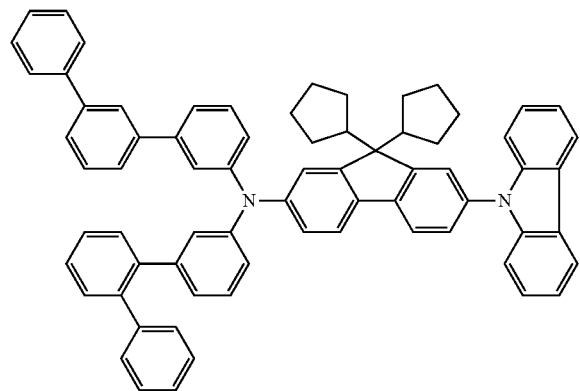
[A-22]
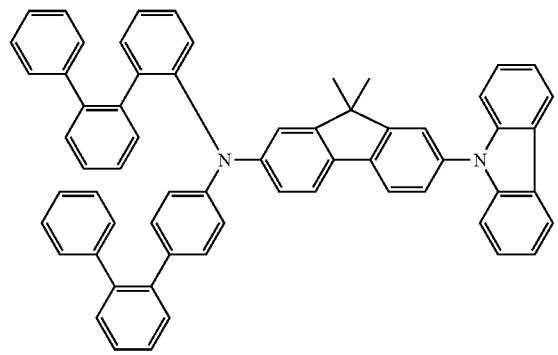
[A-23]
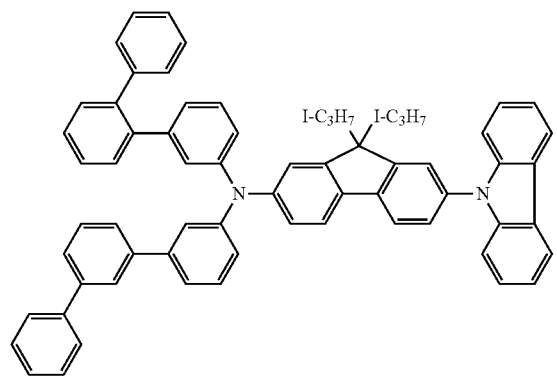
[A-24]
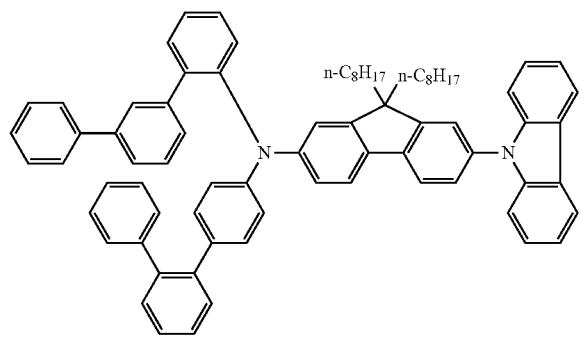
[A-25]
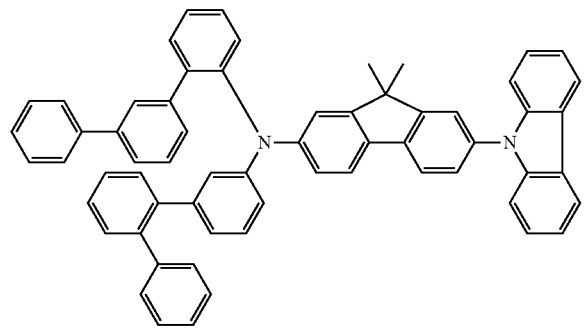
[A-26]
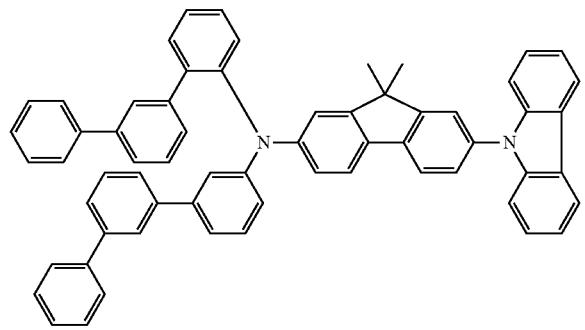
[A-27]
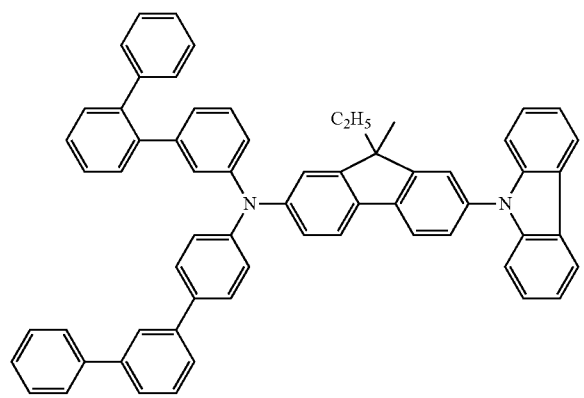
[A-28]
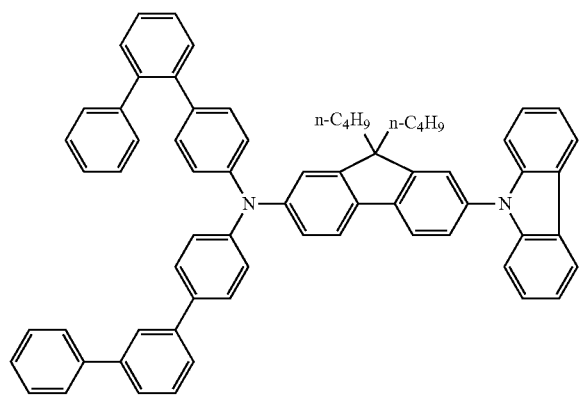

[A-29]
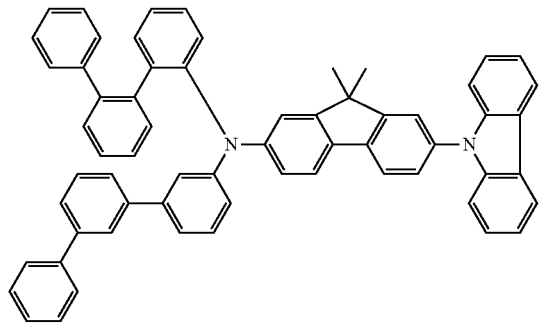
[A-30]
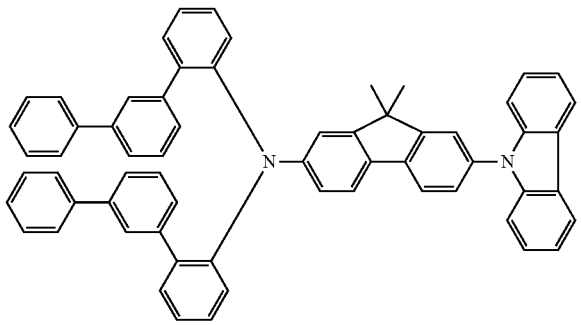
[A-31]
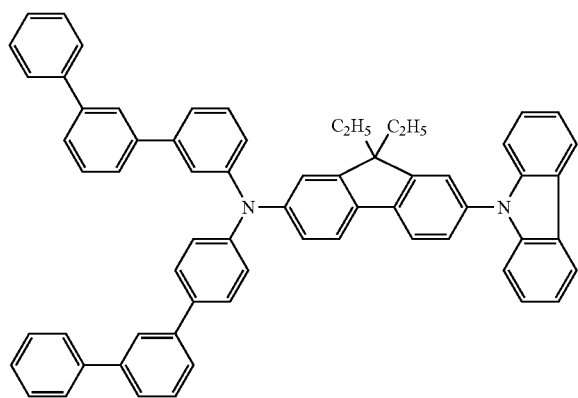
[A-32]
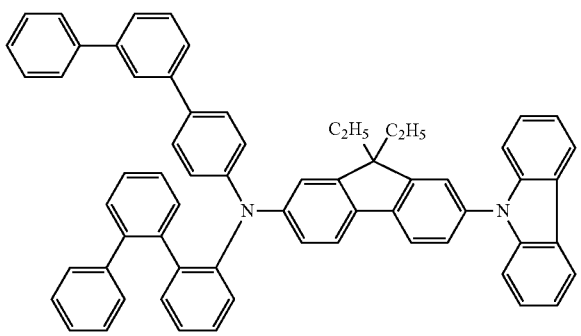
[A-33]
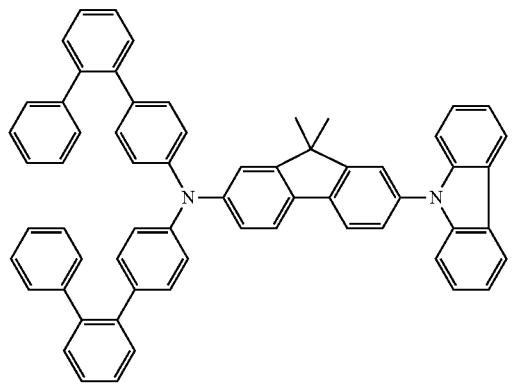
[A-34]
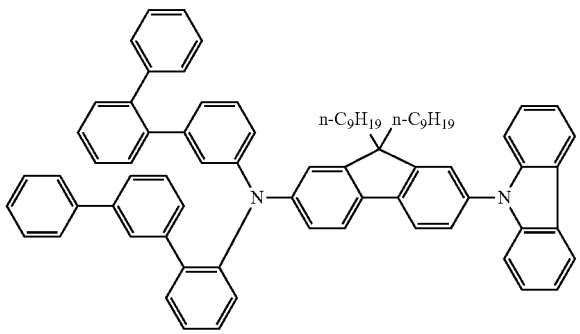
[A-35]
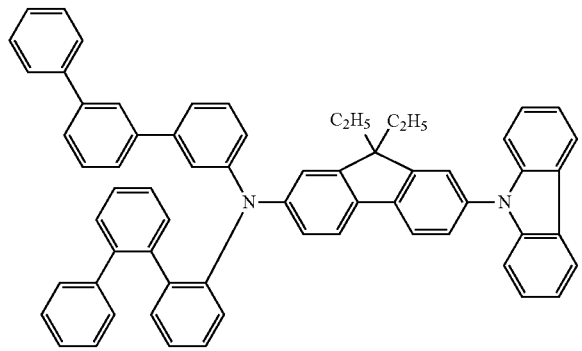
[A-36]
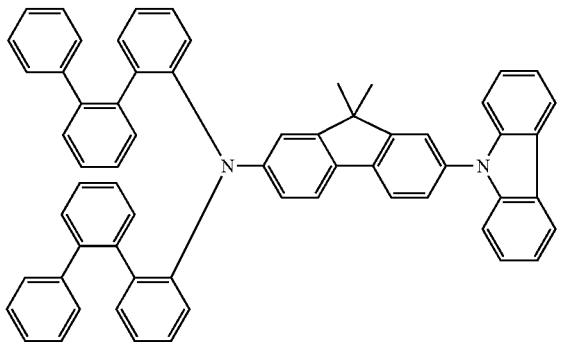

-continued
[A-37]
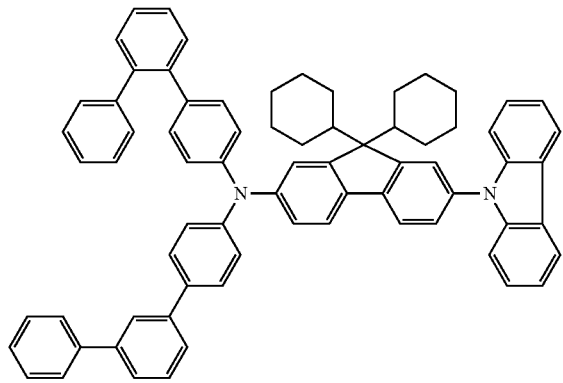
[A-38]
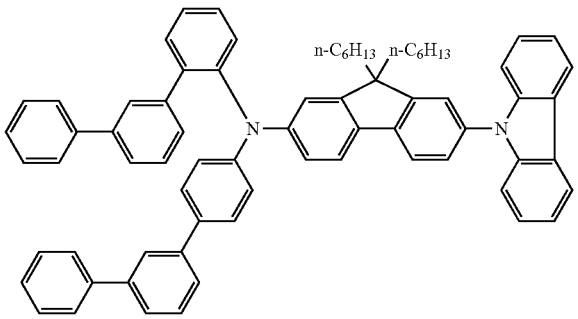
[A-39]
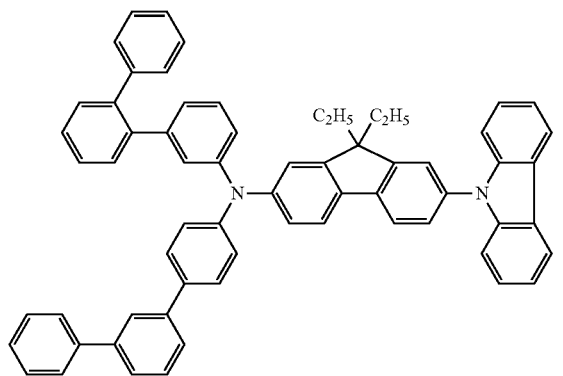
[A-40]
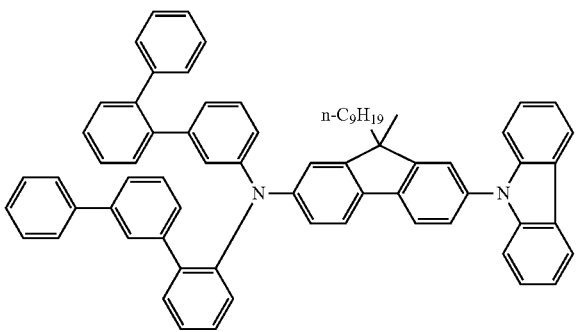
[A-41]
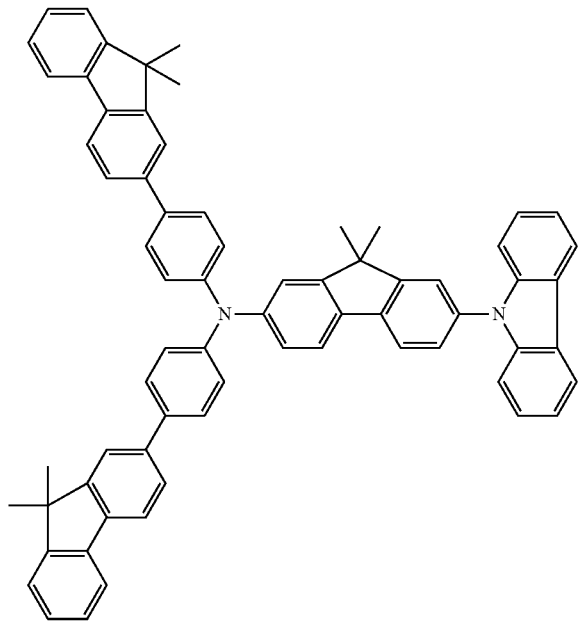
[A-42]
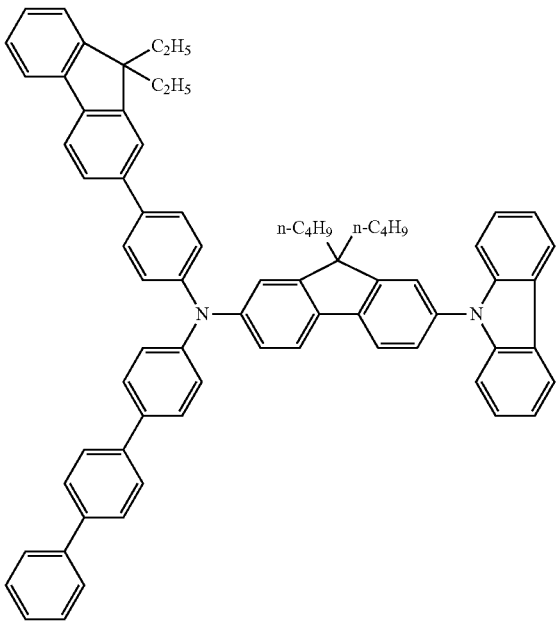

-continued
[A-43]
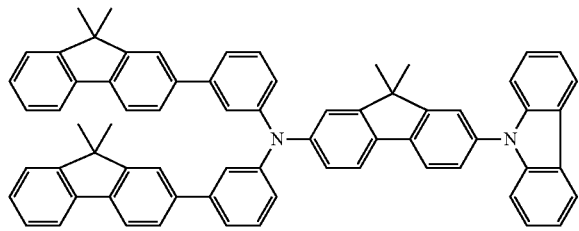
[A-44]
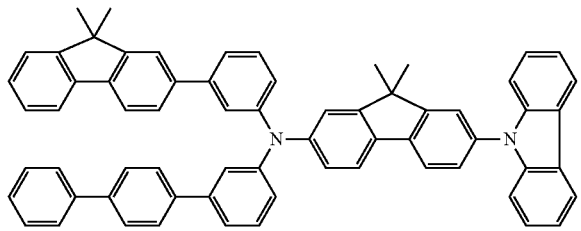
[A-45]
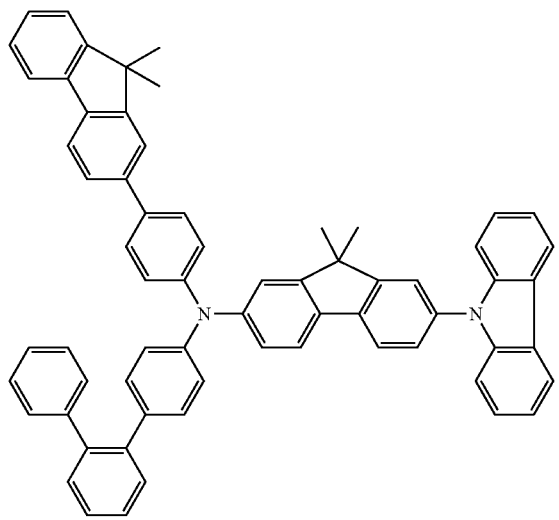
[A-46]
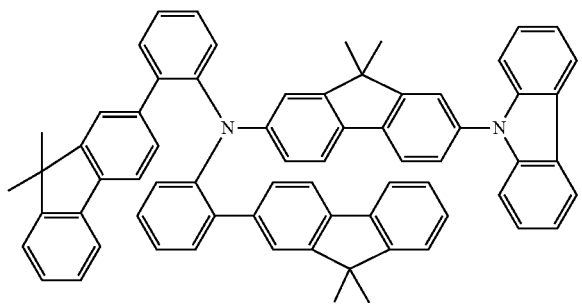
[A-47]
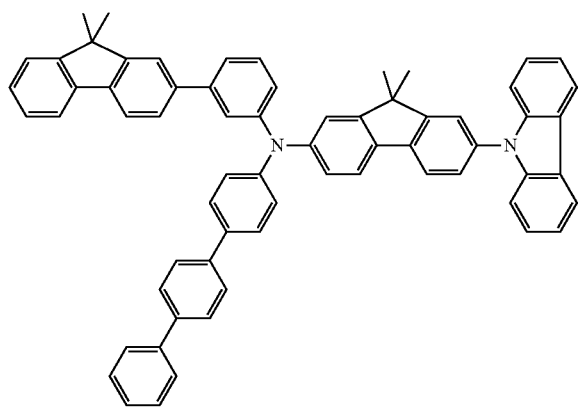
[A-48]
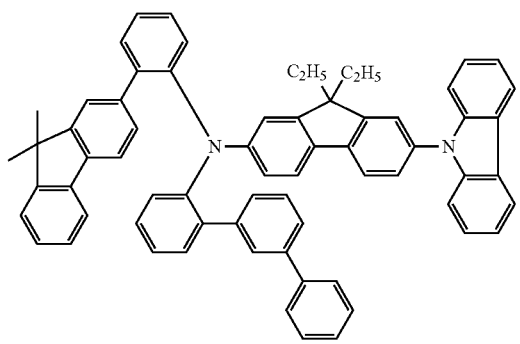

-continued
[A-49]
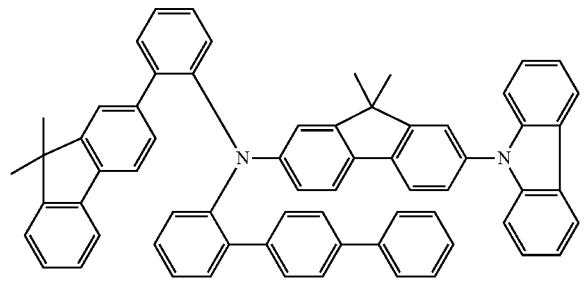
[A-50]
[B-1]
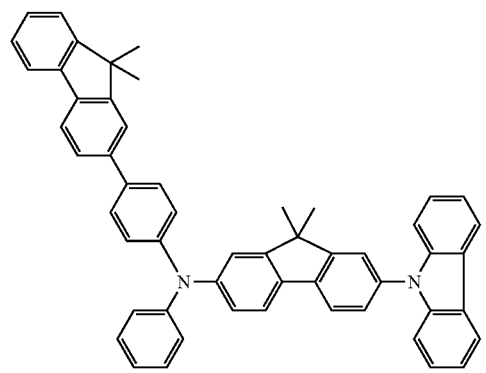
[B-2]
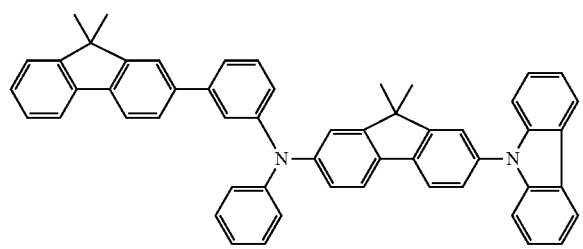
[B-3]
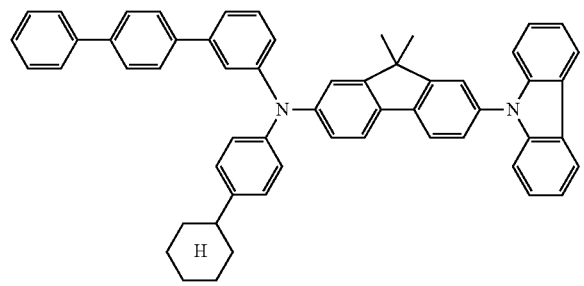
[B-4]
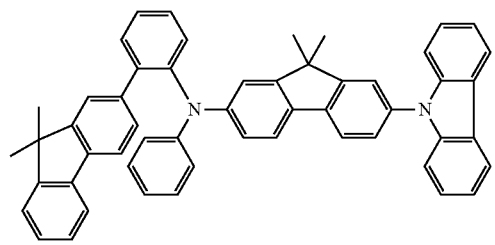
[B-5]
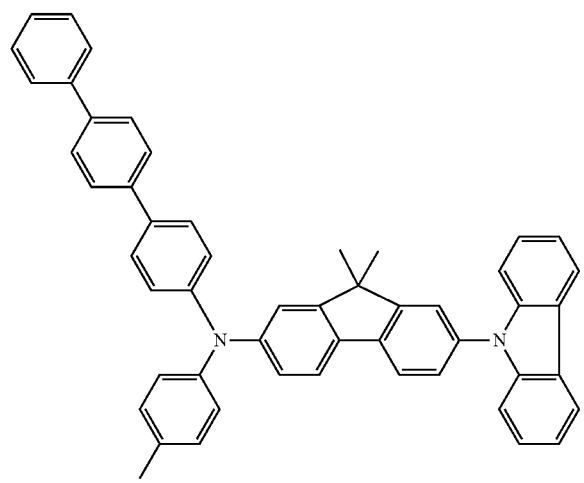
[B-6]
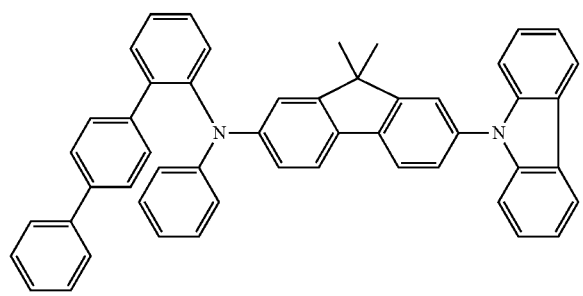

-continued
[B-7]
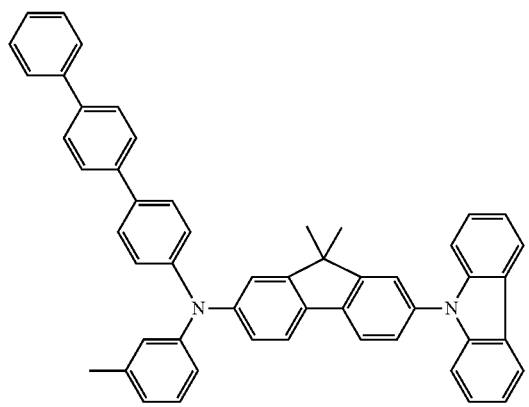
[B-8]
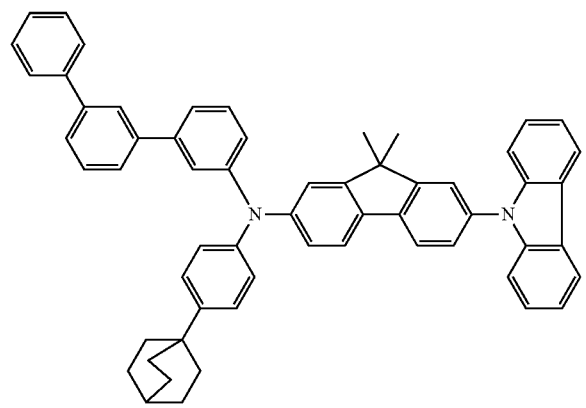
[B-9]
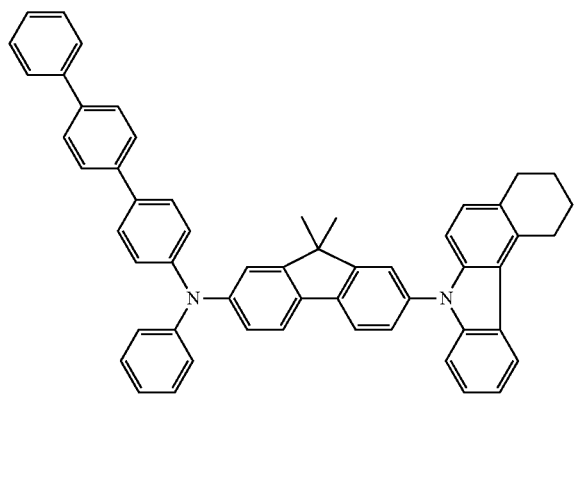
[B-10]
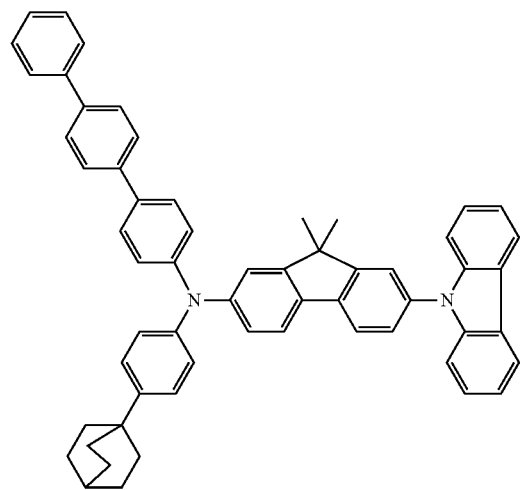
[B-11]
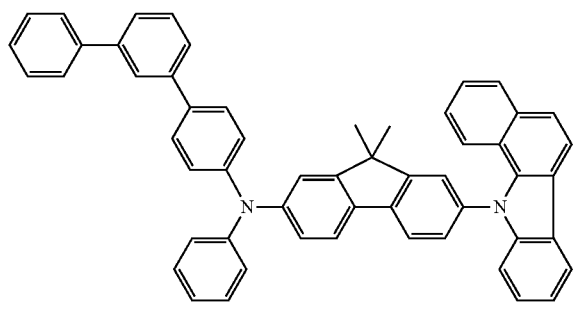
[B-12]
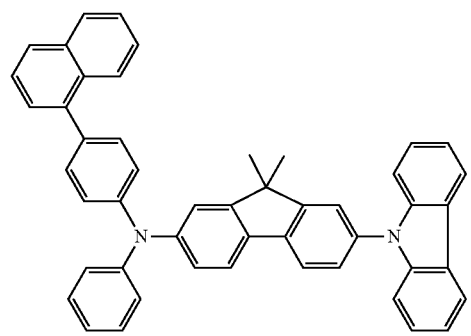

-continued
[B-13]
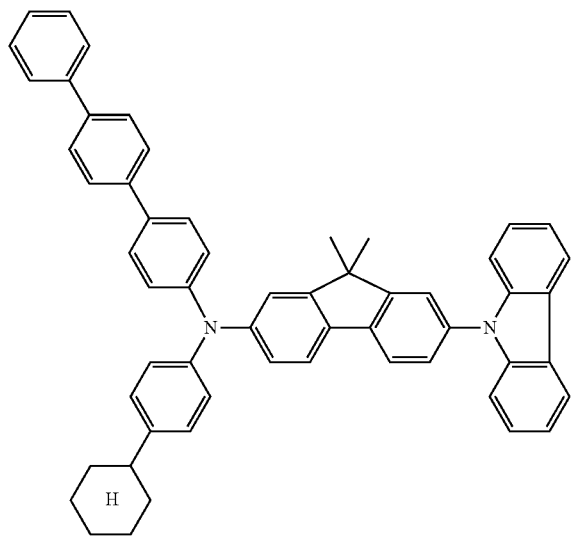
[B-14]
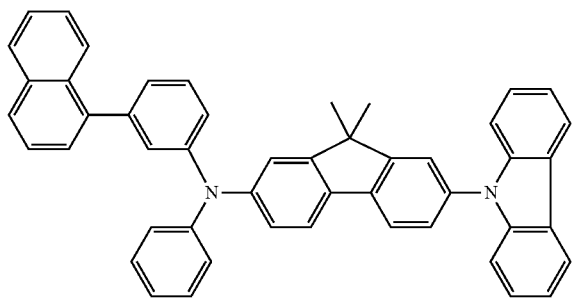
[B-15]
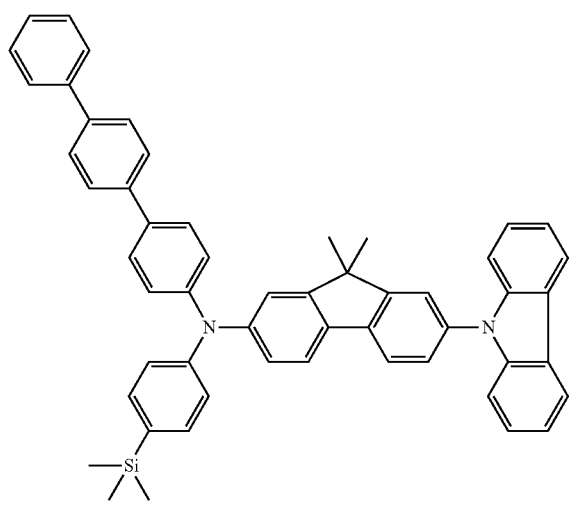
[B-16]
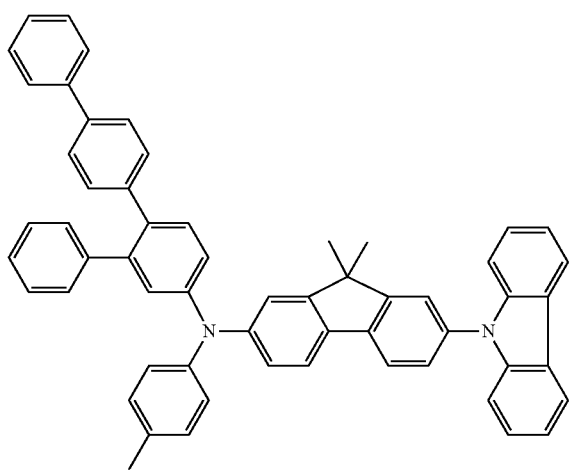
[B-17]
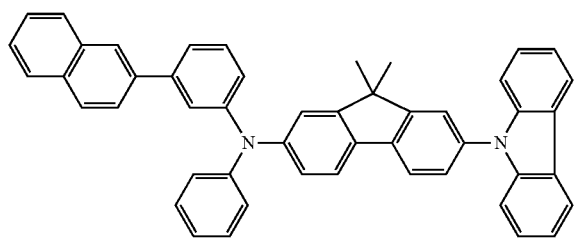
[B-18]
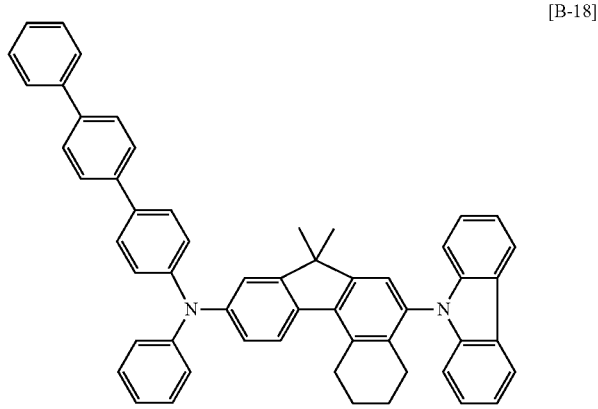

-continued
[B-19]
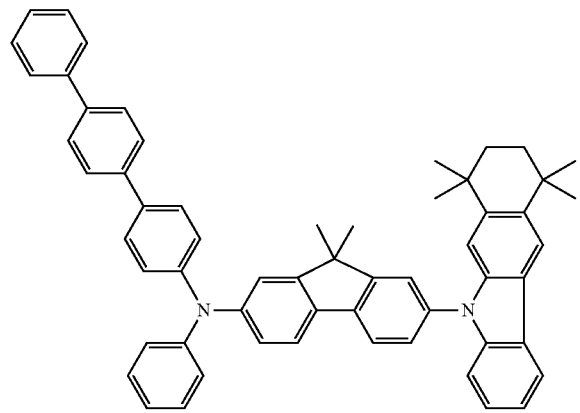
[B-20]
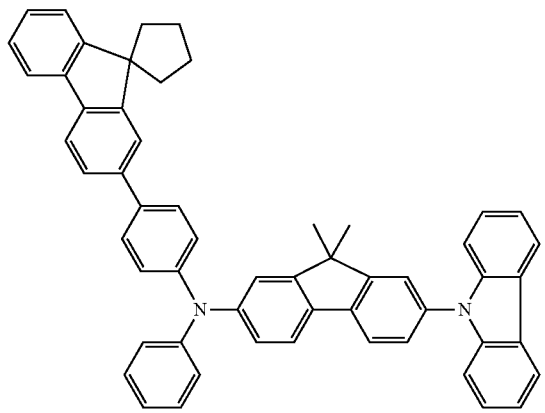
[B-21]
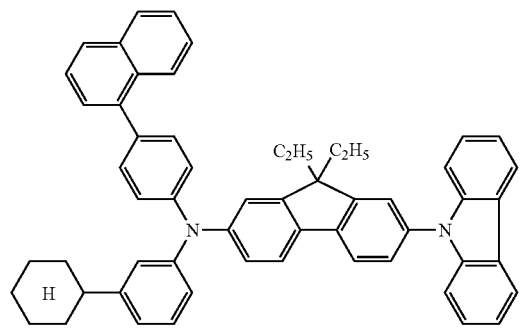
[B-22]
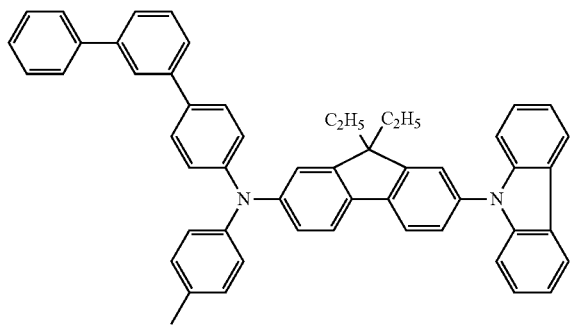
[B-23]
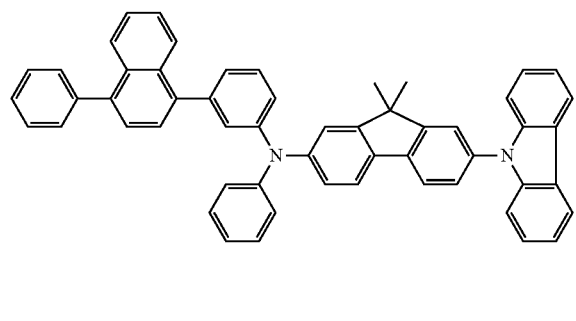
[B-24]
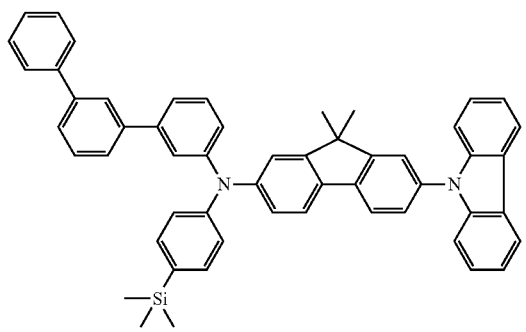
[B-25]
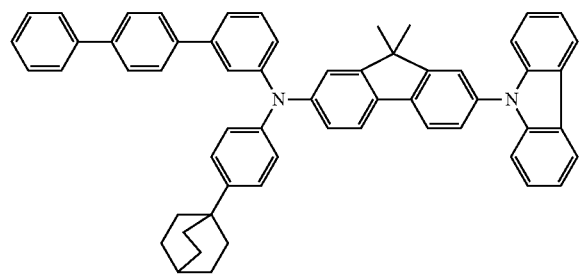
[B-26]
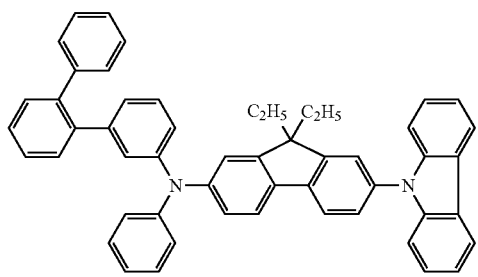

-continued
[B-27]
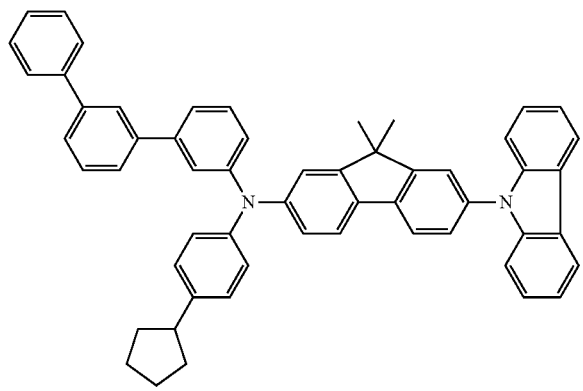
[B-28]
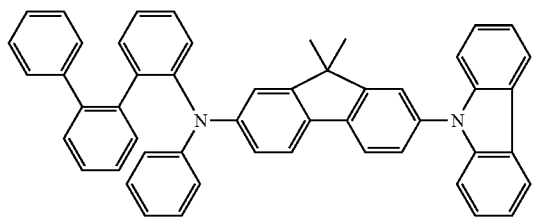
[B-29]
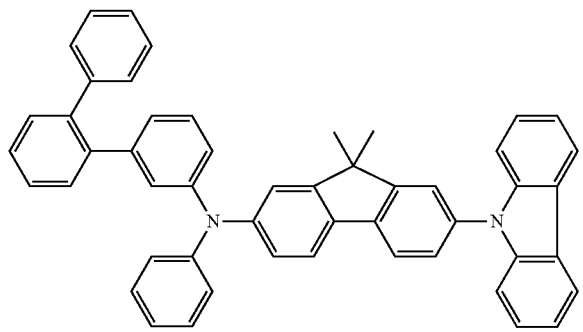
[B-30]
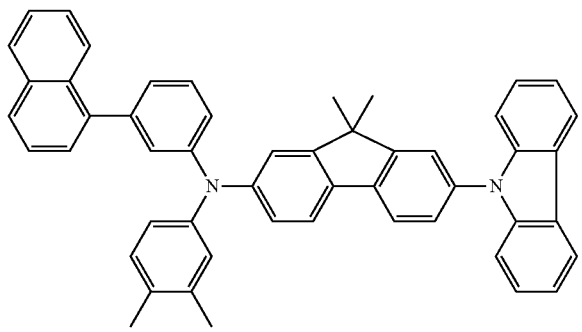
[B-31]
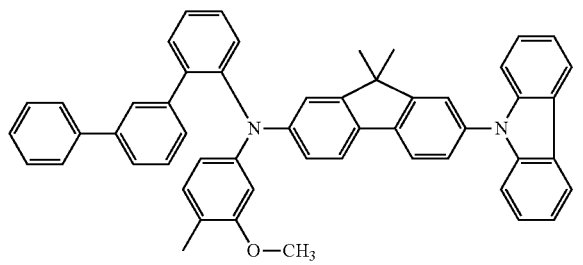
[B-32]
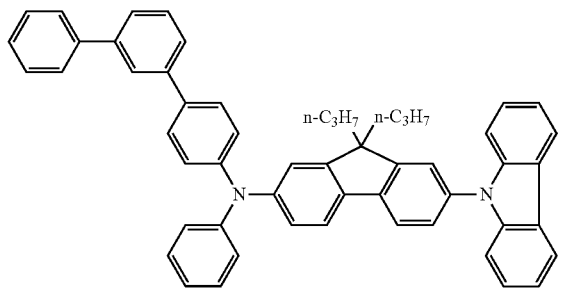
[B-33]
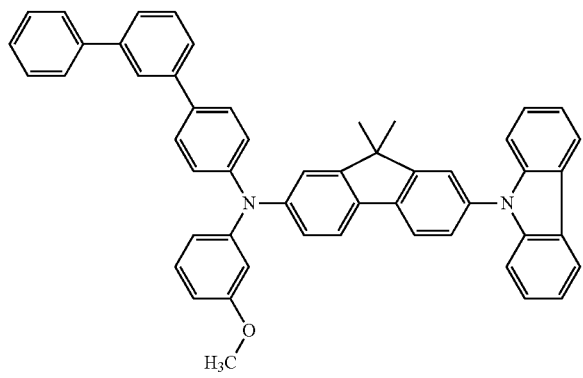
[B-34]
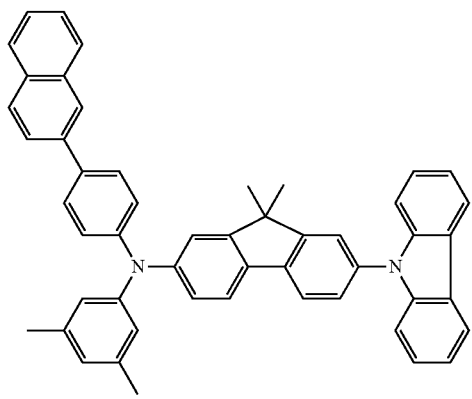

-continued
[B-35]
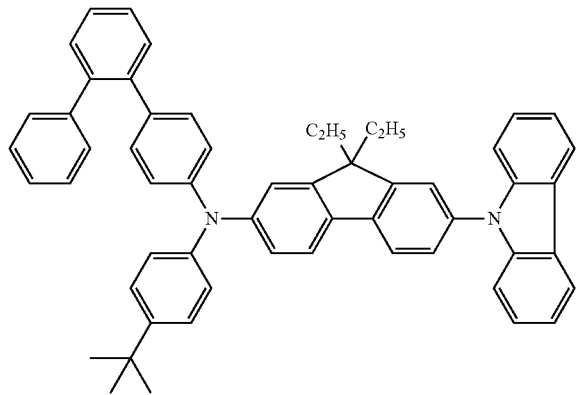
[B-36]
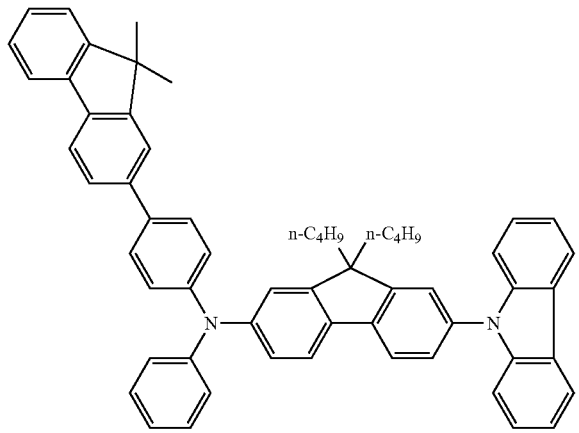
[B-37]
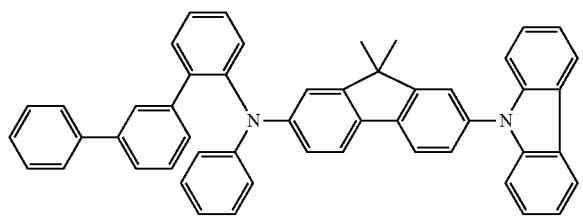
[B-38]
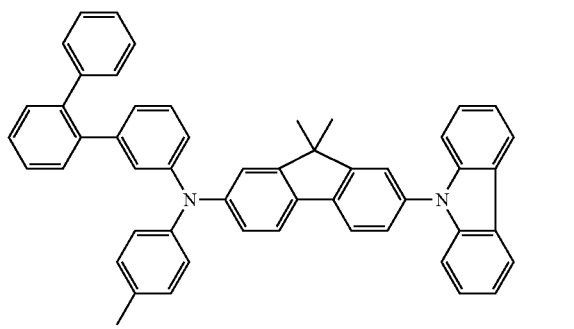
[B-39]
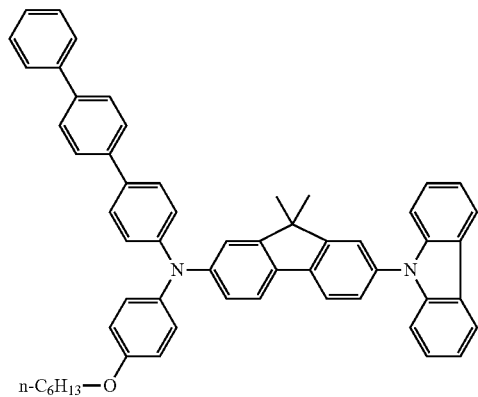
[B-40]
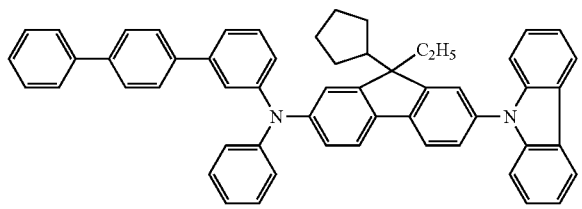
[B-41]
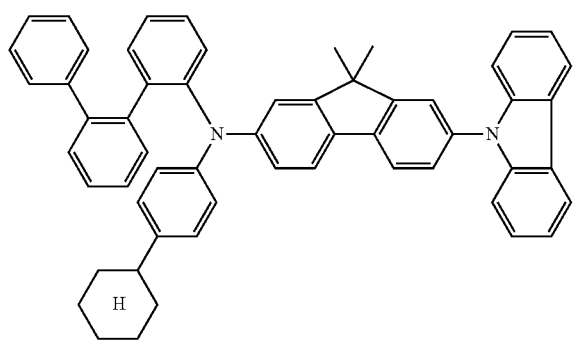
[B-42]
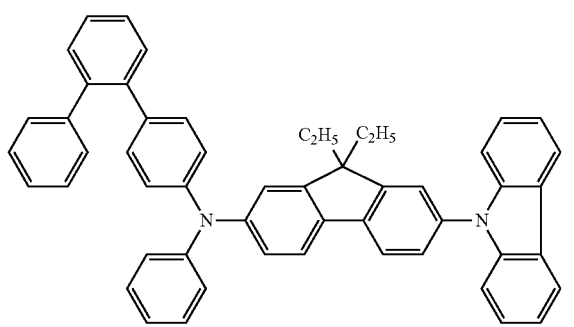

-continued
[B-43]
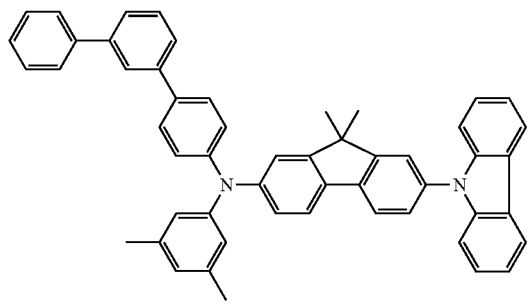
[B-44]
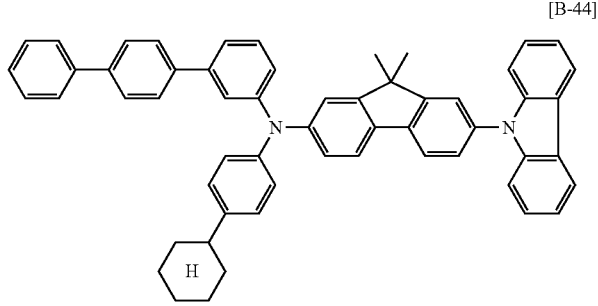
[B-45]
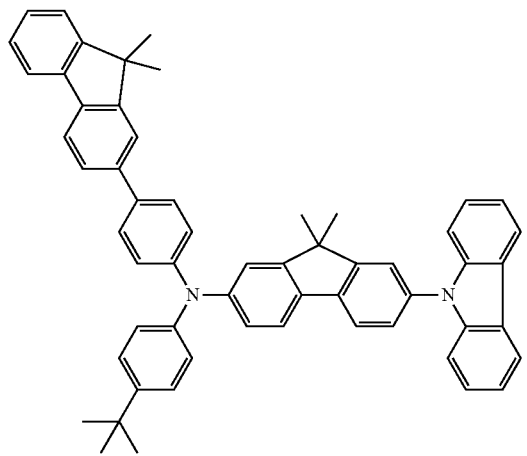
[B-46]
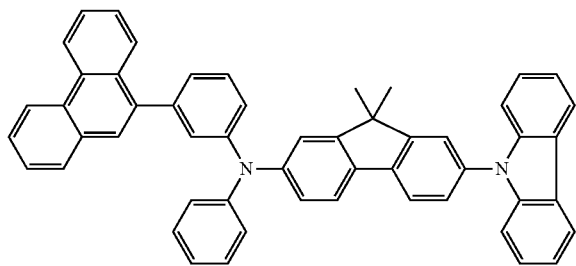
[B-47]
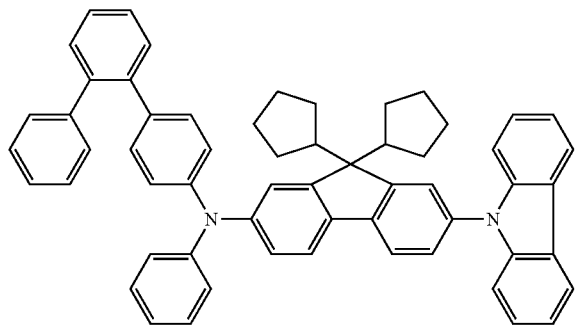
[B-48]
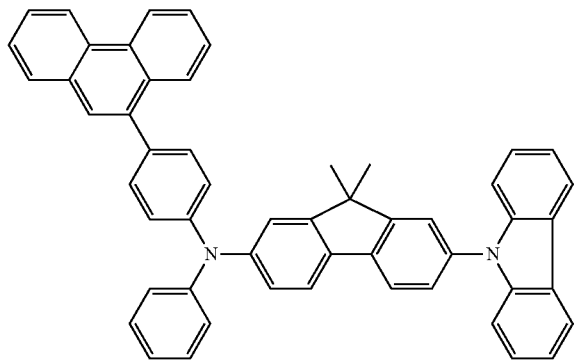
[B-49]
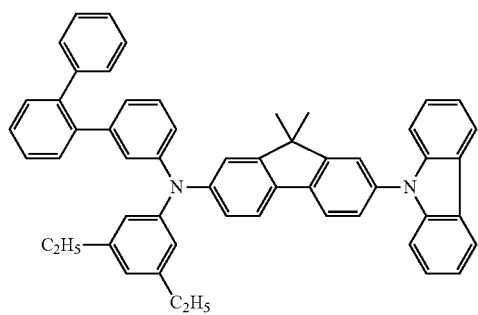
[B-50]
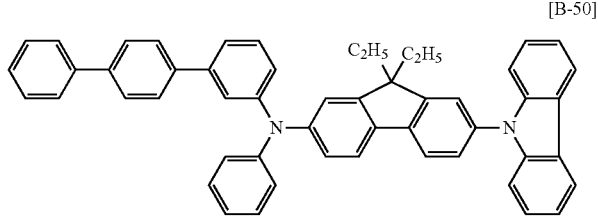

-continued
[B-51]
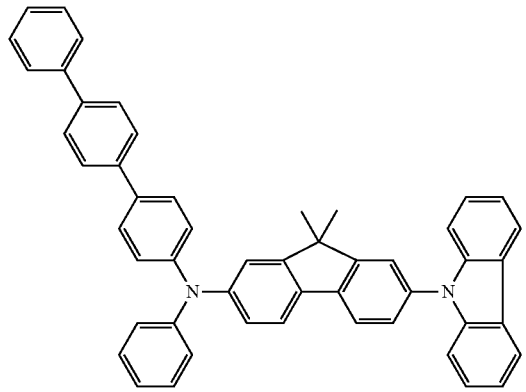
[B-52]
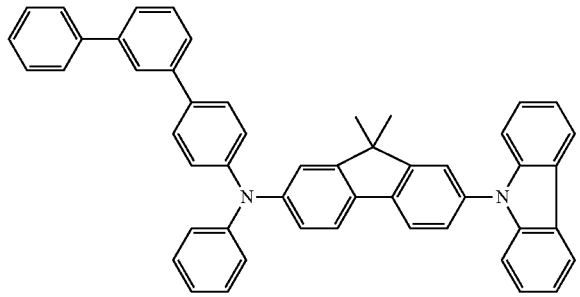
[B-53]
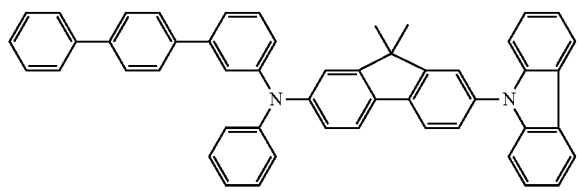
[B-54]
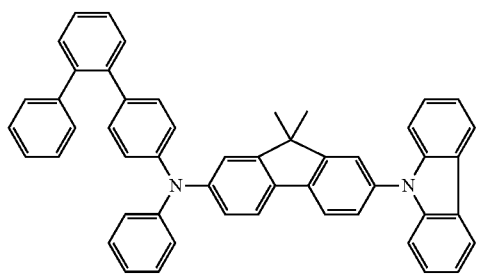
[B-55]
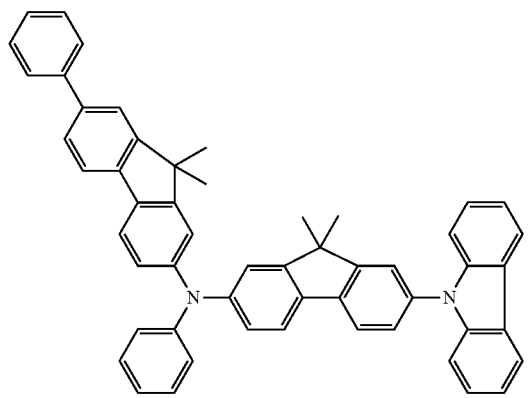
[B-56]
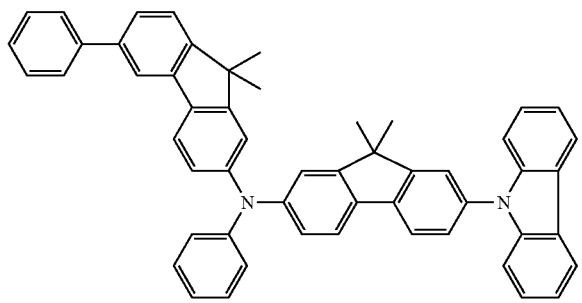
[B-57]
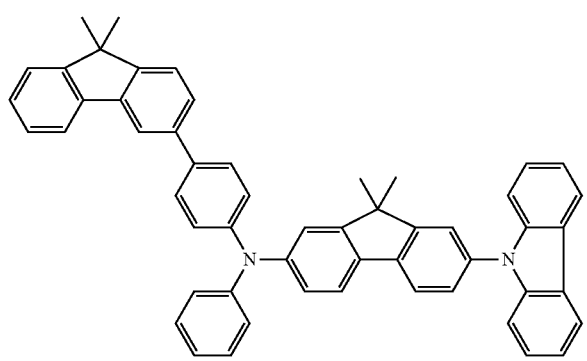
[B-58]
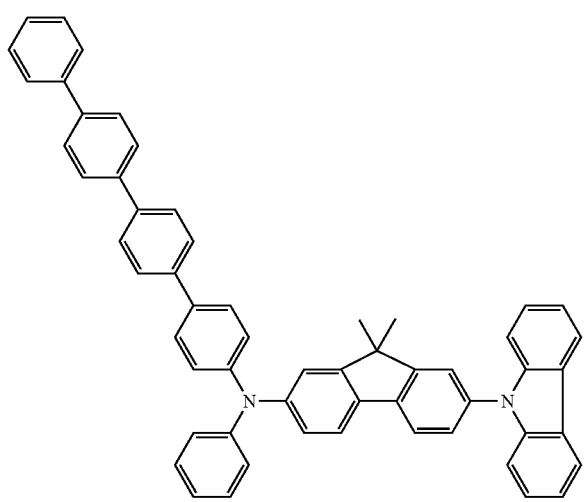

-continued
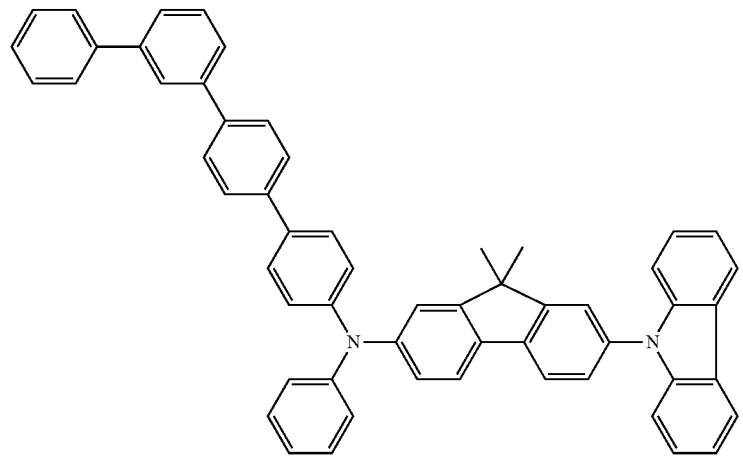
[B-59]
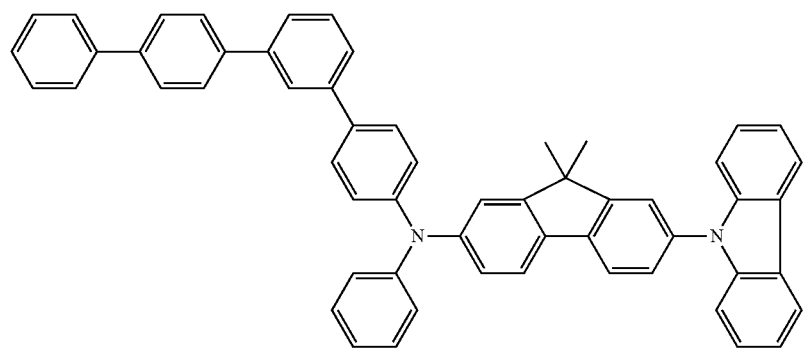
[B-60]
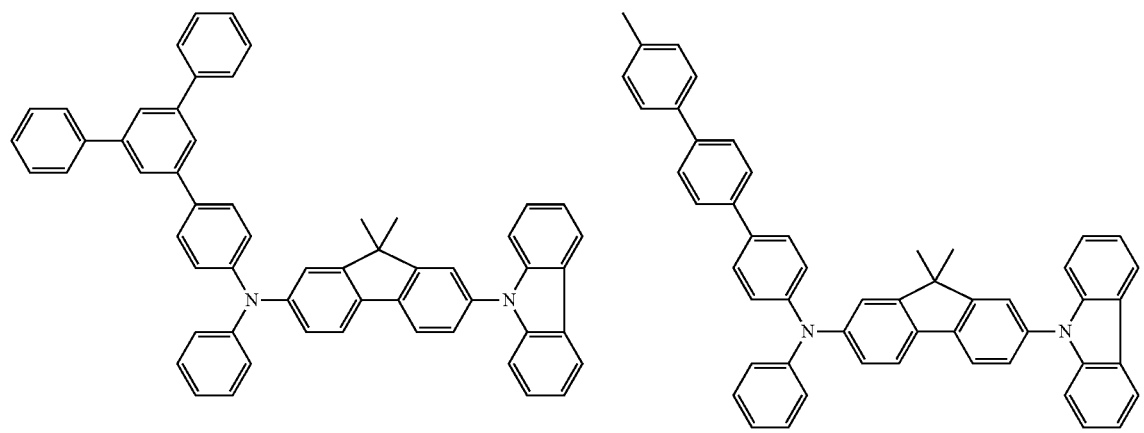
[B-61] [B-62]

-continued
[B-63]
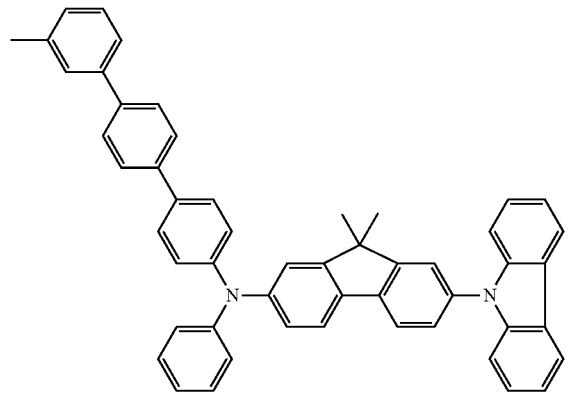
[B-64]
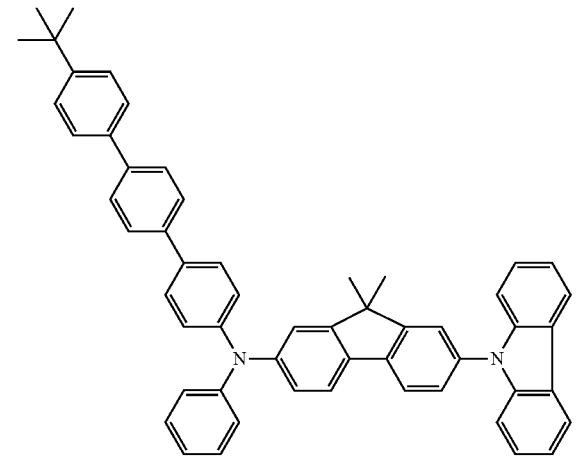
[B-65]
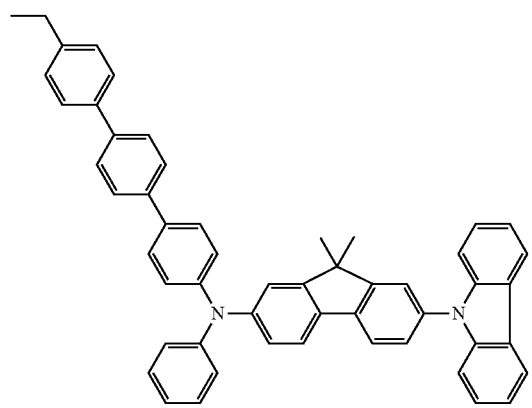
[B-66]
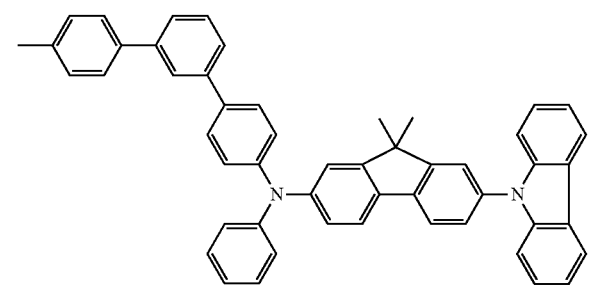
[B-67]
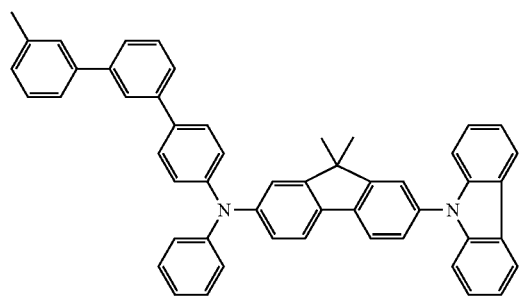
[B-68]
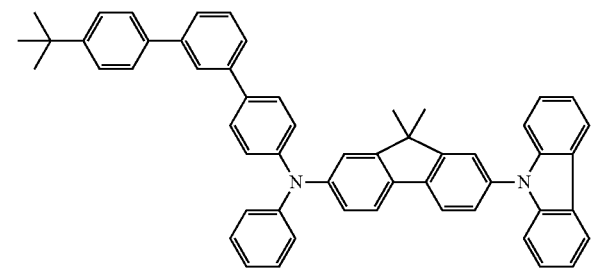
[B-69]
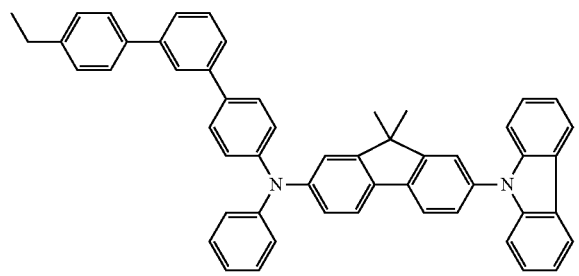
[B-70]
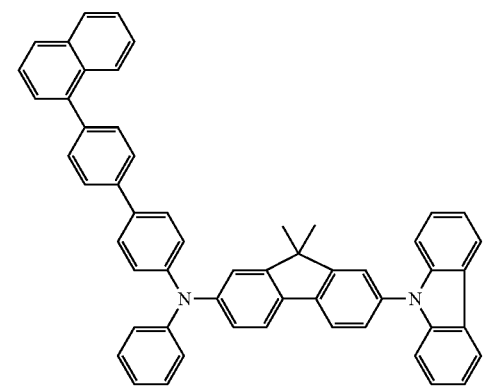

-continued
[B-71]
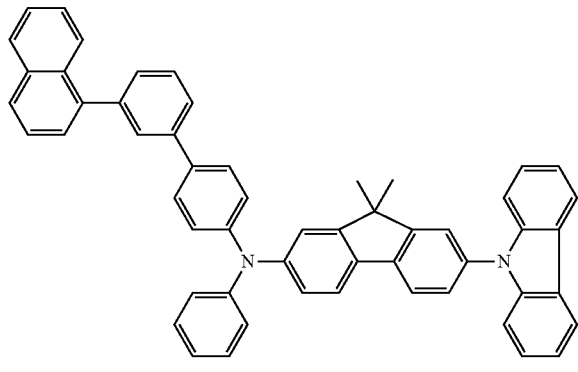
[B-72]
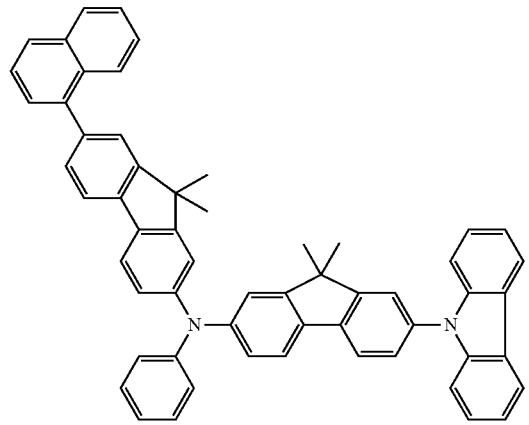
[B-73]
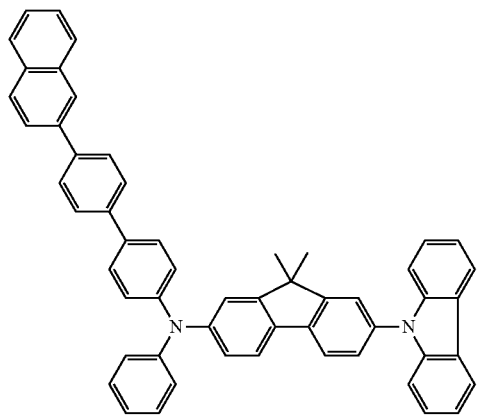
[B-74]
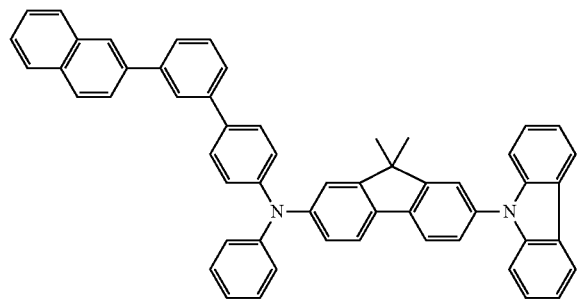
[B-75]
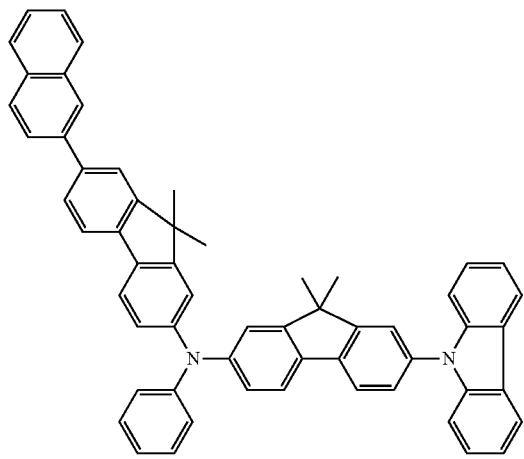
[C-1]
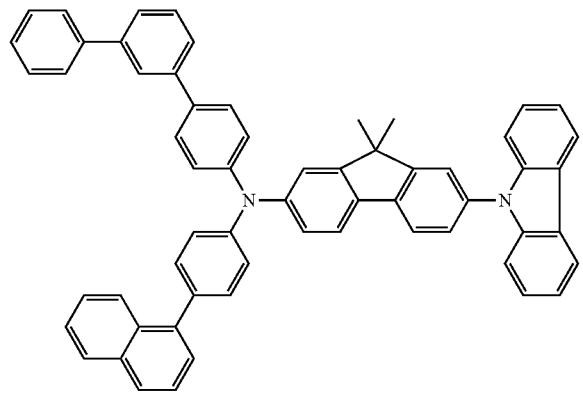

[C-2]
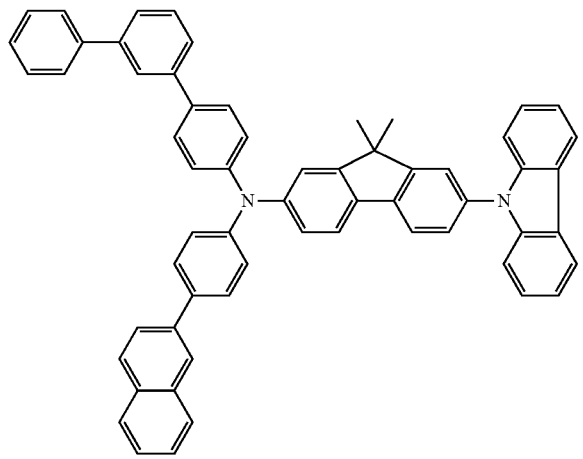
[C-3]
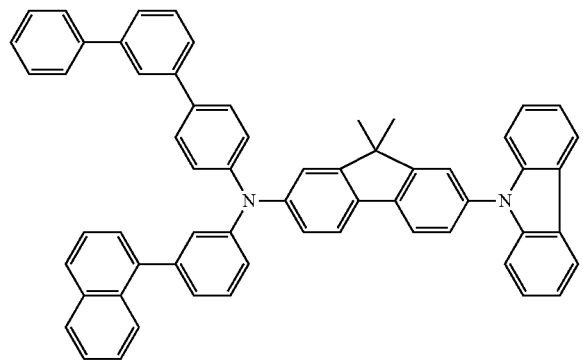
[C-4]
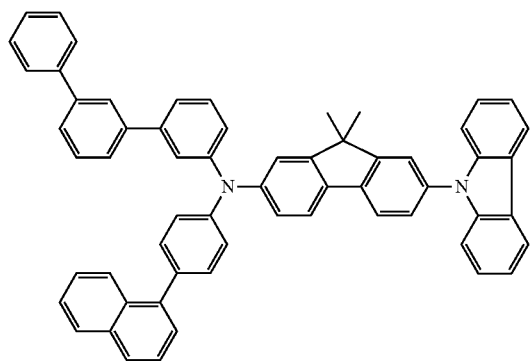
[C-5]
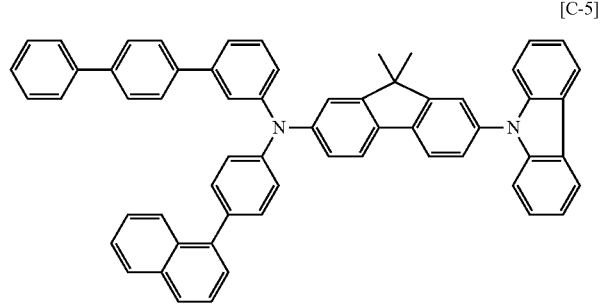
[C-6]
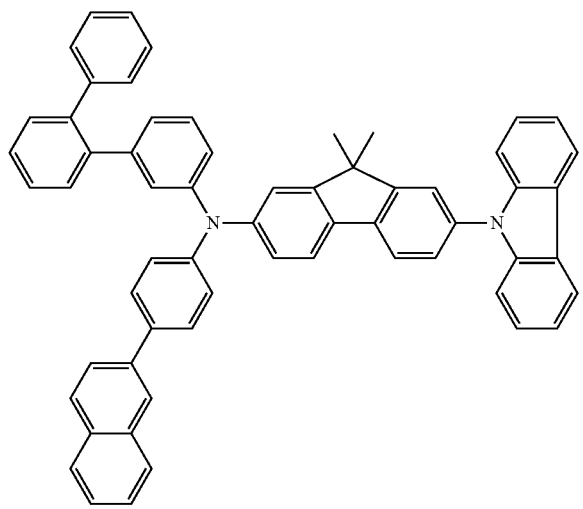
[C-7]
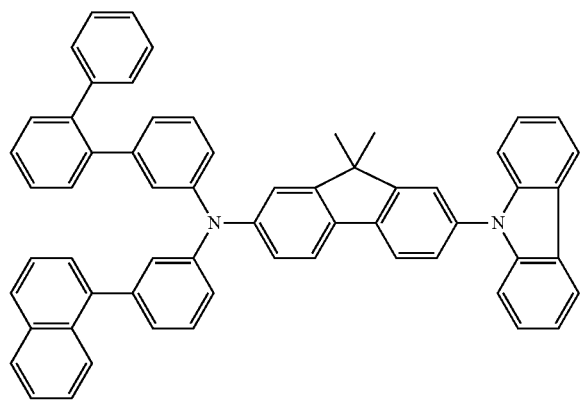

-continued
[C-8]
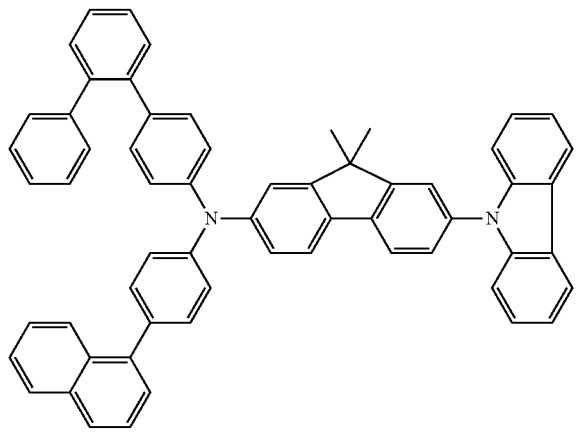
[C-9]
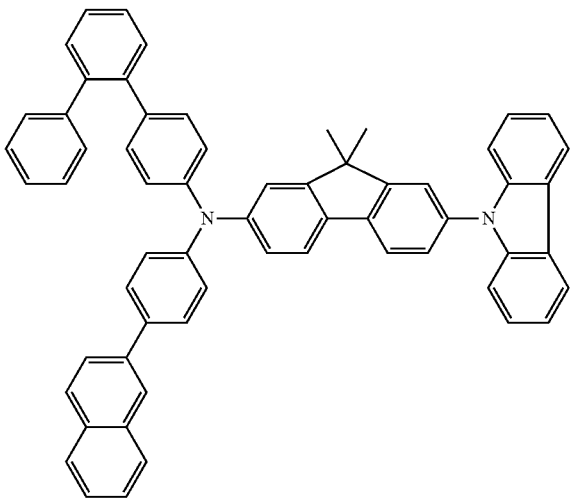
[C-10]
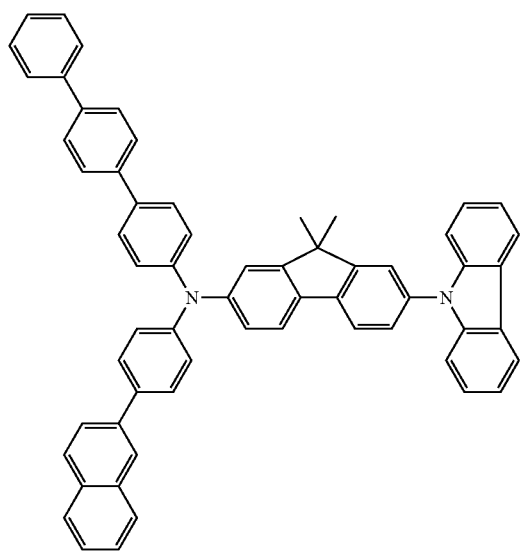
[C-11]
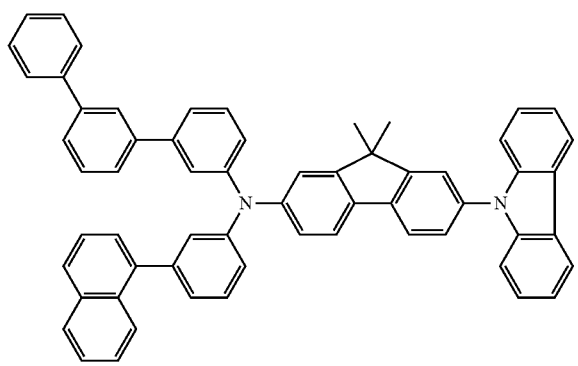
[C-12]
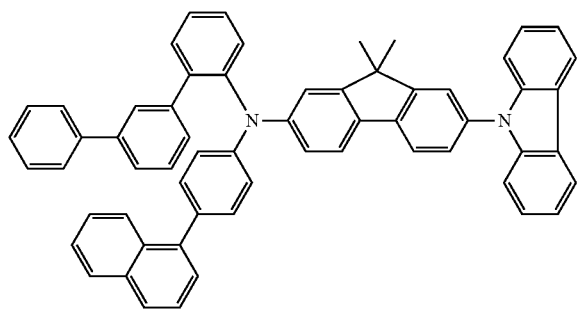
[C-13]
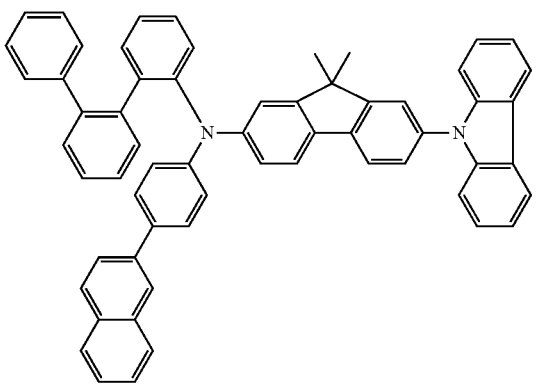

-continued
[C-14]
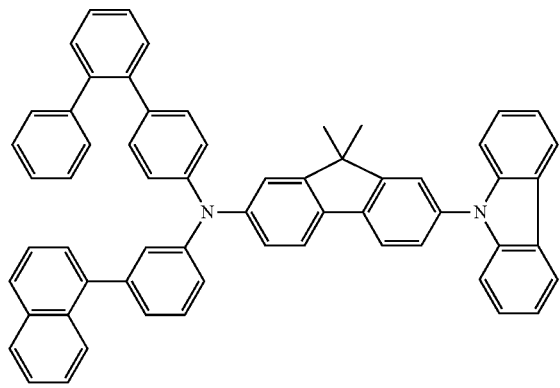
[C-15]
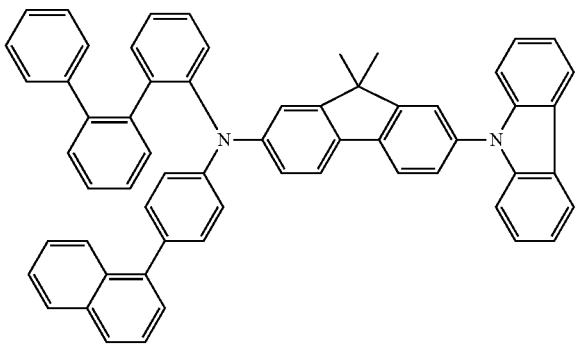
[C-16]
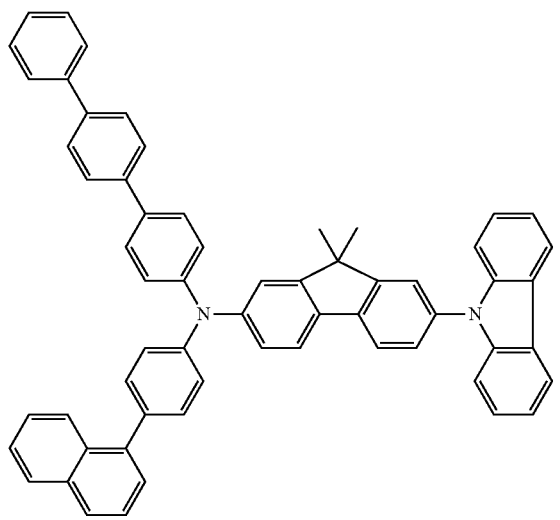
[C-17]
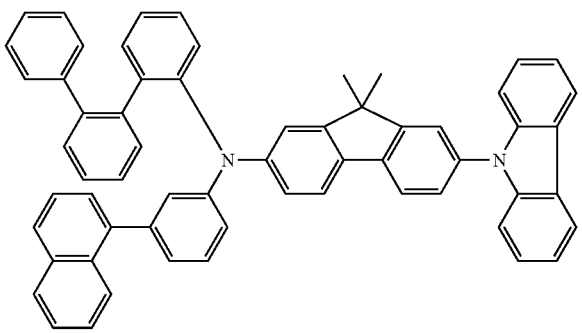
[C-18]
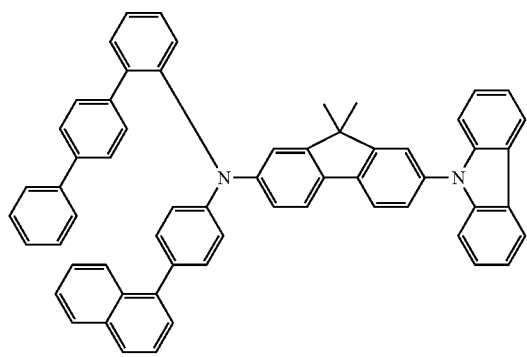
[C-19]
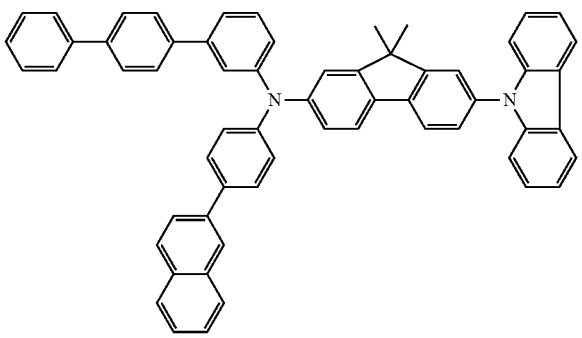

-continued
[C-20]
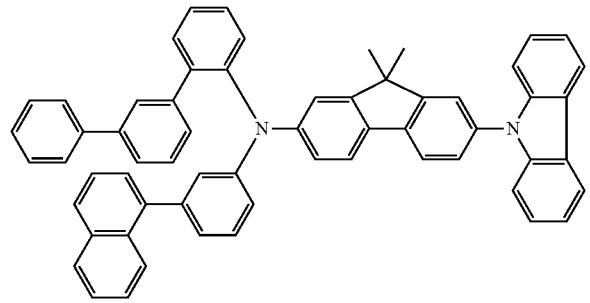
[C-21]
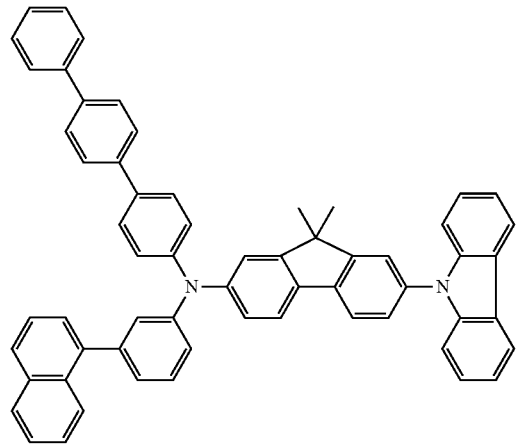
[C-22]
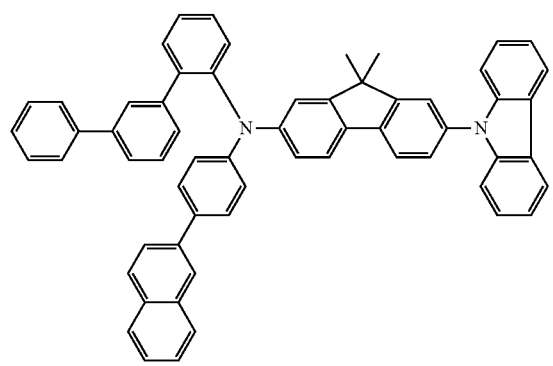
[C-23]
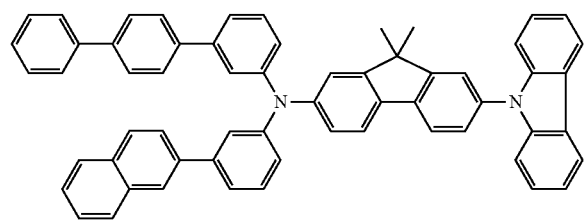
[C-24]
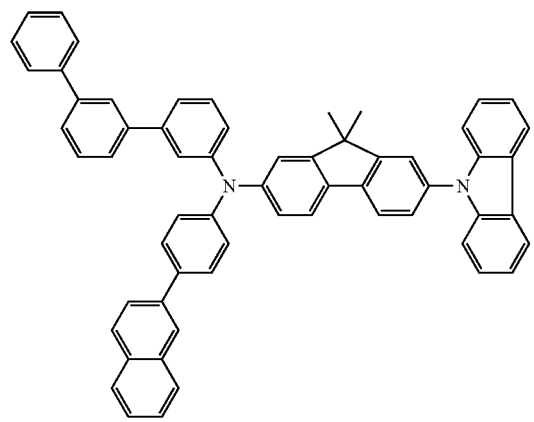
[C-25]
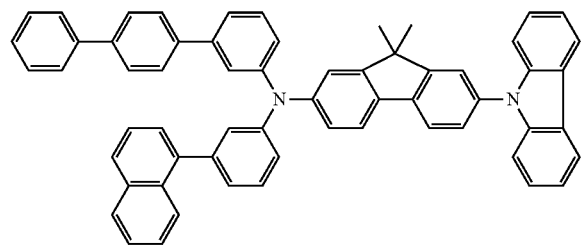
[C-26]
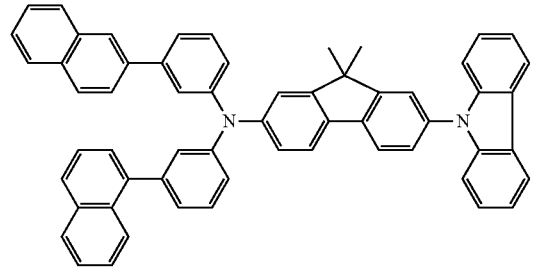
[C-27]
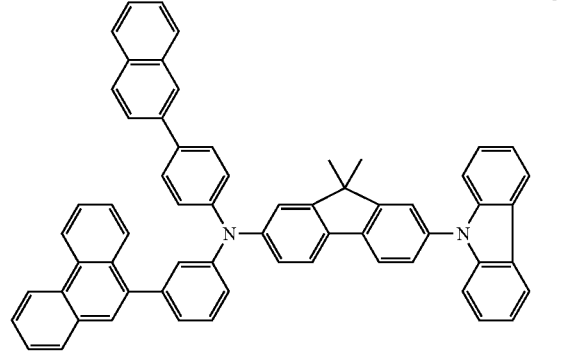

-continued
[C-28] [C-29]
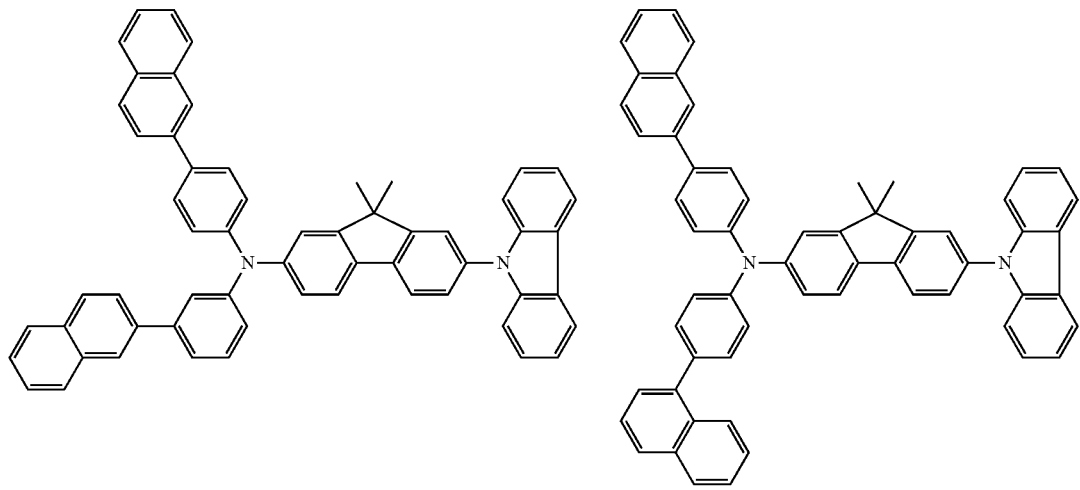
[C-30] [C-31]
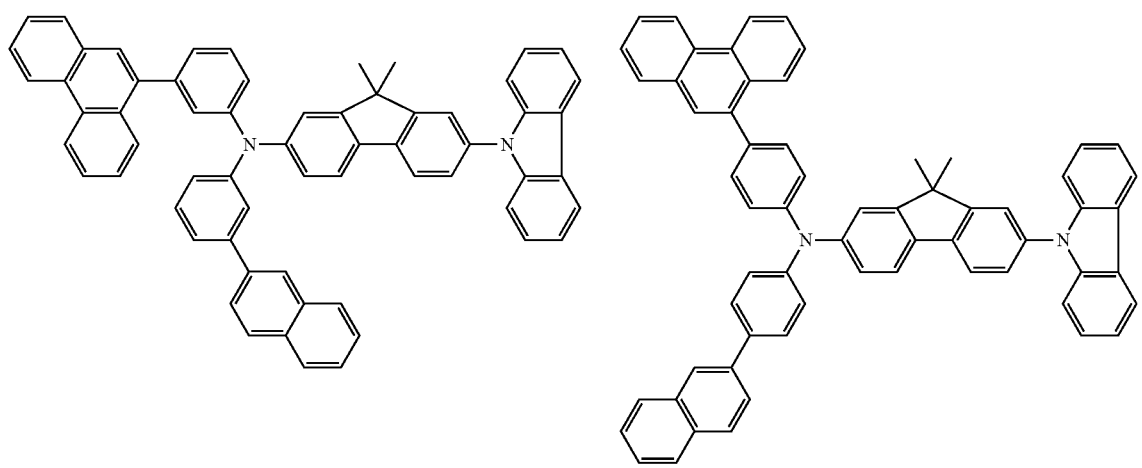
[C-32] [C-33]
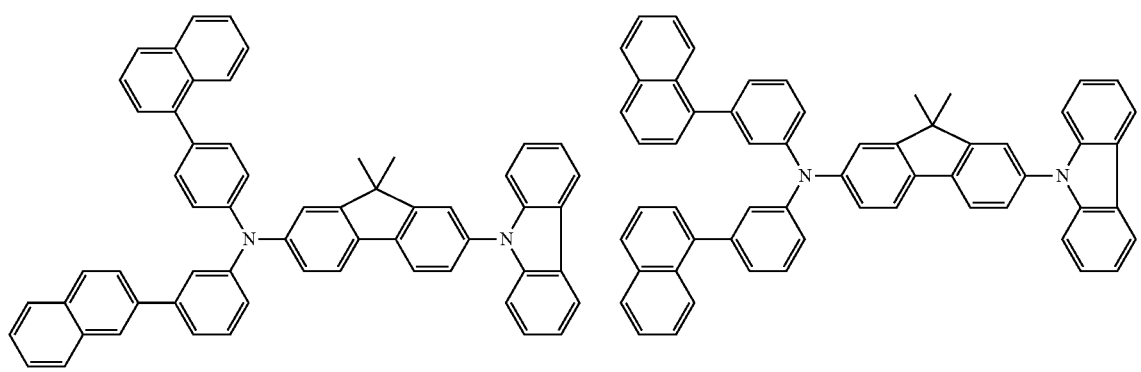

-continued
[C-34]
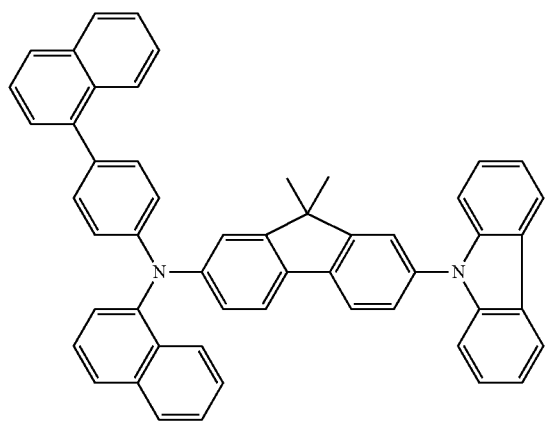
[C-35]
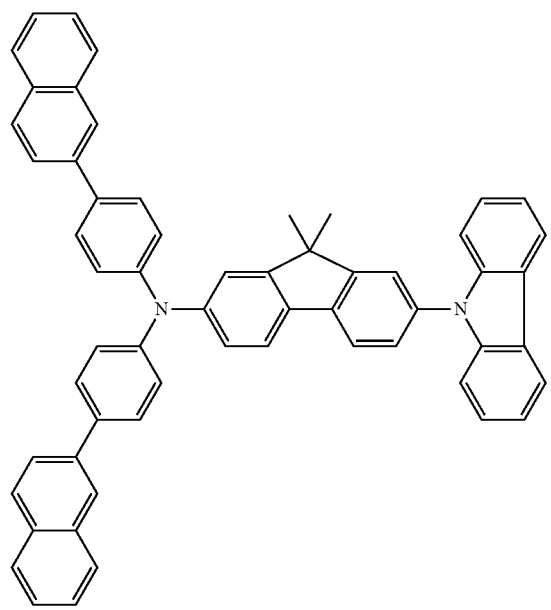
[C-36]
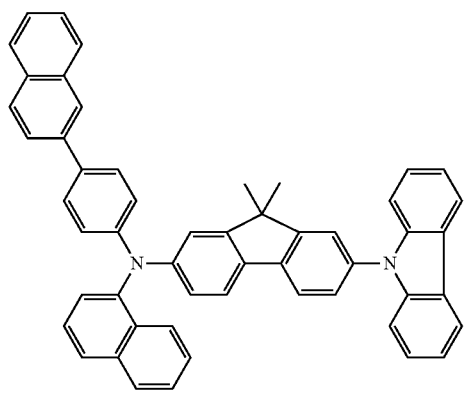
[C-37]
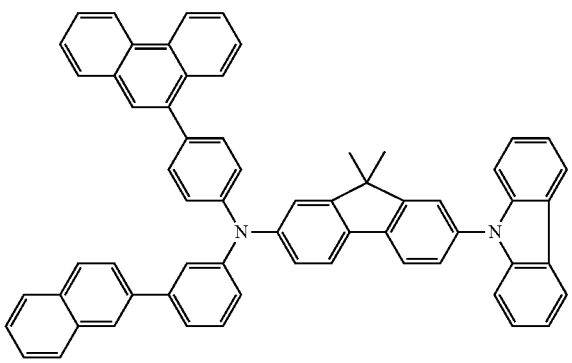
[C-38]
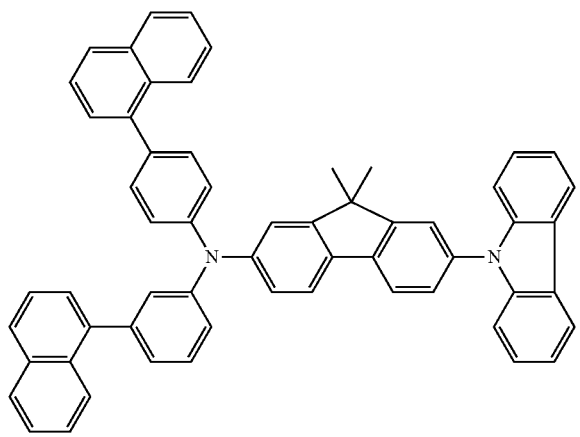
[C-39]
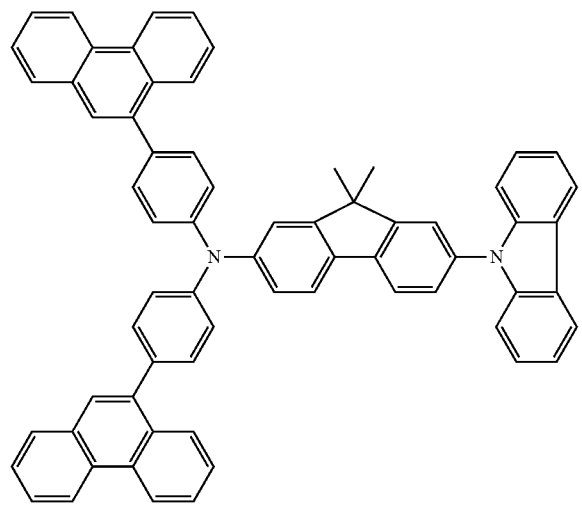

-continued
[C-40]
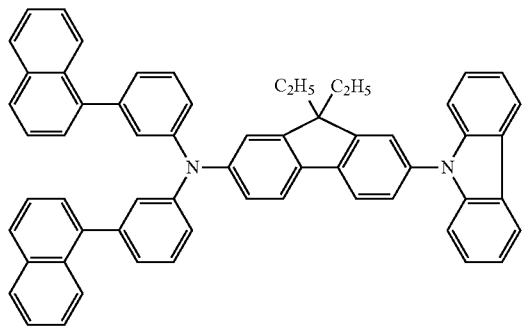
[C-41]
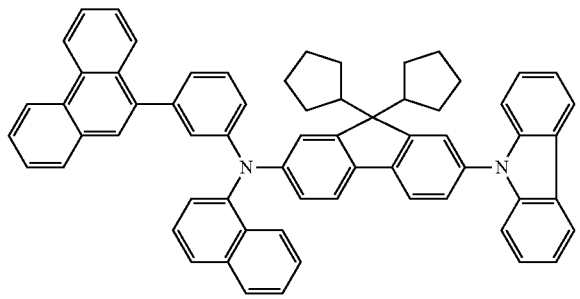
[C-42]
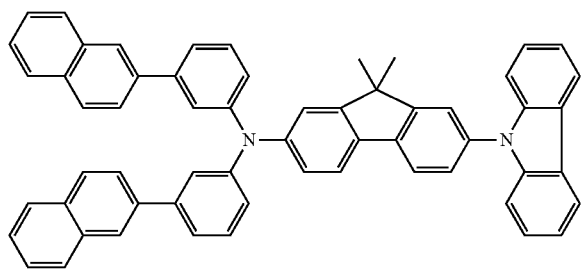
[C-43]
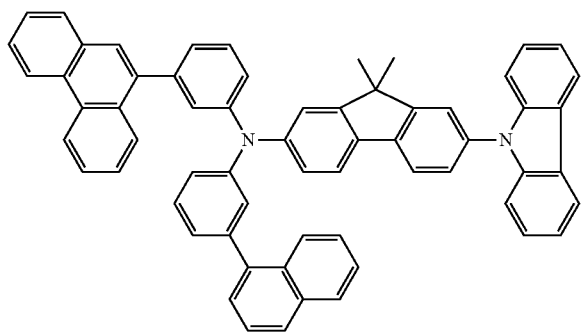
[C-44]
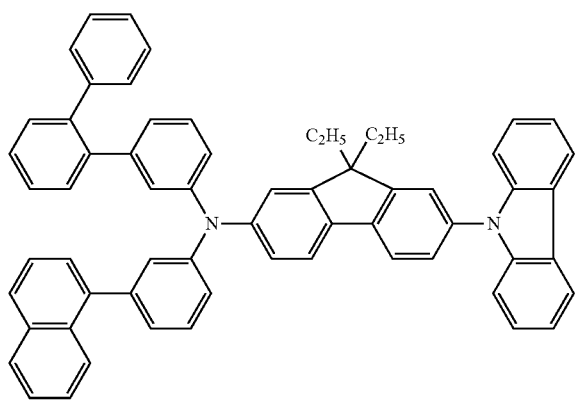
[C-45]
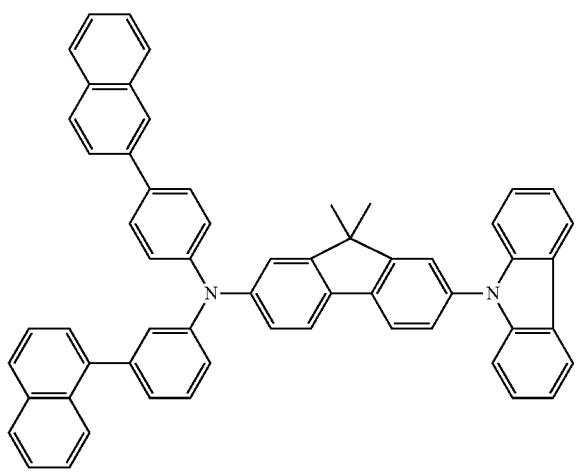

-continued
[C-46]
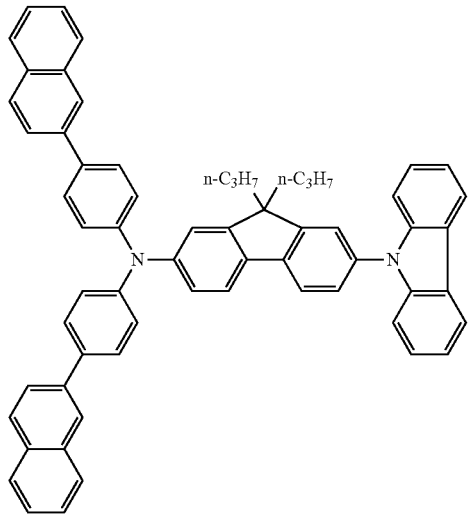
[C-47]
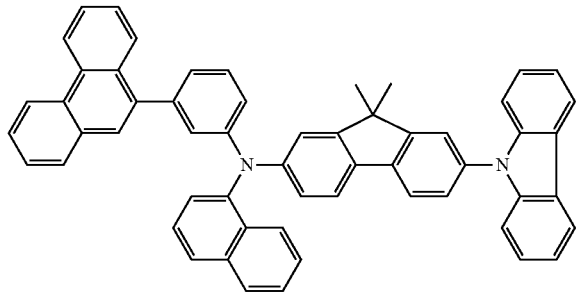
[C-48]
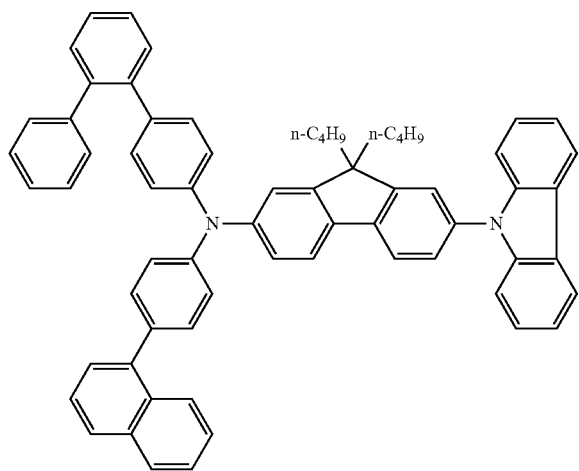
[C-49]
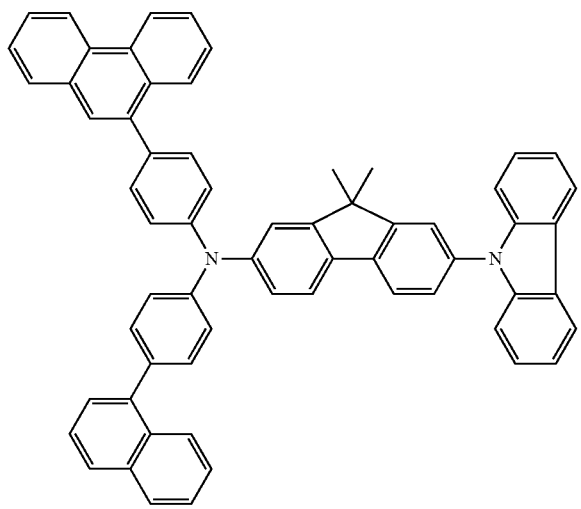
[C-50]
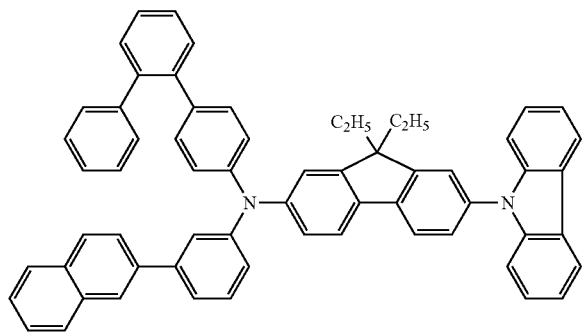
[D-1]
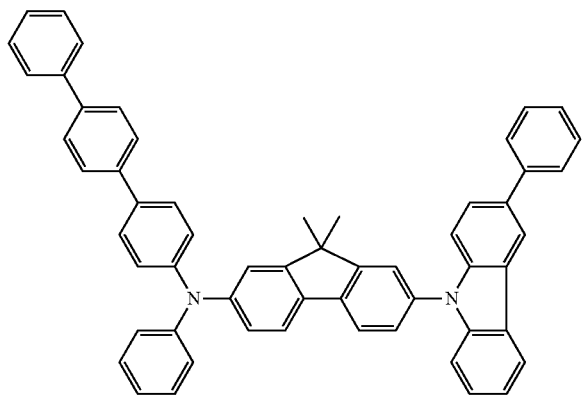

-continued
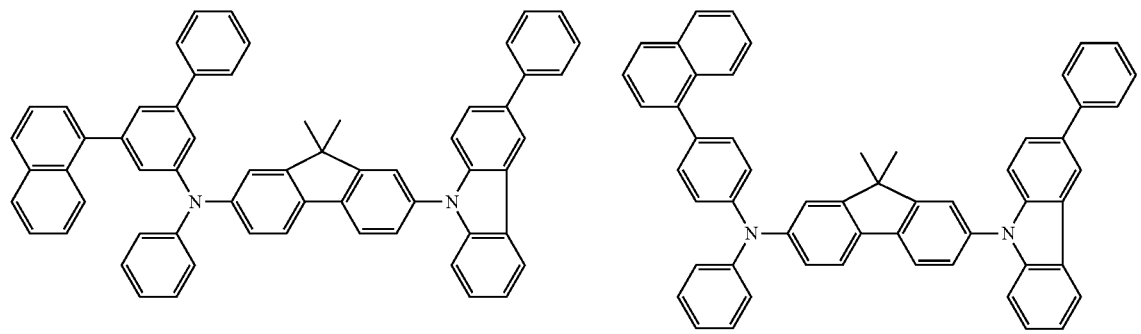
[D-2]
[D-3]
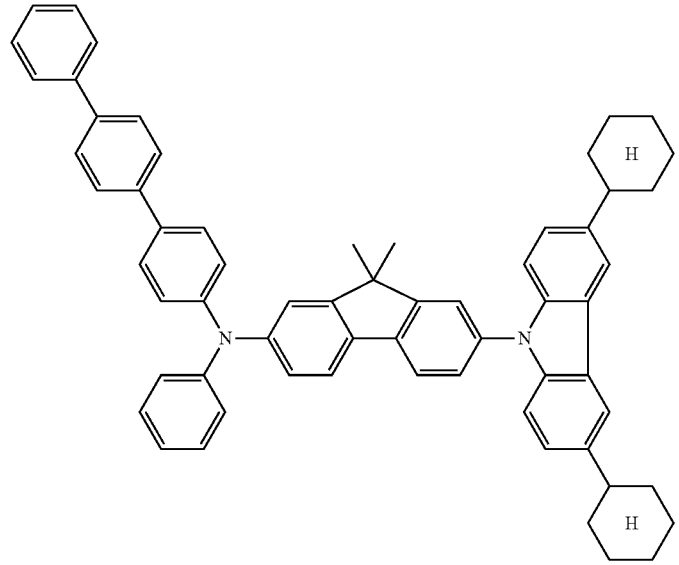
[D-4]
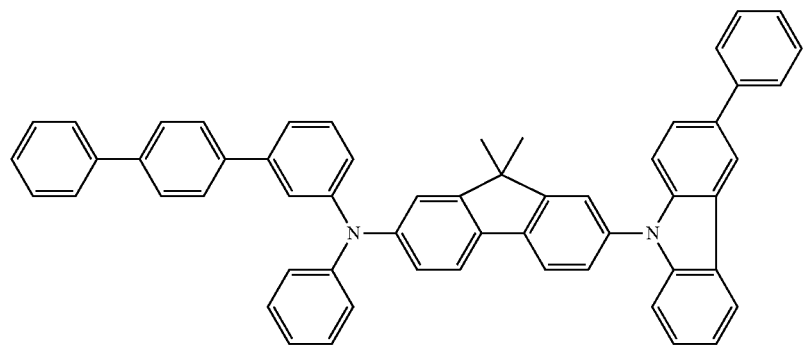
[D-5]
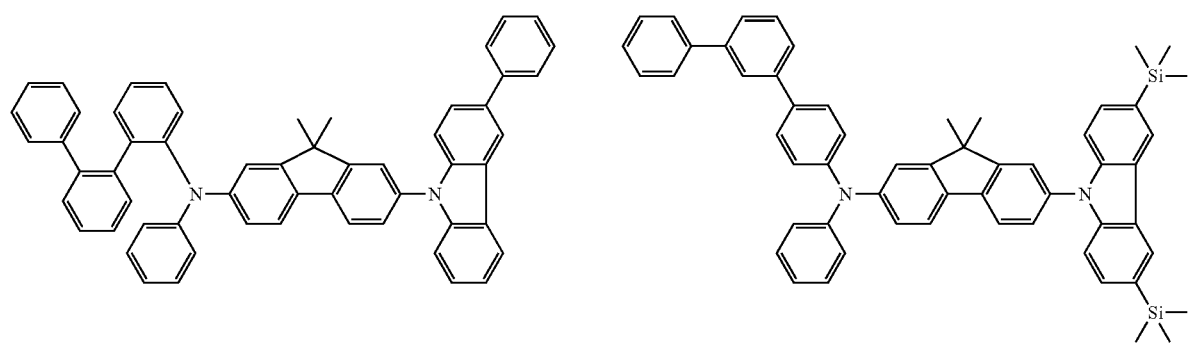
[D-6]
[D-7]

-continued
[D-8]
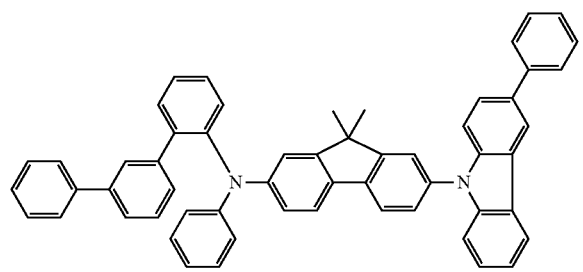
[D-9]
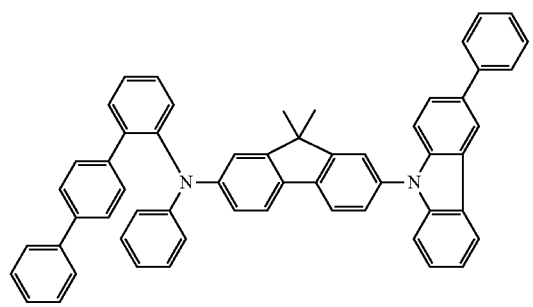
[D-10]
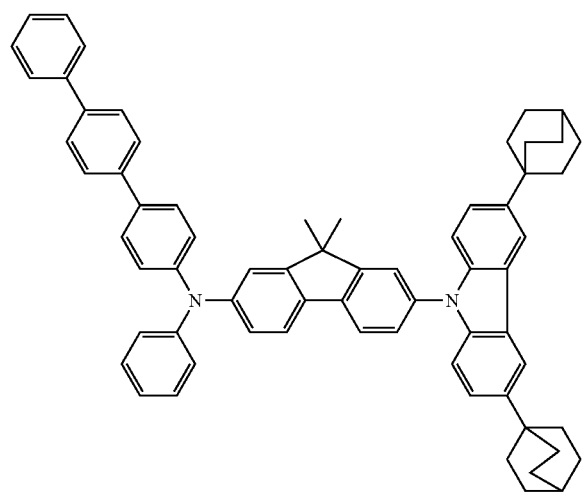
[D-11]
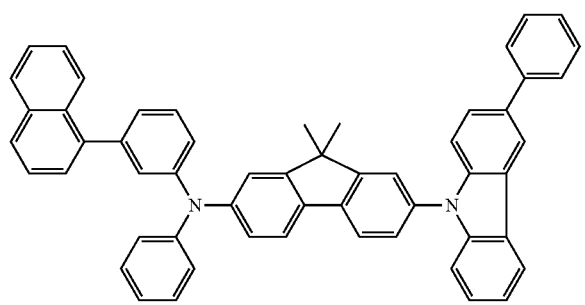
[D-12]
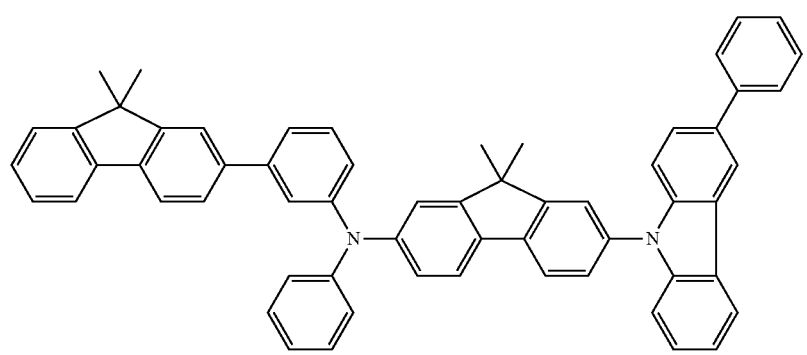
[D-13]
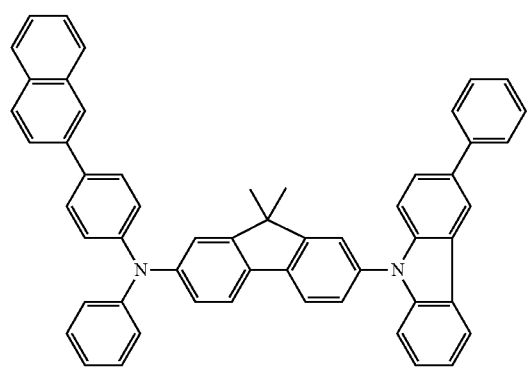
[D-14]
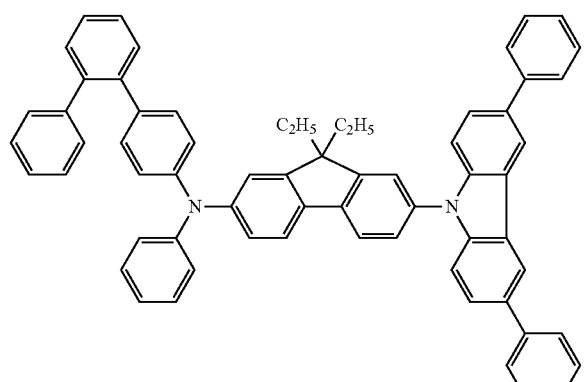

-continued
[D-15]
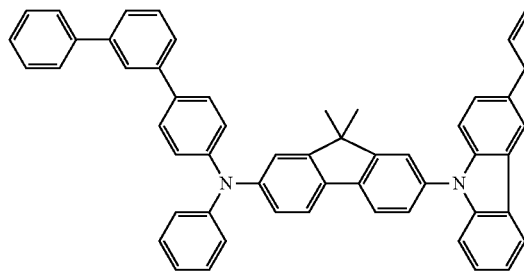
[D-16]
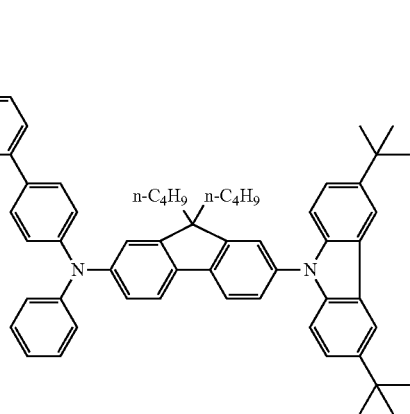
[D-17]
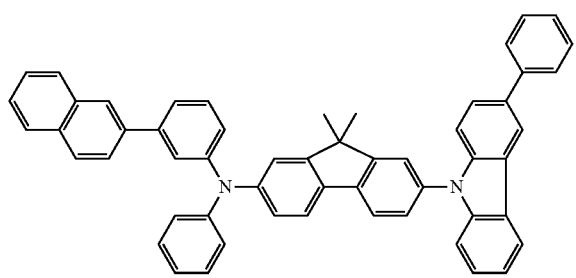
[D-18]
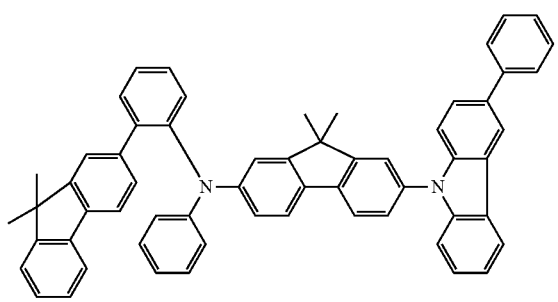
[D-19]
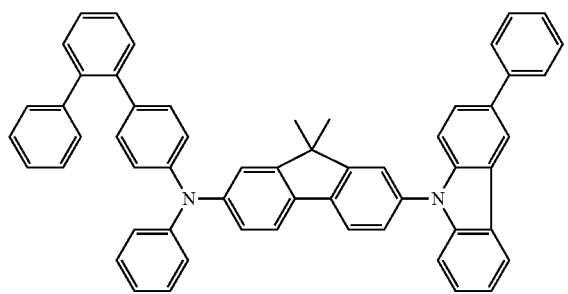
[D-20]
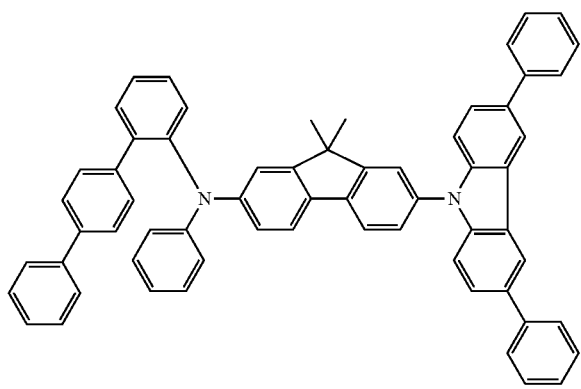
[D-21]
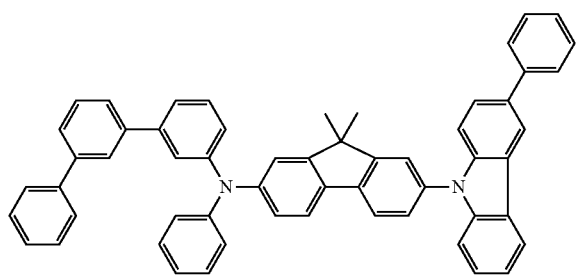
[D-22]
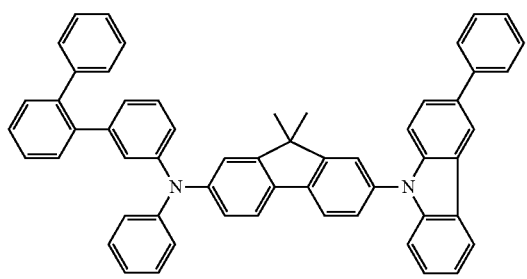

-continued
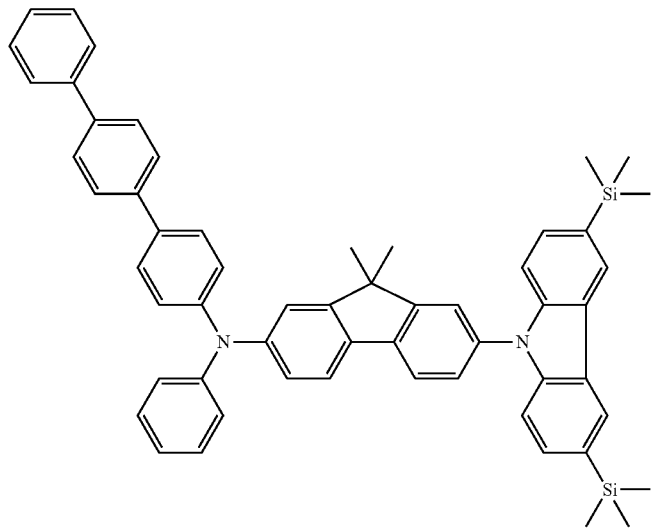
[D-23]
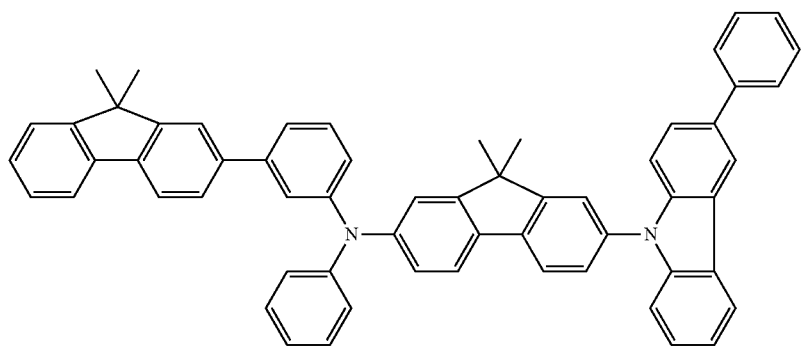
[D-24]
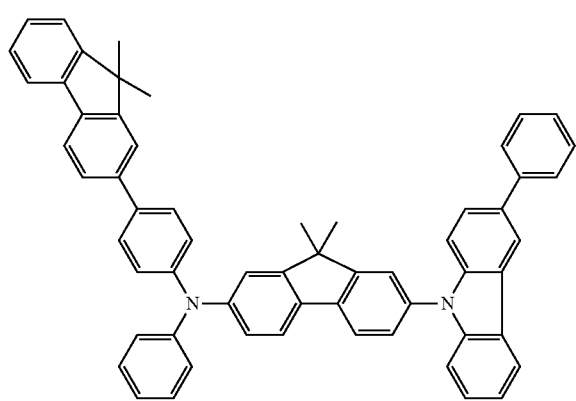
[D-25]
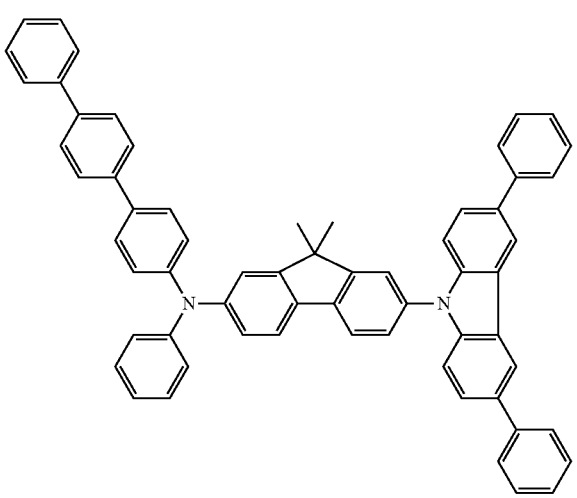
[D-26]

-continued
[D-27] [D-28]
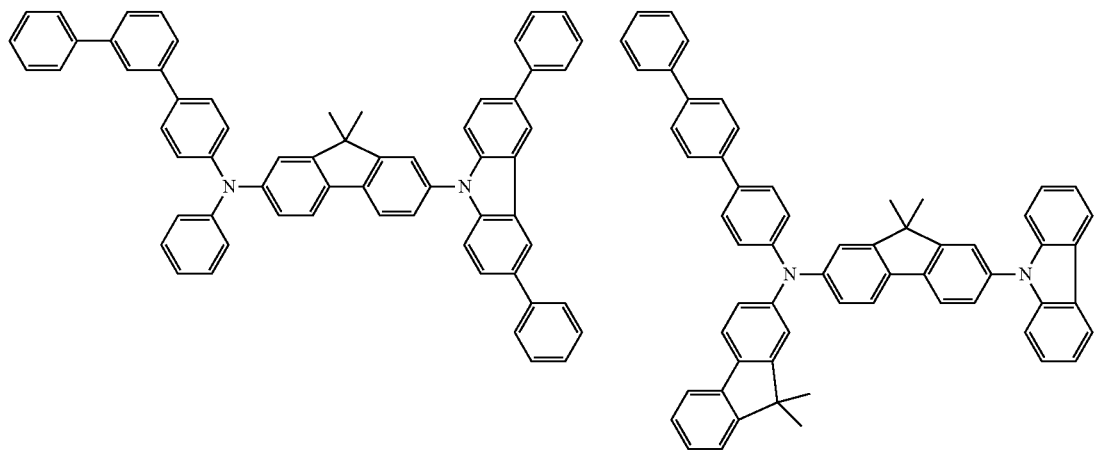
[D-29] [D-30]
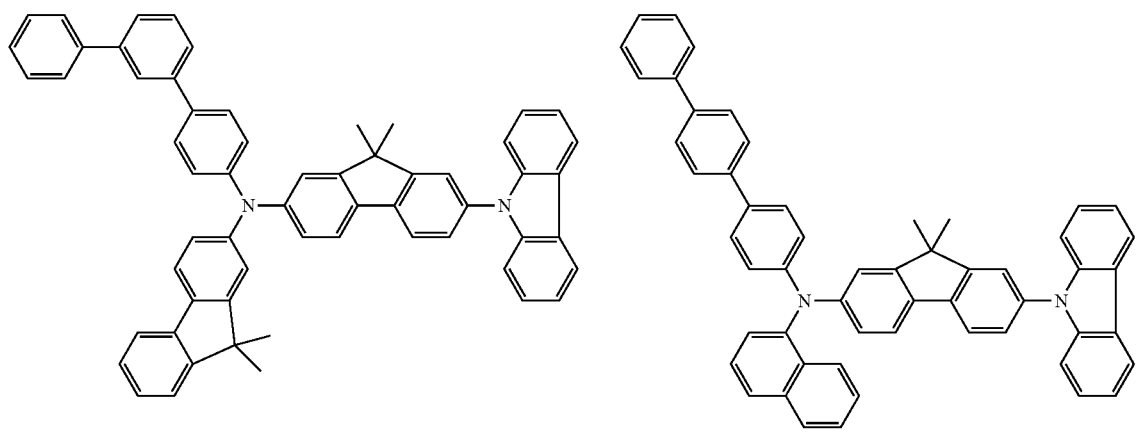
[D-31] [D-32]
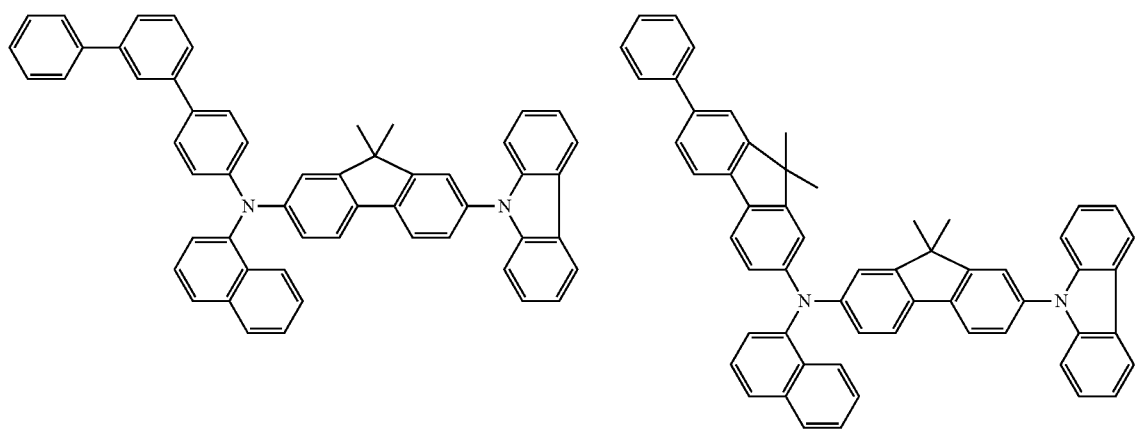

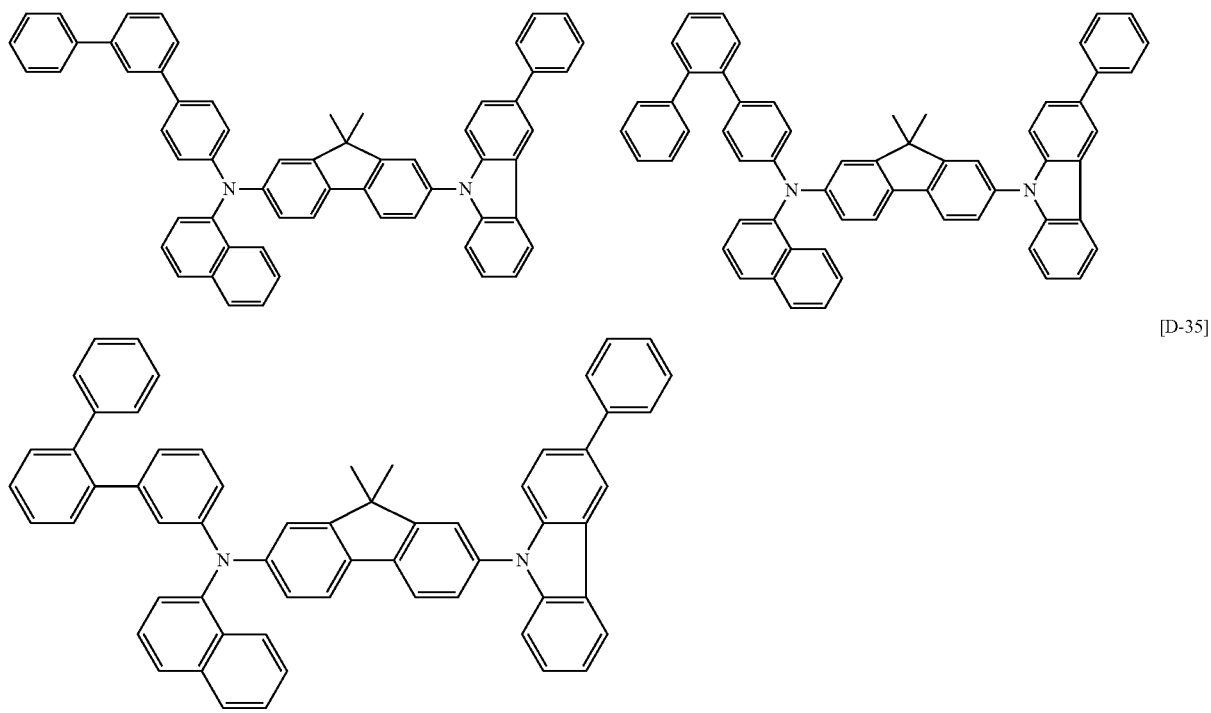

[D-33]

[D-34]

[D-35]

An aromatic amine derivative of the present invention represented by general formula (1) can be produced with a known process: For example, a 2,7-dihalogenofluorene derivative (e.g., 2,7-diiodo-9,9-dialkyl-9H-flurorene, 2-bromo-7-iodo-9,9-dialkyl-9H-fluororene, or 2-chloro-7-iodo-9,9-dialkyl-9H-fluororene) is reacted with a substituted or unsubstituted carbazole to produce a compound represented by general formula (1-A), after which it is reacted with a compound represented by general formula (2-A) to produce an aromatic amine derivative represented by general formula (1).

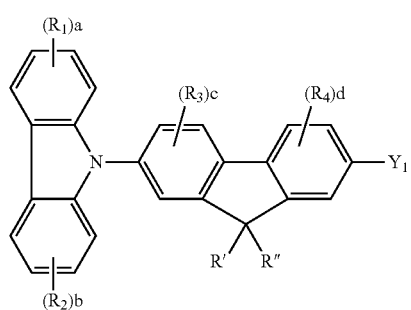

(1-A)

In general formula (1-A), Y represents a halogen atom, and $R_1$ to $R_4$, R', R" and a to d are defined the same as those in general formula (1).

(2-A)

In general formula (2-A), $Ar_1$ and $Ar_2$ are defined the same as those in general formula (1).

An aromatic amine derivative represented by general formula (1) can also be produced by reacting a 2,7-dihalogenofluorene derivative (e.g., 2,7-diiodo-9,9-dialkyl-9H-fluororene, 2-bromo-7-iodo-9,9-dialkyl-9H-fluororene, or 2-chloro-7-iodo-9,9-dialkyl-9H-fluororene) with a compound represented by general formula (2-A) to produce a compound represented by general formula (1-B), and reacting it with a substituted or unsubstituted carbazole.

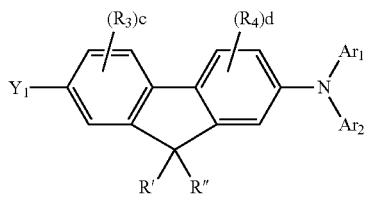

(1-B)

In general formula (1-B), $Y_1$ represents a halogen atom, and $R_3$, $R_4$, R', R", $Ar_1$ and $Ar_2$ are defined the same as those in general formula (1).

The reaction between the 2,7-dihalogenofluorene derivative and substituted or unsubstituted carbazole or compound represented by general formula (2-A) can be effected under the presence of, for example, a palladium catalyst (e.g., palladium acetate/tri-t-butyl phosphine, tris(dibenzylideneacetone)dipalladium/dicyclohexylphenylphosphine, or tris(dibenzylideneacetone)dipalladium/di(t-butyl)-2-biphenylphosphine) and a base (e.g., potassium carbonate, sodium carbonate, cesium carbonate, sodium t-butoxide, or potassium t-butoxide). The reaction can also be effected under the presence of a copper catalyst (e.g., copper powder, copper chloride or copper bromide) and a base (e.g., sodium carbonate or potassium carbonate).

The aromatic amine derivatives of the present invention represented by general formula (1) are suitably used as materials for organic EL devices. An organic electroluminescent device of the present invention includes one or more organic thin layers, including an emitting layer, interposed between the anode and cathode, wherein at least one of the organic thin layers contains any of the aromatic amine derivatives represented by general formula (1). In the organic EL device it is preferable that the hole injection layer or hole transport layer contains the aromatic amine derivative represented by general formula (1).

The following describes the structure of an organic EL device of the present invention. Representative structures of the organic EL device can be given below:
(1) anode/emitting layer/cathode
(2) anode/hole injection layer/emitting layer/cathode
(3) anode/emitting layer/electron injection layer/cathode
(4) anode/hole injection layer/emitting layer/electron injection layer/cathode
(5) anode/organic semiconductor layer/emitting layer/cathode
(6) anode/organic semiconductor layer/electron blocking layer/emitting layer/cathode
(7) anode/organic semiconductor layer/emitting layer/adhesion improving layer/cathode
(8) anode/hole injection layer/hole transport layer/emitting layer/electron injection layer/cathode
(9) anode/insulation layer/emitting layer/insulation layer/cathode
(10) anode/inorganic semiconductor layer/insulation layer/emitting layer/insulation layer/cathode
(11) anode/organic semiconductor layer/insulation layer/emitting layer/insulation layer/cathode
(12) anode/insulation layer/hole injection layer/hole transport layer/emitting layer/insulation layer/cathode
(13) anode/insulation layer/hole injection layer/hole transport layer/emitting layer/electron injection layer/cathode The representative examples of the configuration of the organic EL device are not limited to the above. Among them, the configuration (8) is preferable.

In the organic EL device of the present invention, an aromatic amine derivative of the present invention represented by general formula (1) may be contained in any of the above-described organic thin layers; however, it is contained preferably in a layer of the light-emitting region of these layers, most preferably in the hole injection layer and/or hole transport layer. The amount of the aromatic amine derivative added is 30 to 100 mol % of the layer.

Aromatic amine derivatives of the present invention are suitably used as the materials of hole injection layer or hole transport layer.

The hole injection layer and hole transport layer help holes to be injected into the emitting layer and transport them to the light-emitting region, and exhibit high hole mobility and low ionization energy, typically 5.5 eV or less. As the materials for such hole injection layer and hole transport layer, it is preferable to employ materials that transport holes to the emitting layer with lower field intensity. Further, the materials preferably have a hole mobility of at least $10^{-4}$ cm$^2$/Vs with an applied electrical field of, for example, $10^4$ to $10^6$ V/cm.

Aromatic amine derivatives of the present invention are suitable as hole transport materials not only because of their low ionization energy and high hole mobility, but also because of their less susceptibility to the substrate washing or the like in the manufacturing process for the presence of polar groups that impart good adhesion to the anode. These factors are considered to contribute to the prolonging of the life of organic EL devices manufactured using aromatic amine derivatives of the present invention.

The hole injection layer or hole transport layer can be prepared by forming a thin film of aromatic amine derivative of the present invention by means of vacuum vapor deposition, spin coating, casting, LB method or other known technique. There are no particular limitations on the thickness of the hole injection layer or hole transport layer; it is generally 5 nm to 5 μm.

As long as the hole transport region contains the aromatic amine derivative of the present invention, the hole injection layer and hole transport layer may be a single layer containing one or more of the above aromatic amine derivatives, or may be a multilayer-stack obtained by stacking a hole injection layer and hole a transport layer which contain different aromatic amine derivatives.

An organic semiconductor layer helps holes or electrons to be injected into the emitting layer, and preferably has a conductivity of $10^{-10}$ S/cm or higher. Examples of materials that can be used for organic semiconductor layer include conductive oligomers such as thiophene-containing oligomer and arylamine-containing oligomer, and conductive dendrimers such as arylamine dendrimer.

Organic EL devices are generally formed on a light-transmitting substrate, a substrate for supporting thereon organic EL devices. Its light-transmitting property is preferably such that visible light transmittance at 400-700 nm is 50% or more. Further, the light-transmitting substrate is preferably flat and smooth.

Preferable examples of light-transmitting substrate include glass plates and synthetic resin plates. Examples of glass plates include, inter alia, soda-lime glass plate, barium-strontium glass plate, lead glass plate, aluminosilicate glass plate, borosilicate glass plate, barium borosilicate glass plate, and silica glass plate. Examples of synthetic resin plates include polycarbonate resin plate, acrylic resin plate, polyethylene terephthalate resin plate, polyethersulfide resin plate, and polysulfone resin plate.

The anode has a function of injecting holes into the hole transport layer or emitting layer, which is effective at a work function of 4.5 eV or more. Specific examples of anode materials used in the present include indium tin oxide (ITO), a mixture of indium oxide and zinc oxide (IZO), a mixture of ITO and cerium oxide (ITCO), a mixture of IZO and cerium oxide (IZCO), a mixture of indium oxide and cerium oxide (ICO), a mixture of zinc oxide and aluminum oxide (AZO), tin oxide (NESA), gold, silver, platinum and copper.

The anode can be prepared by forming a thin layer of any of these electrode materials by vapor deposition, sputtering or the like.

In the case where light from the emitting layer is to be emitted from the anode side, the anode's light transmittance is preferably set greater than 10%. Moreover, the sheet resistance of the anode is preferably several hundred Ω/cm$^2$ or less. The thickness of the anode is typically 10 nm to 1 μm, preferably 10 to 200 nm, although it varies depending on the type of the anode material.

For the cathode, such a cathode is used that contains as an electrode substance a metal, alloy or conductive compound, or a mixture thereof, which have a small work function (e.g., 4 eV or less). Specific examples of electrode substances include sodium, sodium-potassium alloy, magnesium, lithium, cesium, magnesium/silver alloy, aluminum/aluminum oxide, $Al/Li_2O$, $Al/LiO$, $Al/LiF$, aluminum/lithium alloy, indium, and rare earth metals.

The cathode can be prepared by forming a thin layer of any of these electrode materials by vapor deposition, sputtering or the like.

In the case where light from the emitting layer is to be emitted from the cathode side, the cathode's light transmittance is preferably set greater than 10%. Moreover, the sheet resistance of the cathode is preferably several hundred $\Omega/cm^2$ or less. The thickness of the cathode is typically 10 nm to 1 μm, preferably 50 to 200 nm.

Generally, since an electric field is applied to ultrathin films in an organic EL device, pixel defects are likely to occur due to leakage or short circuit. To avoid this, an insulating thin layer may be inserted between the pair of electrodes. Examples of materials used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or multilayer-stack thereof may be used.

The emitting layer of the organic EL device of the present invention has the following the functions:

(i) Injection function: Holes from the anode or hole injection layer and electrons from the cathode or electron injection layer are injected in the emitting layer upon application of an electric field;

(ii) Transportation function: The injected charges (electrons and holes) are allowed to migrate in the emitting layer by the force of an electric field; and (iii) Light emission function: The electrons and holes are recombined in the emitting layer to effect light emission.

Examples of methods of forming the emitting layer include such known methods as vapor deposition, spin coating and LB method. It is preferable that the emitting layer be a molecular deposition film. The molecular deposition film refers to a film formed by deposition of a gaseous source compound, or a film formed by solidification of a source compound in the form of solution or in liquid phase. The molecular deposition film is usually distinguished from a thin film formed using the LB method (molecular accumulation film) by the difference in aggregation structure or higher order structure, or the difference in function due to the differences in structure.

The emitting layer may also be formed by dissolving a binder such as resin and a source compound in a solvent to obtain a solution, and forming a thin film from the solution by spin coating or the like.

In the present invention, the emitting layer may contain light-emitting materials composed of pyrene derivative and amine compound, or other known metal complexes.

A preferable metal complex is one in which at least one metal selected from Ir, Ru, Pd, Pt, Os and Re is contained. The ligand preferably has at least one skeleton selected from phenypyridine skeleton, bipyridyl skeleton, and phenanthroline skeleton.

Specific examples of such metal complexes include, but not limited to, tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, platinum octaethyl porphine, platinum octaphenyl porphine, palladium octaethyl porphine, and palladium octaphenyl porphine. These compounds can be appropriately selected according to the required light color, the device performance, and the type of host compound.

The emitting layer of the organic EL device may contain a phosphorescent dopant and/or a fluorescent dopant.

A phosphorescent dopant is a compound that can emit light from triplet excitons. The dopant is not limited so long as it can emit from triplet excitions, and it is preferably a metal complex containing at least one metal selected from the group consisting of Ir, Ru, Pd, Pt, Os and Re. A porphyrin metal complex or ortho-metalated metal complex is preferable. As the porphyrin metal complex, a porphyrin platinum complex is preferable. These phosphorescent dopants may be used alone or in combination.

There are various types of ligands that form an ortho-metalated metal complex. Preferable ligands include 2-phenylpyridine, 7,8-benzoquinoline, 2-(2-thienyl)pyridine, 2-(1-naphthyl)pyridine and 2-phenylquinoline derivatives. These ligands may have a substituent as needed. The above derivatives with fluorine, or the derivatives with trifluoromethyl groups are particularly preferable as blue dopants. As an auxiliary ligand, other ligands than the above-mentioned ligands, such as acetylacetonate and picric acid may be employed.

The amount of a phosphorescent dopant in the emitting layer is not limited and can be appropriately selected according to the intended purposes; it is, for example, 0.1 to 70 mass %, preferably 1 to 30 mass %. A phosphorescent dopant content of less than mass 0.1 mass % may result in weak light emission, and therefore, the effect of adding phosphorescent dopant may not be sufficiently obtained. When the content exceeds 70 mass %, on the other hand, a phenomenon called concentration quenching may significantly proceed, degrading the device performance.

The thickness of the emitting layer is preferably 5 to 50 nm, more preferably 7 to 50 nm, most preferably 10 to 50 nm. Formation of an emitting layer having a thickness of less than 5 nm is difficult, which in turn makes it difficult to control color degree, and when the thickness exceeds 50 nm, it may elevate driving voltage.

As for the fluorescent dopant, it is preferably selected from amine-based compounds, aromatic compounds, chelate complexes such as tris(8-quinolilate)aluminum complexes, coumarin derivatives, tetraphenylbutadiene derivatives, bisstyrylarylene derivatives, oxadiazole derivatives and, according to the required light colors. In particular, arylamine compounds and aryldiamine compounds are preferable, with styrylamine compounds, styryldiamine compounds, aromatic amine compounds and aromatic diamine compounds being more preferably, and fused polycyclic amine derivatives being further preferable. These fluorescent dopants may be used alone or in combination.

In the organic EL device of the present invention, the emitting layer preferably contains an styrylamine and/or arylamine as a fluorescent dopant. The styrylamine and/or arylamine represented by the following general formula (10) are preferable.

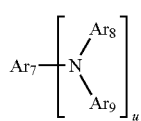

In general formula (10), $Ar_7$ to $Ar_9$ represent a substituted or unsubstituted aromatic group having 6 to 40 ring carbon atoms; and u represents an integer of 1 to 4, preferably an integer of 1 to 2. Any one of $Ar_7$ to $Ar_9$ may be a group having a styryl group. When any one of $Ar_7$ and $Ar_8$ has a styryl group, at least one of $Ar_8$ and $Ar_9$ is preferably substituted by a styryl group.

Examples of aromatic groups having 6 to 40 ring carbon atoms include phenyl group, naphthyl group, anthranyl group, phenanthryl group, pyreny group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group, stilbene group, perylenyl group, chrysenyl group, pycenyl group, triphenylenyl group, rubicenyl group, benzoanthracenyl group, phenylanthracenyl group, bisanthracenyl group, and arylenen groups represented by the following general formulas (C) and (D). Among them, naphthyl group, anthranyl group, chrysenyl group, pyrenyl group, and arylene groups represented by general formula (D) are preferable.

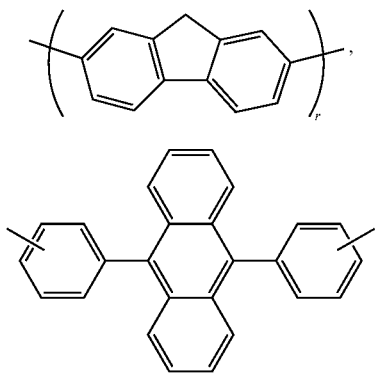

In general formula (C), r represents an integer of 1 to 3.

Preferable examples of substituents to be attached to the aryl groups and arylene groups include $C_{1-6}$ alkyl groups (e.g., ethyl group, methyl group, i-propyl group, n-propyl group, s-butyl group, t-butyl group, pentyl group, hexyl group, cyclopentyl group and cyclohexyl group), $C_{1-6}$ alkoxy groups (e.g., ethoxy group, methoxy group, i-propoxy group, n-propoxy group, s-butoxy group, t-butoxy group, pentoxy group, hexyloxy group, cyclopentoxy group and cyclohexyloxy group), $C_{5-40}$ aryl groups, amino groups substituted by $C_{5-40}$ aryl groups, esters having $C_{5-40}$ aryl groups, esters having $C_{1-6}$ alkyl groups, cyano group, nitro group, and halogen atoms.

There are no particular limitations on the light-emitting materials to be contained in the emitting layer; as host materials, examples include polycyclic aromatic compounds such as anthracene compounds, phenanthrene compounds, fluoranthene compounds, tetracene compounds, triphenylene compounds, chrysene compounds, pyrene compounds, coronene compounds, perylene compounds, phthaloperylene compounds, naphthaloperylene compounds, naphthalene compounds and pentacene compounds; oxadiazole, bisbenzoxazoline, bisstyryl, cyclopentadiene, quinoline metal complexes, tris(8-hydroxyquinolinato)aluminum complex, tris (4-methylquinolinato)aluminum complex, tris(5-phenyl-8-quinolinato)aluminum complex, aminoquinoline metal complexes, benzoquinoline metal complexes, tri-(p-terphenyl-4-il)amine, 1-aryl-2,5-di(2-thienyl)pyrrole derivatives, pyrane, quinacridone, rubrene, distyrylbenzene derivatives, distyrylarylene derivatives, porphyrin derivatives, stilbene derivatives, pyrazoline derivatives, coumarin dyes, pyran dyes, phthalocyanine dyes, naphthalocyanine dyes, croconium dyes, squarylium dyes, oxobenzanthracene dyes, fluorescein dyes, rhodamine dyes, pyrylium dyes, perylene dyes, stilbene dyes, polythiophene dyes, rare-earth complex fluorescence materials, rare-earth phosphorescent complexes (e.g., Ir complexes); and conductive polymer materials such as polyvinyl carbazole, polysilane, and polyethylene dioxythiophene (PEDOT). These compounds may be used alone or in combination.

Host materials to be combined with compounds of the present invention are preferably selected from those represented by the following general formulas (11) to (17).

Anthracene derivatives represented by the following general formula (11):

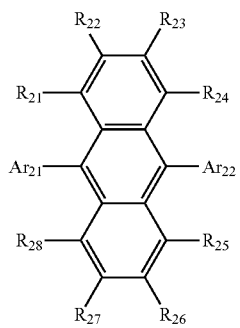

In general formula (11), $A_{21}$ and $A_{22}$ each independently represent a substituted or unsubstituted $C_{6-60}$ aromatic group; and $R_{21}$ to $R_{28}$ each independently represent a hydrogen atom, substituted or unsubstituted $C_{6-50}$ aromatic group, substituted or unsubstituted $C_{5-50}$ aromatic heterocyclic group, substituted or unsubstituted $C_{1-50}$ alkyl group, substituted or unsubstituted cycloalkyl group, substituted or unsubstituted $C_{1-50}$ alkoxy group, substituted or unsubstituted $C_{6-50}$ aralkyl group, substituted or unsubstituted $C_{5-50}$ aryloxy group, substituted or unsubstituted $C_{5-50}$ arylthio group, substituted or unsubstituted $C_{1-50}$ alkoxycarbonyl group, substituted or unsubstituted silyl group, carboxyl group, halogen atom, cyano group, nitro group, or hydroxyl group.

Pyrene derivatives represented by the following general formula (12):

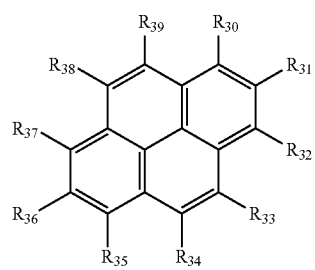

(12)

In general formula (12), $R_{30}$ to $R_{39}$ each independently represent a hydrogen atom, substituted or unsubstituted $C_{6-50}$ aromatic group, substituted or unsubstituted $C_{5-50}$ aromatic heterocyclic group, substituted or unsubstituted $C_{1-50}$ alkyl group, substituted or unsubstituted cycloalkyl group, substituted or unsubstituted $C_{1-50}$ alkoxy group, substituted or unsubstituted $C_{6-50}$ aralkyl group, substituted or unsubstituted $C_{5-50}$ aryloxy group, substituted or unsubstituted $C_{5-50}$ arylthio group, substituted or unsubstituted $C_{1-50}$ alkoxycarbonyl group, substituted or unsubstituted silyl group, carboxyl group, halogen atom, cyano group, nitro group, or hydroxyl group.

Anthracene derivatives represented by the following general formula (13):

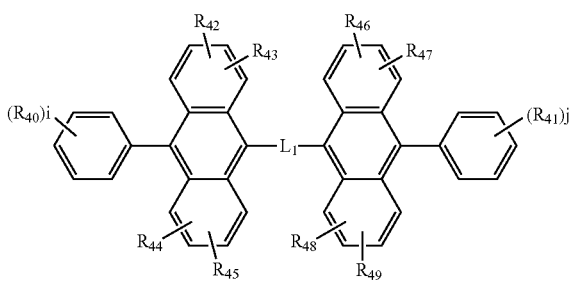

(13)

In general formula (13), $R_{40}$ to $R_{49}$ each independently represent a hydrogen atom, alkyl group, cycloalkyl group, substituted or unsubstituted aryl group, alkoxyl group, aryloxy group, alkylamino group, alkenyl group, arylamino group, or substituted or unsubstituted heterocyclic group;

i and j each independently represent an integer of 1 to 5, and when i or j represents an integer of 2 or larger, $R_{40}$s or $R_{41}$s may be the same or different, and $R_{40}$s or $R_{41}$s may be joined together to form a ring;

$R_{42}$ and $R_{43}$, $R_{44}$ and $R_{45}$, $R_{46}$ and $R_{47}$, and $R_{48}$ and $R_{49}$ may be joined together to form a ring; and $L_1$ represents a single bond, —O—, —S—, —N(R)— (where R is an alkyl group or a substituted or unsubstituted aryl group), alkylene group, or arylene group.

Anthracene derivatives represented by the following general formula (14):

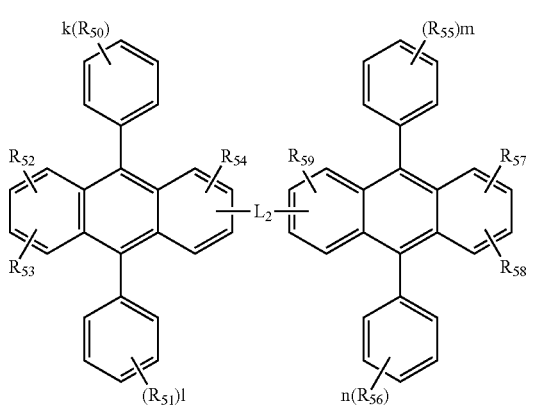

(14)

In general formula (14), $R_{50}$ to $R_{59}$ each independently represent a hydrogen atom, alkyl group, cycloalkyl group, aryl group, alkoxyl group, aryloxy group, alkylamino group, arylamino group, or substituted or unsubstituted heterocyclic group;

k, l, m and n each independently represent an integer of 1 to 5, and when k, l, m or n represents an integer of 2 or larger, $R_{50}$s, $R_{51}$s, $R_{55}$s or $R_{56}$s may be the same or different, and $R_{50}$s, $R_{51}$s, $R_{55}$s or $R_{56}$s may be joined together to form a ring;

$R_{52}$ and $R_{53}$, and $R_{57}$ and $R_{58}$ may be joined together to form a ring; and $L_2$ represents a single bond, —O—, —S—, —N(R)— (where R is an alkyl group or a substituted or unsubstituted aryl group), alkylene group, or arylene group.

Spirofluorene derivatives represented by the following general formula (15):

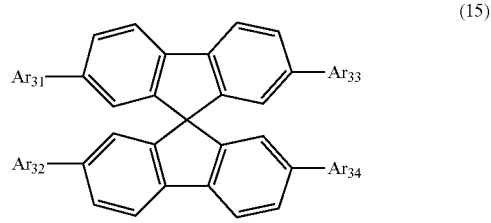

(15)

In general formula (15), $Ar_{31}$ to $Ar_{34}$ each independently represents a substituted or unsubstituted biphenyl group or a substituted or unsubstituted naphthyl group.

Compounds represented by the following general formula (16):

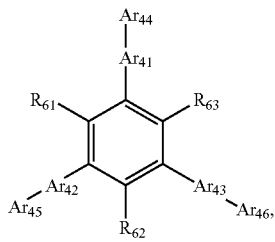

In general formula (16), $Ar_{41}$ to $Ar_{43}$ each independently represents a substituted or unsubstituted $C_{6-60}$ arylene group; $Ar_{44}$ to $Ar_{46}$ each independently represents a hydrogen atom or a substituted or unsubstituted $C_{6-60}$ aryl group; and $R_{61}$ to $R_{63}$ each independently represents a hydrogen atom, $C_{1-6}$ alkyl group, $C_{3-6}$ cycloalkyl group, $C_{1-6}$ alkoxyl group, $C_{5-18}$ aryloxy group, $C_{7-18}$ aralkyloxy group, $C_{5-16}$ arylamino group, nitro group, cyano group, $C_{1-6}$ ester group, or halogen atom.

Fluorene compounds represented by the following general formula (17):

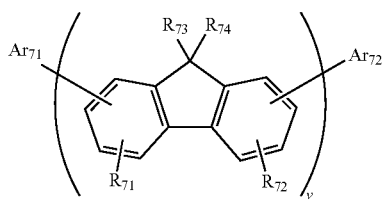

In general formula (17), $R_{71}$ and $R_{72}$ represent a hydrogen atom, substituted or unsubstituted alkyl group, substituted or unsubstituted aralkyl group, substituted or unsubstituted aryl group, substituted or unsubstituted heterocyclic group, substituted amino group, cyano group, or halogen atom; $R_{71}$s bonding to different fluorene groups may be the same or different, $R_{72}$s bonding to different fluorene groups may be the same or different, and $R_{71}$ and $R_{72}$ bonding to the same fluorene group may be the same or different;

$R_{73}$ and $R_{74}$ represent a hydrogen atom, substituted or unsubstituted alkyl group, substituted or unsubstituted aralkyl group, substituted or unsubstituted aryl group, or substituted or unsubstituted heterocyclic group; $R_{73}$s bonding to different fluorene groups may be the same or different, $R_{74}$s bonding to different fluorene groups may be the same or different, and $R_{73}$ and $R_{74}$ bonding to the same fluorene group may be the same or different;

$Ar_{71}$ and $Ar_{72}$, which may be the same or different, represent a substituted or unsubstituted condensed polycyclic aromatic group having 3 or more benzene rings, or a substituted or unsubstituted condensed polycyclic heterocyclic group having 3 or more benzene rings and heterocyclic rings in total and bonding to the fluorene group via a carbon atom; and v represents an integer of 1 to 10.

Of these host materials, anthracene derivatives are preferable, with monoanthracene derivatives being more preferable, and asymmetric anthracene being most preferable.

A compound having a carbazole ring, which is a host suitable for phosphorescence emission, is a compound that allows a phosphorescent compound to emit light as a result of energy transfer from its excited state to the phosphorescent compound. A host compound is not limited as long as it can transfer its excited energy to a phosphorescent compound, and it can be appropriately selected depending on the intended purpose. In addition to the carbazole ring, the compound may have an optional heterocyclic ring or the like.

Specific examples of such host compounds include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene compounds, porphyrin compounds, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, anhydrides of heterocyclic tetracarboxylic having a structure such as naphthalene and perylene, phthalocyanine derivatives, metal complexes of 8-quinolinol derivatives, various metal complexes represented by metal complexes having metalphthalocyanine, benzoxazole or benzothiazole as a ligand, electroconductive high-molecular-weight oligomers such as polysilane compounds, poly(N-vinylcarbazole) derivatives, aniline copolymers, thiophene oligomers and polythiophene, and high-molecular-weight compounds such as polythiophene derivatives, polyphenylene derivatives, polyphenylenevinyfene derivatives and polyfluorene derivatives. The host compound may be used alone or in combination.

Specific compounds shown below can be exemplified.

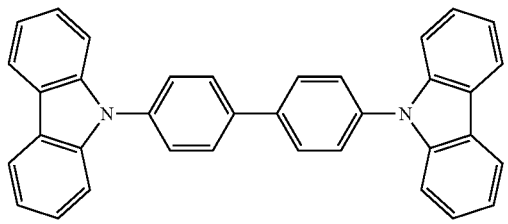

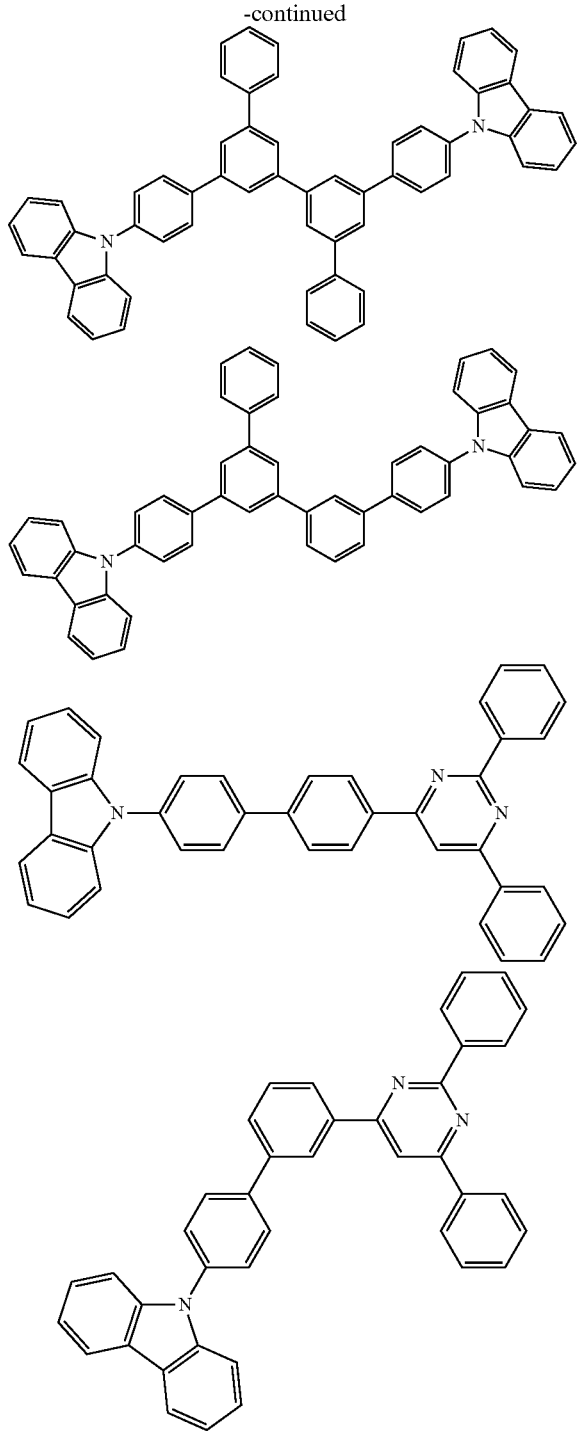

The electron injection layer and electron transport layer help electrons to be injected into the emitting layer and transport them to the light-emitting region, and exhibit high electron mobility. The adhesion improving layer is a part of the electron injection layer which is made of material exhibiting particularly good adhesion to the cathode.

In an organic EL device some of emitted light is reflected by the electrode (cathode, in this case). It is thus known that the light reflected from the cathode interferes with light that directly travels to the outside through the anode. To maximize the effect of light interference, the thickness of the electron transport layer is set to several nanometers to several micrometers. In particular, when the electron transporting layer is thick, its electron mobility is preferably $10^{-5}$ cm$^2$/Vs or more at an applied electric field of $10^4$ to $10^6$ V/cm in order to prevent unwanted voltage increase.

The material used for the electron injection layer and electron transport layer is preferably a metal complex of 8-hydroxyquinoline or a derivative thereof, or an oxadiazole derivative. Specific examples of the metal complex of 8-hydroxyquinoline or derivative thereof include metal chelate oxynoid compounds containing a chelate of oxine (generally, 8-quinolinol or 8-hydroxyquinoline), e.g. tris(8-quinolinolato)aluminum.

As examples of the oxadiazole derivative, electron transport compounds represented by the following formulas can be given.

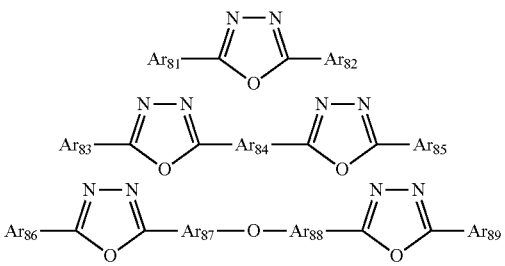

In the formulas $Ar_{81}$, $Ar_{82}$, $Ar_{83}$, $Ar_{85}$, $Ar_{86}$ and $Ar_{89}$, which may be the same or different, represent a substituted or unsubstituted aryl group; and $Ar_{84}$, $Ar_{87}$ and $Ar_{88}$, which may be the same or different, represent a substituted or unsubstituted arylene group.

Examples of aryl groups include phenyl group, biphenyl group, anthranyl group, perylenyl group, and pyrenyl group. Examples of arylene groups include phenylene group, naphthylene group, biphenylene group, anthranylene group, perylenylene group, pyrenylene group. Examples of substituents include $C_{1-10}$ alkyl groups, $C_{1-10}$ alkoxy groups and cyano group. The electron-transporting compound is preferably one from which a thin film can be formed.

The hole injection layer and hole transport layer help holes to be injected into the emitting layer and transport them to the light-emitting region, and exhibit high hole mobility and low ionization energy, typically 5.5 eV or less.

As the materials for such hole injection layer and hole transport layer, it is preferable to employ materials that transport holes to the emitting layer with lower field intensity. Further, the materials preferably have a hole mobility of at least $10^{-4}$ cm$^2$/Vs with an applied electrical field of, for example, $10^4$ to $10^6$ V/cm.

In the case where an aromatic amine derivative of the present invention is contained in a layer of the hole injection transport region, the aromatic amine derivative may be used either singly or in combination with other material when forming the hole injection or hole transport layer.

There are no particular limitations on the materials for hole injection layer and hole transport layer to be mixed with aromatic amine derivatives of the present invention as long as the materials exhibit the above-described preferable properties; any desired material can be selected from materials that have been widely used as hole transport materials for photoconductive members, or selected from known materials used for hole injection layer and hole transport layer of organic EL device. As used herein, a material that has a hole transport capability and can be used in the hole transport region is referred to as a hole transport material.

Aromatic amine derivatives to be used in the hole injection layer and hole transport layer include the compounds represented by the following general formula:

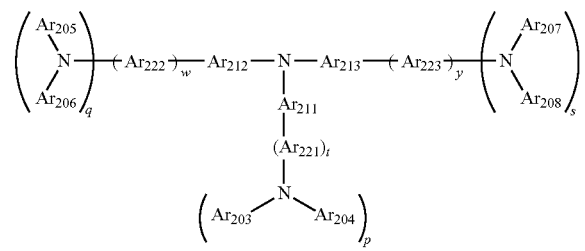

In the general formula, $Ar_{211}$ to $Ar_{213}$, $Ar_{221}$ to $Ar_{223}$ and $Ar_{203}$ to $Ar_{208}$ each independently represent a substituted or unsubstituted $C_{6-50}$ aromatic hydrocarbon group or a substituted or unsubstituted $C_{5-50}$ aromatic heterocyclic group; p, q, s, t, w and y each independently represent an integer of 0 to 3.

Specific examples of substituted or unsubstituted $C_{6-50}$ aromatic hydrocarbon groups include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4''-t-butyl-p-terphenyl-4-yl.

Specific examples of substituted or unsubstituted $C_{5-50}$ aromatic heterocyclic groups include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuryl group, 3-benzofuryl group, 4-benzofuryl group, 5-benzofuryl group, 6-benzofuryl group, 7-benzofuryl group, 1-isobenzofuryl group, 3-isobenzofuryl group, 4-isobenzofuryl group, 5-isobenzofuryl group, 6-isobenzofuryl group, 7-isobenzofuryl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Further, the compounds represented by the following formula can be used in the hole injection layer and hole transport layer.

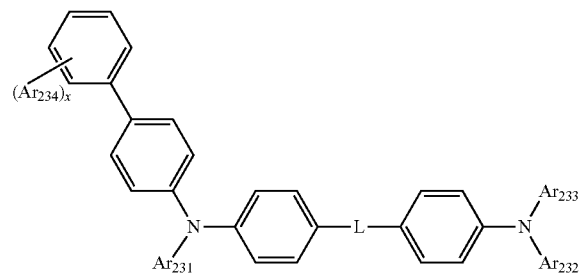

In the general formula, $Ar_{231}$ to $Ar_{234}$ each independently represent a substituted or unsubstituted $C_{6-50}$ aromatic hydrocarbon group, or a substituted or unsubstituted $C_{5-50}$ aromatic heterocyclic group; L represents a linking group, which is a single bond, a substituted or unsubstituted $C_{6-50}$ aromatic hydrocarbon group, or a substituted or unsubstituted $C_{5-50}$ aromatic heterocyclic group; and x represents an integer of 0 to 5.

As specific examples of the substituted or unsubstituted $C_{6-50}$ aromatic hydrocarbon groups and substituted or unsubstituted $C_{5-50}$ aromatic heterocyclic group, the same as those exemplified above can be exemplified.

Specific examples of materials for the hole injection layer and hole transport layer include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and conductive high-molecular oligomers (in particular, thiophene oligomer).

Although the above materials can be employed for the hole injection layer and hole-transporting layer, it is preferable to employ a porphyrin compound, aromatic tertiary amine compound or styrylamine compound, particularly preferably an aromatic tertiary amine compound.

It is also preferable to employ a compound having two fused aromatic rings in the molecule, such as 4,4'-bis(N-(1-naphthyl)-N-phenylamino)biphenyl (hereinafter "NPD"), or 4,4',4"-tris(N-(3-methylphenyl)-N-phenylamino)triphenylamine (hereinafter "MTDATA") wherein three triphenylamine units are linked in a star-burst form.

In addition to the above, nitrogenous heterocyclic derivatives represented by the following formula can also be employed.

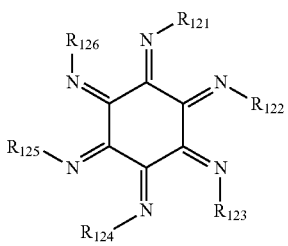

In the formula $R_{121}$ to $R_{126}$ each independently represents a substituted or unsubstituted alkyl group, substituted or unsubstituted aryl group, substituted or unsubstituted aralkyl group, substituted or unsubstituted heterocyclic group; $R_{121}$ to $R_{126}$ may be the same or different; and $R^{121}$ and $R^{122}$, $R^{123}$ and $R^{124}$, $R^{125}$ and $R^{126}$, $R^{121}$ and $R^{126}$, $R^{122}$ and $R^{123}$, and $R^{124}$ and $R^{125}$ may form a fused ring.

Further, the compounds represented by the following formula can also be employed.

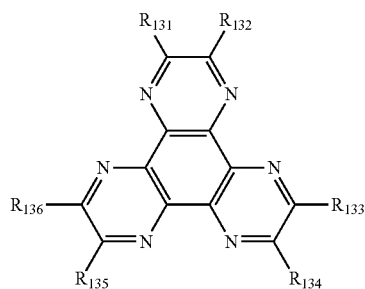

In the general formula $R_{131}$ to $R_{136}$ represent a substituent, preferably an electron-attracting group such as cyano group, nitro group, sulfonyl group, carbonyl group, trifluoromethyl group or halogen atom.

As represented by these materials, acceptor materials can also be used as hole injection material, specific examples of which are as described above.

Other than the above aromatic dimethylidene compounds described as the materials for emitting layer, inorganic compounds such as p-type Si and p-type SiC can also be used as the materials for hole injection layer and hole transport layer.

The hole injection layer and hole transport layer can be prepared by forming thin films of aromatic amine derivative of the present invention by means of vacuum vapor deposition, spin coating, casting, LB method or other known technique.

There are no particular limitations on the thickness of the hole injection layer and hole transport layer; the thickness is generally 5 nm to 5 μm. As long as the hole transport region contains the aromatic amine derivative of the present invention, the hole injection layer and hole transport layer may be a single layer containing one or more of the above materials, or may be a multilayer-stack obtained by stacking a hole injection layer and a hole transport layer which contain different materials.

An organic semiconductor layer for helping holes to be injected into the emitting layer may be provided, and an organic semiconductor layer having an electric conductivity of $10^{-10}$ S/cm or more is preferable. As the materials for such an organic semiconductor layer, conductive oligomers such as thiophene-containing oligomers and arylamine-containing oligomers, and conductive dendrimers such as arylamine-containing dendrimers may be employed.

Regarding the method of manufacturing an organic EL device of the present invention, the organic EL device can be manufactured by forming, in order, an anode, an emitting layer, a hole injection layer, an electron injection layer and a cathode, using the materials and the method described above. Manufacture of the organic EL device may also be effected in the opposite order—from cathode to anode.

Hereinafter, an example of manufacture of an organic EL device will be described, wherein an anode, a hole injection layer, an emitting layer, an electron injection layer, and a cathode are sequentially formed on a light-transmitting substrate.

First, an anode is formed on a suitable light-transmitting substrate by forming thereon a thin film of anode material by vapor deposition or sputtering, to a thickness of not greater than 1 μm, preferably within 10 to 200 nm.

Next, a hole injection layer is formed on the anode. As described above, vacuum vapor deposition, spin coating, casting, LB method, or other technique may be employed to form the hole injection layer. Among these techniques, vacuum vapor deposition is preferable because a homogenous film is easily obtained and because pinholes are less likely to occur.

In the case where the hole injection layer is formed by vacuum vapor deposition, the conditions for the deposition vary depending on the compound used (material for hole injection layer), desired crystal structure or recrystallizing structure of the hole injection layer, and so forth. In general, the conditions are preferably set such that deposition source temperature is within 50 to 450°, vacuum degree is within $10^{-7}$ to $10^{-3}$ Torr, deposition rate is within 0.01 to 50 nm/sec, substrate temperature is within −50 to 300° C., and film thickness is 5 nm to 5 μm.

Next, an emitting layer is formed on the hole injection layer. The emitting layer can similarly be provided by forming a thin film of light-emitting material by vacuum vapor deposition, sputtering, spin coating, casting or other technique. Vacuum vapor deposition is preferable because a homogenous film is easily obtained and because pinholes are less likely to occur.

In the case of where the emitting layer is formed by vacuum vapor deposition, conditions for the deposition, which vary depending on the compound used, can be generally selected from conditions similar to those for the hole injection layer. The film thickness is preferably 10 to 40 nm.

Next, an electron injection layer is formed on the emitting layer. Vacuum vapor deposition is preferable as in the case of the hole injection layer and emitting layer because a homogenous film is needed. Conditions for the deposition can be selected from conditions similar to those for the hole injection layer and emitting layer.

Lastly, a cathode is provided thereon to manufacture an organic EL device. The cathode is made of metal and can be formed by vapor deposition, sputtering or the like. Vacuum vapor deposition is preferable in order to protect the underlying organic thin layers from being damaged during manufacture.

For the organic EL device manufacturing described above, it is preferable that the formation from the anode to cathode is continuously carried out with a single vacuuming.

There no particular limitations on the methods for forming layers of an organic EL device of the present invention: Vacuum vapor deposition, spin coating or other known technique can be employed. An organic thin film that contains a compound represented by general formula (1), which is used in an organic EL device of the present invention, can be formed using a known technique, such as vacuum vapor deposition, molecular beam epitaxy (MBE) method, or coating method that uses a solution prepared by dissolving the compound into a solvent. Coating methods include dipping, spin coating, casting, bar coating and roll coating.

The thickness of organic thin layers in the organic EL device of the present invention is not particularly limited. However, generally, it is preferably set to from several nanometers to 1 μm to prevent defects such as pinholes or to improve luminous efficiency.

Where DC voltage is used for light emission, light emission can be observed when 5V to 40V voltage is applied to an organic EL device in which the anode is made positive (+) and the cathode is made negative (−). When voltage is applied while making the anode negative and the cathode positive, no current flows and thus no light emission occurs, and when AC voltage is applied, uniform light emission can be observed only when the anode is made positive and the cathode is made negative. Any desired waveform can be used for the AC voltage.

EXAMPLES

Hereinafter, the present invention will be described in detail with reference to Preparation Examples, Synthesis Examples and Examples.

Structural formulas of Intermediate 1 to 14 are as follows:

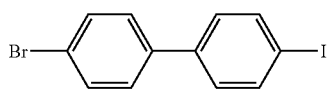

Intermediate 1

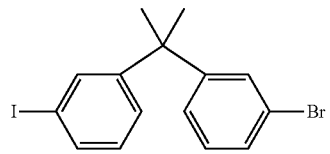

Intermediate 2

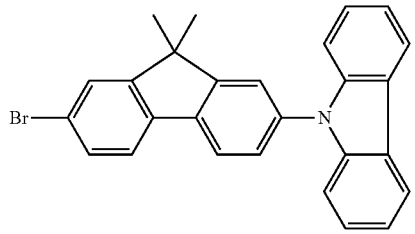

Intermediate 3

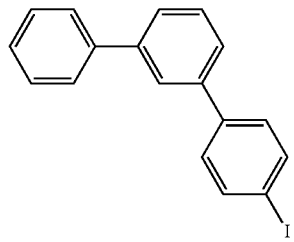

Intermediate 4

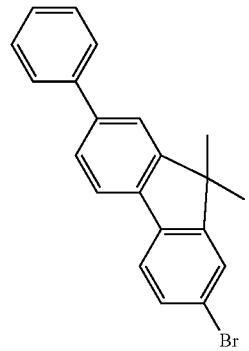

Intermediate 5

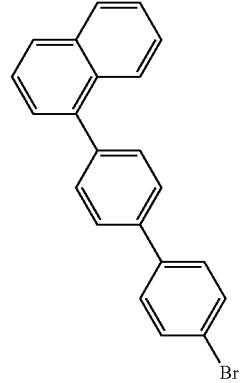

Intermediate 6

Intermediate 7

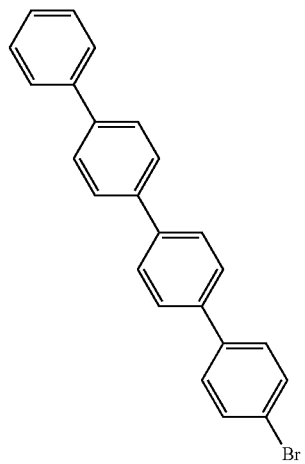

Intermediate 8

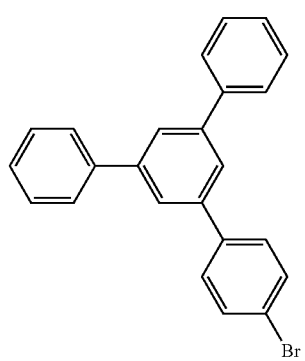

Intermediate 9

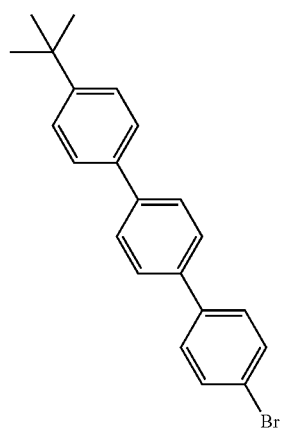

Intermediate 10

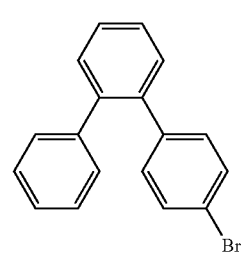

Intermediate 11

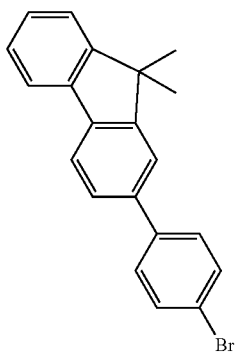

Intermediate 12

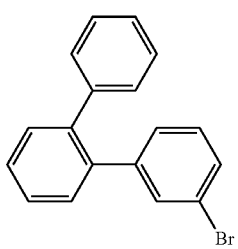

Intermediate 13

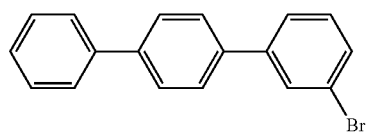

Intermediate 14

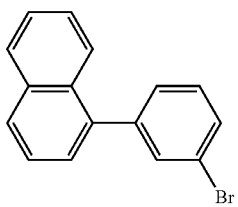

Preparation Example 1

Synthesis of Intermediate 1

In an argon gas stream, a 1,000 ml three-necked flask was charged with 47 g of 4-bromobiphenyl, 23 g of iodine, 9.4 g of periodic acid dihydrate, 42 ml of water, 360 ml of acetic acid, and 11 ml of sulfuric acid. The mixture was stirred at 65° C. for 30 minutes and reaction was allowed to proceed at 90° C. for 6 hours. The product was placed in ice water, filtered off, washed with water, and washed with methanol to give 67 g of white powder. FD-MS analysis identified the powder as Intermediate 1.

Preparation Example 2

Synthesis of Intermediate 2

The same procedure as that of Preparation Example 1 was followed except that 2-bromo-9,9-dimethylfluorene was used instead of 4-bromobiphenyl, yielding 61 g of white powder. FD-MS analysis identified the powder as Intermediate 2.

Preparation Example 3

Synthesis of Intermediate 3

In an argon gas stream, a 500 ml three-necked flask was charged with 45 g of Intermediate 1, 21 g of carbazole, 240 mg of copper(I) iodide, 56 g of tripotassium phosphate, 160 ml of 1,4-dioxane, and 2.5 ml of trans-1,2-cyclohexanediamine, and reaction was allowed to proceed at 130° C. for 24 hours. The product was extracted with toluene, dried over magnesium sulfate, and concentrated in vacuo. The crude product was then purified on a column, recrystallized from toluene, filtered off, and dried to give 33 g of Intermediate 3 in the form of white powder.

Preparation Example 4

Synthesis of Intermediate 4

A three-necked flask was charged with 250 g of m-terphenyl (ALDRICH), 50 g of hydroiodic acid dihydrate, 75 g of iodine, 750 ml of acetic acid, and 25 ml of concentrated sulfuric acid, and reaction was allowed to proceed at 70° C. for 3 hours. The product was poured into 5 L of methanol and the mixture was stirred for 1 hour and filtrated. The obtained crystals were purified by column chromatography, and recrystallized from acetonitrile to give 64 g of 3'-phenyl-4-iodobiphenyl (Intermediate 4) and 17 g of 3-phenyl-5-iodobiphenyl in the form of white powder. FD-MS and H-NMR analysis identified the powder as Intermediate 4.

Preparation Example 5

Synthesis of Intermediate 5

In an argon gas stream, 300 ml of toluene and 150 ml of 2M sodium carbonate aqueous solution were added to a mixture of 39.9 g (100 mmol) of Intermediate 2, 12.4 g (105 mmol) of phenylboronic acid and 2.31 g (2.00 mmol) of tetrakis(triphenylphosphine)palladium(0). The mixture was heated under reflux for 10 hours.

The solution was filtrated immediately after the reaction, and then the aqueous phase was removed. The organic phase was dried over magnesium sulfate and concentrated, and the residue was purified by column chromatography on silica gel to give 28.3 g of white crystals (yield: 81%). FD-MS analysis identified the crystals as Intermediate 5.

Preparation Example 6

Synthesis of Intermediate 6

The same procedure as that of Preparation Example 5 was followed except that Intermediate 1 and 1-naphthylboronic acid were used instead of Intermediate 2 and phenylboronic acid, respectively, yielding 30.2 g of white powder. FD-MS analysis identified the powder as Intermediate 6.

Preparation Example 7

Synthesis of Intermediate 7

The same procedure as that of Preparation Example 5 was followed except that Intermediate 1 and 4-biphenylboronic acid were used instead of Intermediate 2 and phenylboronic acid, respectively, yielding 32.1 g of white powder. FD-MS analysis identified the powder as Intermediate 7.

Preparation Example 8

Synthesis of Intermediate 8

In an argon gas stream, 400 ml of anhydrous THF was added to 29.6 g (100 mmol) of 3-phenyl-5-iodobiphenyl, the by-product obtained in Preparation Example 4. While stirring the mixture at −40° C., 63 ml (100 mmol) of 1.6M n-butyllithium in hexane was added thereto. The reaction solution was stirred for 1 hour while heating it to 0°. The reaction solution was again cooled to −78° C., and 50 ml of trimethyl borate in anhydrous THF, containing 26.0 g (250 mmol) of trimethyl borate, was added dropwise to the reaction solution.

The reaction solution was stirred at room temperature for 5 hours, and 200 ml of 1N hydrochloric acid was added. After 1 hour stirring the aqueous phase was removed, the organic phase was dried over magnesium sulfate, and the solvent was removed by distillation in vacuo. The resultant solid was washed with toluene to give 19.2 g of boronic acid compound, which was identified by FD-MS analysis.

In an argon gas stream, 300 ml of toluene and 150 ml of 2M sodium carbonate aqueous solution were added to a mixture of 28.3 g (100 mmol) of 4-iodobromobenzene, 28.5 g (105 mmol) of the boronic acid compound above and 2.31 g (2.00 mmol) of tetrakis(triphenylphosphine)palladium(0). The mixture was heated under reflux for 10 hours.

The solution was filtrated immediately after the reaction, and then the aqueous phase was removed. The organic phase was dried over magnesium sulfate and concentrated, and the residue was purified by column chromatography on silica gel to give 26.2 g of white powder. FD-MS analysis identified the powder as Intermediate 8.

Preparation Example 9

Synthesis of Intermediate 9

The same procedure as that of Preparation Example 5 was followed except that Intermediate 1 and 4-t-butylphenylboronic acid were used instead of Intermediate 2 and phenylboronic acid, respectively, yielding 32.1 g of white powder. FD-MS analysis identified the powder as Intermediate 9.

Preparation Example 10

Synthesis of Intermediate 10

The same procedure as that of Preparation Example 5 was followed except that 4-bromoiodobenzene and 2-biphenylboronic acid were used instead of Intermediate 2 and phenylboronic acid, respectively, yielding 23.6 g of white powder. FD-MS analysis identified the powder as Intermediate 10.

Preparation Example 11

Synthesis of Intermediate 11

The same procedure as that of Preparation Example 5 was followed except that 4-bromoiodobenzene and 9,9-dimethyl-9H-fluorene-2-boronic acid were used instead of Intermediate 2 and phenylboronic acid, respectively, yielding 28.9 g of white powder. FD-MS analysis identified the powder as Intermediate 11.

Preparation Example 12

Synthesis of Intermediate 12

The same procedure as that of Preparation Example 5 was followed except that 3-bromoiodobenzene and 2-biphenylboronic acid were used instead of Intermediate 2 and phenylboronic acid, respectively, yielding 21.3 g of colorless liquid. FD-MS analysis identified the liquid as Intermediate 12.

Preparation Example 13

Synthesis of Intermediate 13

The same procedure as that of Preparation Example 5 was followed except that 3-bromoiodobenzene and 4-biphenylboronic acid were used instead of Intermediate 2 and phenylboronic acid, respectively, yielding 24.1 g of white powder. FD-MS analysis identified the powder as Intermediate 13.

Preparation Example 14

Synthesis of Intermediate 14

The same procedure as that of Preparation Example 5 was followed except that 3-bromoiodobenzene and naphthalene-2-boronic acid were used instead of Intermediate 2 and phenylboronic acid, respectively, yielding 21.5 g of white powder. FD-MS analysis identified the powder as Intermediate 14.

The structural formulas of Intermediates Am1 to Am16 are as follows:

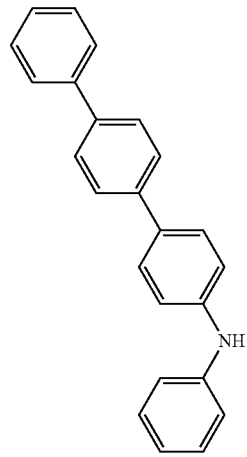

Intermediate Am1

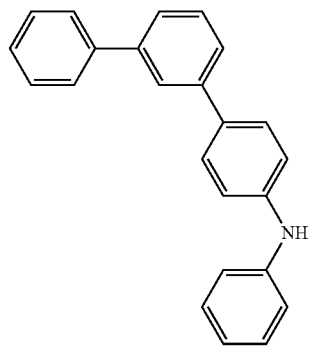

Intermediate Am2

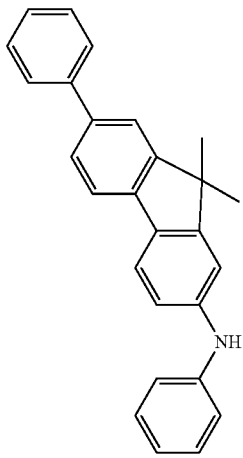

Intermediate Am3

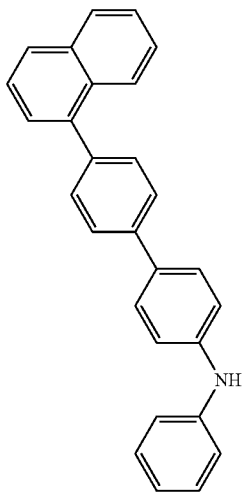

Intermediate Am4

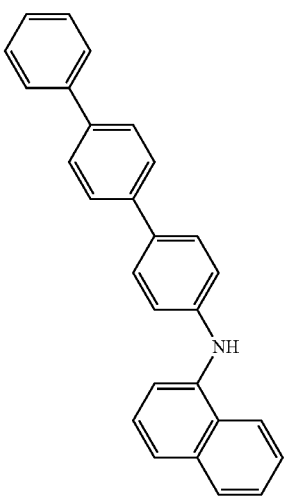

Intermediate Am5

Intermediate Am6
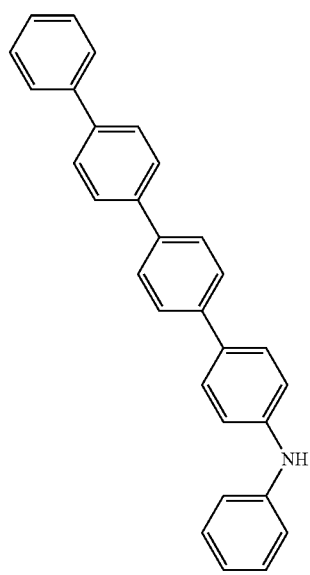
Intermediate Am7
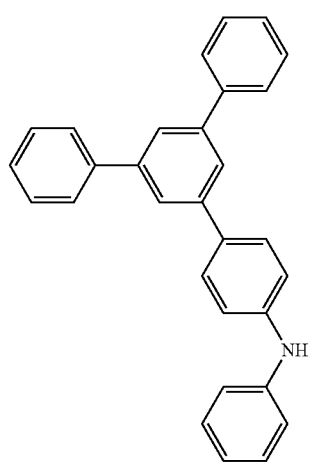
Intermediate Am8
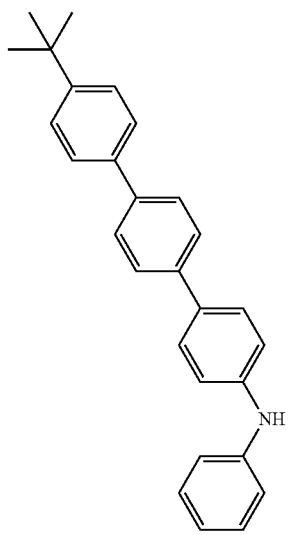
Intermediate Am9
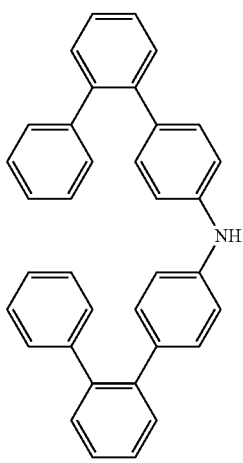
Intermediate Am10
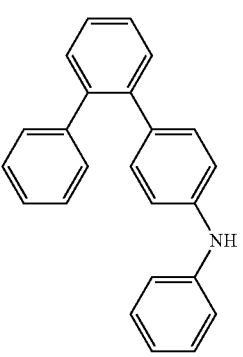
Intermediate Am11
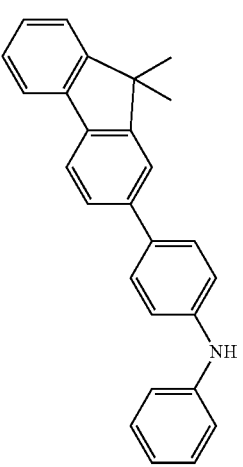

Intermediate Am12

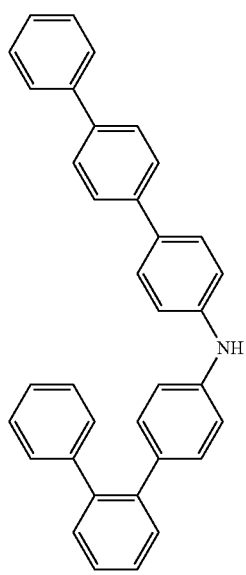

Intermediate Am13

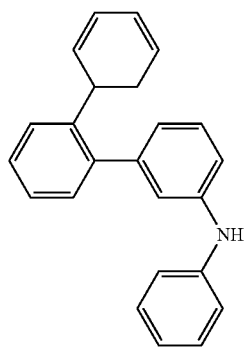

Intermediate Am14

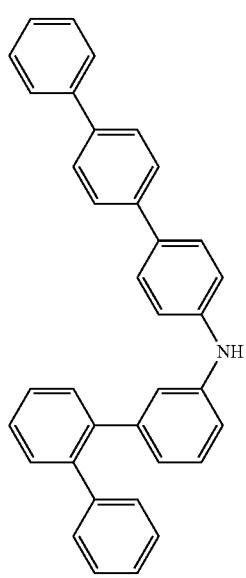

Intermediate Am15

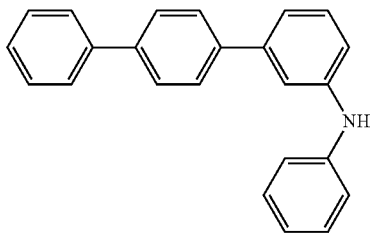

Intermediate Am16

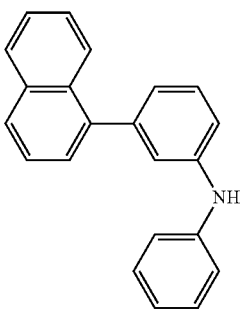

Preparation Example 15

Synthesis of Intermediate Am1

In an argon gas stream, 30.7 g of 4-bromo-p-terphenyl, 9.1 g of aniline, 13.0 g of sodium t-butoxide (Hiroshima Wako Ltd.), 460 mg of tris(dibenzylideneacetone)dipalladium(0) (ALDRICH), 210 mg of tri-t-butylphosphine were added to 500 ml of dry toluene, and reaction was allowed to proceed at 80° C. for 8 hours.

After cooled, 2.5 L of water was added. The mixture was filtrated though celite, and the flow-through was extracted with toluene, dried over magnesium sulfate, and concentrated in vacuo. The crude product was then purified on a column, recrystallized from toluene, filtered off, and dried to give 15.7 g of light yellow powder. FD-MS analysis identified the powder as Intermediate Am1.

Preparation Example 16

Synthesis of Intermediate Am2

The same procedure as that of Preparation Example 15 was followed except that Intermediate 4 was used instead of 4-bromo-p-terphenyl, yielding 16.3 g of white powder. FD-MS analysis identified the powder as Intermediate Am2.

Preparation Example 17

Synthesis of Intermediate Am3

The same procedure as that of Preparation Example 15 was followed except that Intermediate 5 was used instead of 4-bromo-p-terphenyl, yielding 18.1 g of white powder. FD-MS analysis identified the powder as Intermediate Am3.

Preparation Example 18

Synthesis of Intermediate Am4

The same procedure as that of Preparation Example 15 was followed except that Intermediate 6 was used instead of 4-bromo-p-terphenyl, yielding 15.9 g of white powder. FD-MS analysis identified the powder as Intermediate Am4.

Preparation Example 19

Synthesis of Intermediate Am5

The same procedure as that of Preparation Example 15 was followed except that 1-bromonaphthalene and 4-amino-p-terphenyl were used instead of 4-bromo-p-terphenyl and aniline, respectively, yielding 22.4 g of white powder. FD-MS analysis identified the powder as Intermediate Am5.

Preparation Example 20

Synthesis of Intermediate Am6

The same procedure as that of Preparation Example 15 was followed except that Intermediate 7 was used instead of 4-bromo-p-terphenyl, yielding 20.8 g of white powder. FD-MS analysis identified the powder as Intermediate Am6.

Preparation Example 21

Synthesis of Intermediate Am7

The same procedure as that of Preparation Example 15 was followed except that Intermediate 8 was used instead of 4-bromo-p-terphenyl, yielding 22.5 g of white powder. FD-MS analysis identified the powder as Intermediate Am7.

Preparation Example 22

Synthesis of Intermediate Am8

The same procedure as that of Preparation Example 15 was followed except that Intermediate 9 was used instead of 4-bromo-p-terphenyl, yielding 17.4 g of white powder. FD-MS analysis identified the powder as Intermediate Am8.

Preparation Example 23

Synthesis of Intermediate Am9

In an argon gas stream, 750 ml of toluene and 300 ml of 2M sodium carbonate aqueous solution were added to a mixture of 32.7 g (100 mmol) of bis(4-bromophenyl)amine, 41.6 g (210 mmol) of 2-biphenyl boronic acid and 1.15 g (1.00 mmol) of tetrakis(triphenylphosphine)palladium(0). The mixture was heated under reflux for 15 hours.

The solution was filtrated immediately after the reaction, and then the aqueous phase was removed. The organic phase was dried over magnesium sulfate and concentrated, and the residue was purified by column chromatography on silica gel to give 30.3 g of glassy solid. FD-MS analysis identified the solid as Intermediate Am9.

Preparation Example 24

Synthesis of Intermediate Am10

The same procedure as that of Preparation Example 15 was followed except that Intermediate 10 was used instead of 4-bromo-p-terphenyl, yielding 13.2 g of white powder. FD-MS analysis identified the powder as Intermediate Am10.

Preparation Example 25

Synthesis of Intermediate Am11

The same procedure as that of Preparation Example 15 was followed except that Intermediate 11 was used instead of 4-bromo-p-terphenyl, yielding 14.8 g of white powder. FD-MS analysis identified the powder as Intermediate Am11.

Preparation Example 26

Synthesis of Intermediate Am12

The same procedure as that of Preparation Example 15 was followed except that Intermediate 10 and 4-amino-p-terphenyl were used instead of 4-bromo-p-terphenyl and aniline, respectively, yielding 22.5 g of white powder. FD-MS analysis identified the powder as Intermediate Am12.

Preparation Example 27

Synthesis of Intermediate Am13

The same procedure as that of Preparation Example 15 was followed except that Intermediate 12 was used instead of 4-bromo-p-terphenyl, yielding 11.6 g of white powder. FD-MS analysis identified the powder as Intermediate Am13.

Preparation Example 28

Synthesis of Intermediate Am14

The same procedure as that of Preparation Example 15 was followed except that Intermediate 12 and 4-amino-p-terphenyl were used instead of 4-bromo-p-terphenyl and aniline, respectively, yielding 20.9 g of white powder. FD-MS analysis identified the powder as Intermediate Am14.

Preparation Example 29

Synthesis of Intermediate Am15

The same procedure as that of Preparation Example 15 was followed except that Intermediate 13 was used instead of 4-bromo-p-terphenyl, yielding 14.3 g of white powder. FD-MS analysis identified the powder as Intermediate Am15.

Preparation Example 30

Synthesis of Intermediate Am16

The same procedure as that of Preparation Example 15 was followed except that Intermediate 14 was used instead of 4-bromo-p-terphenyl, yielding 10.4 g of white powder. FD-MS analysis identified the powder as Intermediate Am16.

The structural formulas of Compounds H1 to H16 to be made in Synthesis Examples 1 to 6, which are aromatic amine derivatives of the present invention, are as follows:

Compounds H1 to H8
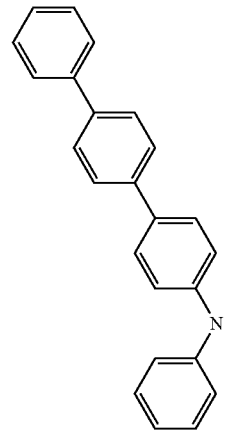
H1
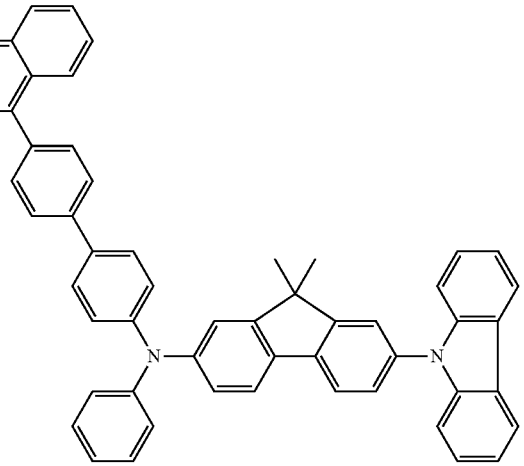
H4
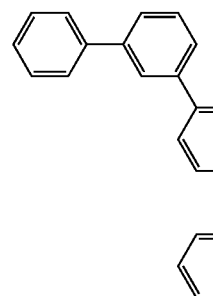
H2
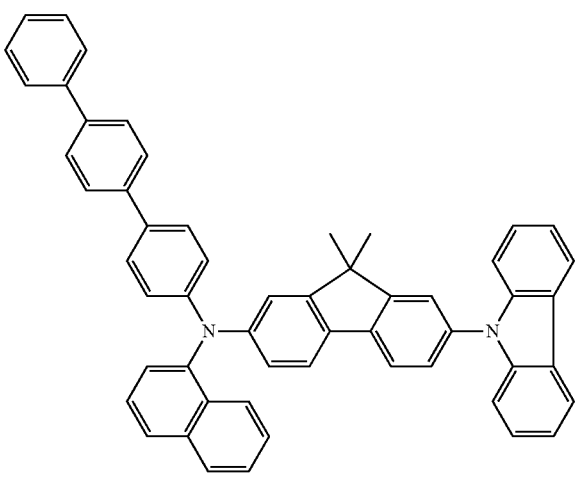
H5
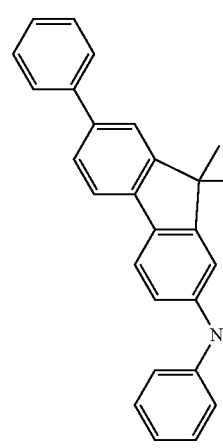
H3
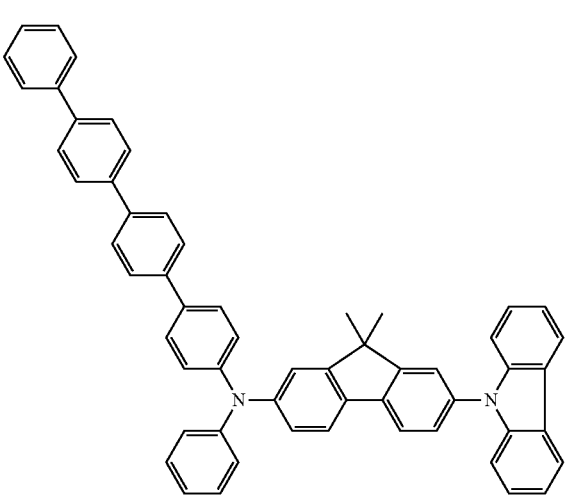
H6

H7
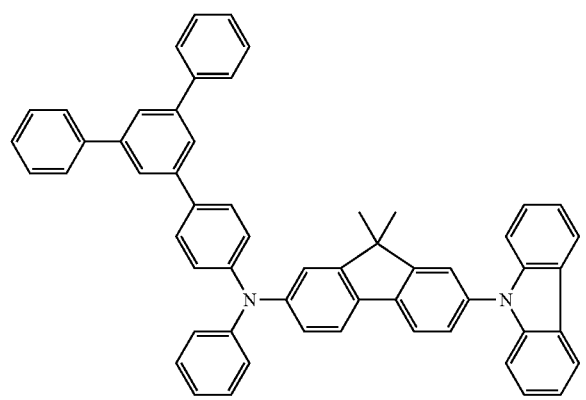
H8
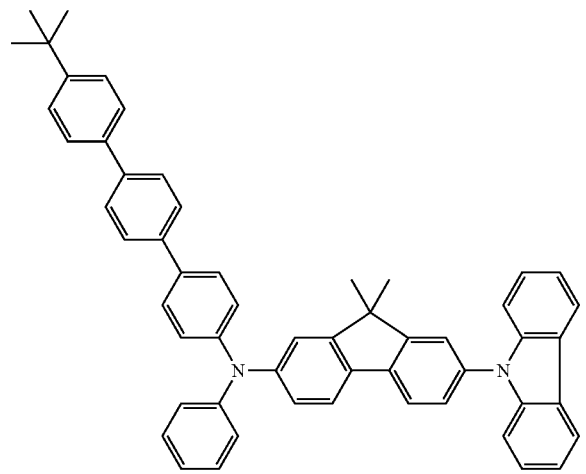
Compounds H9 to H16
H9
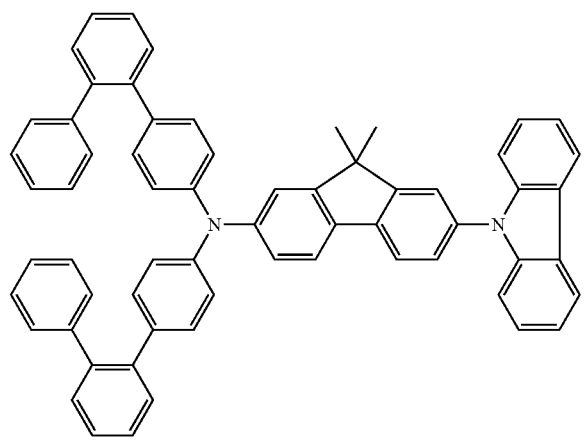
H10
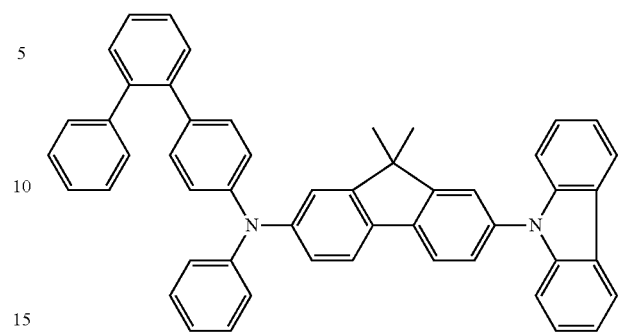
H11
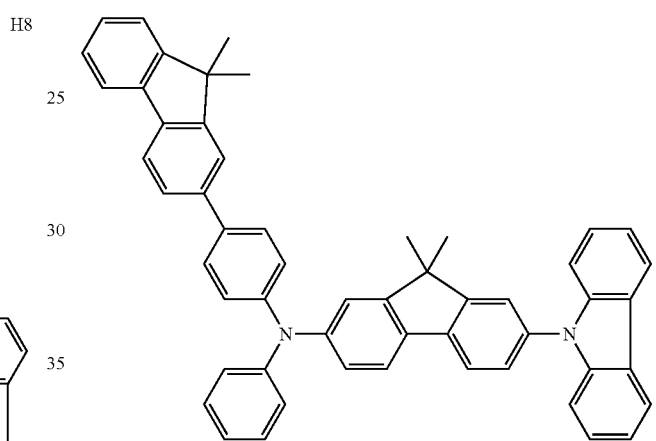
H12
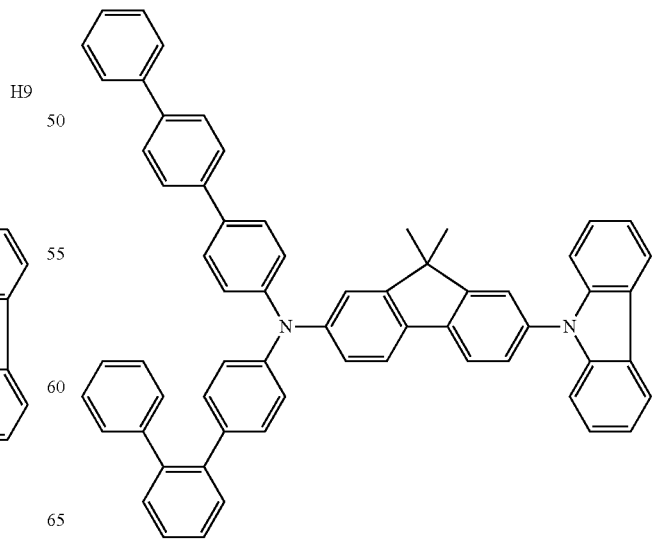

-continued

H13
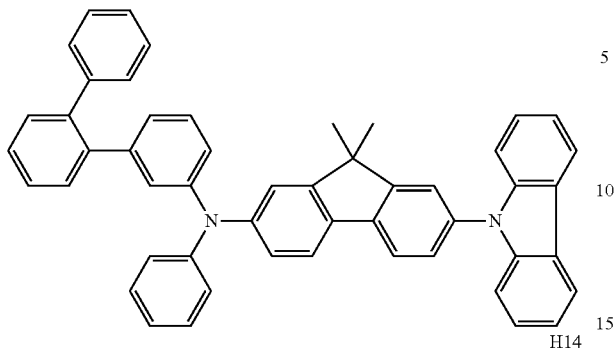
H14

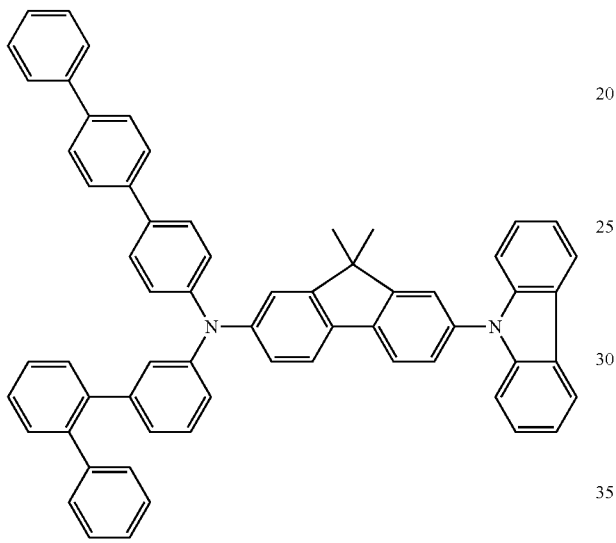
H15

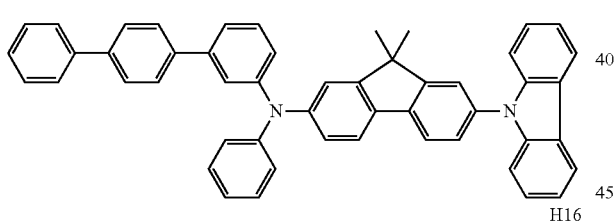
H16

Synthesis Example 1

Synthesis of Compound H1

In an argon gas stream, 8.0 g of Intermediate 3, 6.4 g of Intermediate Am1, 2.6 g of sodium t-butoxide (Hiroshima Wako Ltd.), 92 mg of tris(dibenzylideneacetone)dipalladium (0) (ALDRICH), 42 mg of tri-t-butylphosphine were added to 100 ml of dry toluene, and reaction was allowed to proceed at 80° C. for 8 hours.

After cooled, 500 ml of water was added. The mixture was filtrated though celite, and the flow-through was extracted with toluene, dried over magnesium sulfate, and concentrated in vacuo. The crude product was then purified on a column, recrystallized from toluene, filtered off, and dried to give 7.1 g of light yellow powder. FD-MS analysis identified the powder as Compound H1. Further, the compound was purified by sublimation in vacuo ($2 \times 10^{-4}$ Pa). With single purification, high-purity Compound H1 was obtained which showed no impurity peaks in HPLC analysis.

Synthesis Example 2

Synthesis of Compound H2

The same procedure as that of Synthesis Example 1 was followed except that Intermediate Am2 was used instead of Intermediate Am1, yielding 6.6 g of light yellow powder. FD-MS analysis identified the powder as Compound H2. Further, the compound was purified by sublimation in vacuo ($2 \times 10^{-4}$ Pa). With single purification, high-purity Compound H2 was obtained which showed no impurity peaks in HPLC analysis.

Synthesis Example 3

Synthesis of Compound H3

The same procedure as that of Synthesis Example 1 was followed except that Intermediate Am3 was used instead of Intermediate Am1, yielding 7.31 g of light yellow powder. FD-MS analysis identified the powder as Compound H3. Further, the compound was purified by sublimation in vacuo ($2 \times 10^{-4}$ Pa). With single purification, high-purity Compound H3 was obtained which showed no impurity peaks in HPLC analysis.

Synthesis Example 4

Synthesis of Compound H4

The same procedure as that of Synthesis Example 1 was followed except that Intermediate Am4 was used instead of Intermediate Am1, yielding 7.9 g of light yellow powder. FD-MS analysis identified the powder as Compound H4. Further, the compound was purified by sublimation in vacuo ($2 \times 10^{-4}$ Pa). With single purification, high-purity Compound H4 was obtained which showed no impurity peaks in HPLC analysis.

Synthesis Example 5

Synthesis of Compound H5

The same procedure as that of Synthesis Example 1 was followed except that Intermediate Am5 was used instead of Intermediate Am1, yielding 8.3 g of light yellow powder. FD-MS analysis identified the powder as Compound H5. Further, the compound was purified by sublimation in vacuo ($2 \times 10^{-4}$ Pa). With single purification, high-purity Compound H5 was obtained which showed no impurity peaks in HPLC analysis.

Synthesis Example 6

Synthesis of Compound H6

The same procedure as that of Synthesis Example 1 was followed except that Intermediate Am6 was used instead of Intermediate Am1, yielding 7.9 g of light yellow powder. FD-MS analysis identified the powder as Compound H6. Further, the compound was purified by sublimation in vacuo ($2\times10^{-4}$ Pa). With single purification, high-purity Compound H6 was obtained which showed no impurity peaks in HPLC analysis.

Synthesis Example 7

Synthesis of Compound H7

The same procedure as that of Synthesis Example 1 was followed except that Intermediate Am7 was used instead of Intermediate Am1, yielding 6.5 g of light yellow powder. FD-MS analysis identified the powder as Compound H7. Further, the compound was purified by sublimation in vacuo ($2\times10^{-4}$ Pa). With single purification, high-purity Compound H7 was obtained which showed no impurity peaks in HPLC analysis.

Synthesis Example 8

Synthesis of Compound H8

The same procedure as that of Synthesis Example 1 was followed except that Intermediate Am8 was used instead of Intermediate Am1, yielding 6.2 g of light yellow powder. FD-MS analysis identified the powder as Compound H8. Further, the compound was purified by sublimation in vacuo ($2\times10^{-4}$ Pa). With single purification, high-purity Compound H8 was obtained which showed no impurity peaks in HPLC analysis.

Synthesis Example 9

Synthesis of Compound H9

The same procedure as that of Synthesis Example 1 was followed except that Intermediate Am9 was used instead of Intermediate Am1, yielding 5.9 g of light yellow powder. FD-MS analysis identified the powder as Compound H9. Further, the compound was purified by sublimation in vacuo ($2\times10^{-4}$ Pa). With single purification, high-purity Compound H9 was obtained which showed no impurity peaks in HPLC analysis.

Synthesis Example 10

Synthesis of Compound H10

The same procedure as that of Synthesis Example 1 was followed except that Intermediate Am10 was used instead of Intermediate Am1, yielding 4.6 g of light yellow powder. FD-MS analysis identified the powder as Compound H10. Further, the compound was purified by sublimation in vacuo ($2\times10^{-4}$ Pa). With single purification, high-purity Compound H10 was obtained which showed no impurity peaks in HPLC analysis.

Synthesis Example 11

Synthesis of Compound H11

The same procedure as that of Synthesis Example 1 was followed except that Intermediate Am11 was used instead of Intermediate Am1, yielding 5.4 g of light yellow powder. FD-MS analysis identified the powder as Compound H11. Further, the compound was purified by sublimation in vacuo ($2\times10^{-4}$ Pa). With single purification, high-purity Compound H11 was obtained which showed no impurity peaks in HPLC analysis.

Synthesis Example 12

Synthesis of Compound H12

The same procedure as that of Synthesis Example 1 was followed except that Intermediate Am12 was used instead of Intermediate Am1, yielding 6.7 g of light yellow powder. FD-MS analysis identified the powder as Compound H12. Further, the compound was purified by sublimation in vacuo ($2\times10^{-4}$ Pa). With single purification, high-purity Compound H12 was obtained which showed no impurity peaks in HPLC analysis.

Synthesis Example 13

Synthesis of Compound H13

The same procedure as that of Synthesis Example 1 was followed except that Intermediate Am13 was used instead of Intermediate Am1, yielding 4.8 g of light yellow powder. FD-MS analysis identified the powder as Compound H13. Further, the compound was purified by sublimation in vacuo ($2\times10^{-4}$ Pa). With single purification, high-purity Compound H13 was obtained which showed no impurity peaks in HPLC analysis.

Synthesis Example 14

Synthesis of Compound H14

The same procedure as that of Synthesis Example 1 was followed except that Intermediate Am14 was used instead of Intermediate Am1, yielding 6.2 g of light yellow powder. FD-MS analysis identified the powder as Compound H14. Further, the compound was purified by sublimation in vacuo ($2\times10^{-4}$ Pa). With single purification, high-purity Compound H14 was obtained which showed no impurity peaks in HPLC analysis.

Synthesis Example 15

Synthesis of Compound H15

The same procedure as that of Synthesis Example 1 was followed except that Intermediate Am15 was used instead of Intermediate Am1, yielding 5.8 g of light yellow powder. FD-MS analysis identified the powder as Compound H15. Further, the compound was purified by sublimation in vacuo

Synthesis Example 16

Synthesis of Compound H16

The same procedure as that of Synthesis Example 1 was followed except that Intermediate Am16 was used instead of Intermediate Am1, yielding 4.2 g of light yellow powder. FD-MS analysis identified the powder as Compound H16. Further, the compound was purified by sublimation in vacuo ($2 \times 10^{-4}$ Pa). With single purification, high-purity Compound H16 was obtained which showed no impurity peaks in HPLC analysis.

Comparative Synthesis Example 1

Synthesis of Comparative Compound 4

The same procedure as that of Synthesis Example 1 was followed except that N,N-diphenylamine was used instead of Intermediate Am1, yielding 3.6 g of light yellow powder. FD-MS analysis identified the powder as Comparative Compound 4. Further, the compound was purified by sublimation in vacuo ($2 \times 10^{-4}$ Pa). With single purification, high-purity Comparative Compound 4 in which impurity peaks were completely removed was not obtained.

Comparative Synthesis Example 2

Synthesis of Comparative Compound 5

The same procedure as that of Synthesis Example 1 was followed except that N-(4-methoxyphenyl)-N-phenylamine was used instead of Intermediate Am1, yielding 3.6 g of light yellow powder. FD-MS analysis identified the powder as Comparative Compound 5. Further, the compound was purified by sublimation in vacuo ($2 \times 10^{-4}$ Pa). With single purification, high-purity Comparative Compound 5 in which impurity peaks were completely removed was not obtained.

Example 1

Manufacture of Organic EL Device

A 25 mm×75 mm×1.1 mm glass substrate with ITO transparent electrodes (GEOMATEC Corporation) was washed by sonication in isopropylalcohol for 5 minutes, and washed with UV-ozone for 30 minutes.

After washing and cleaning, the glass substrate with transparent electrode lines was attached to the substrate holder of a vacuum vapor deposition device. The following Compound H232 was then deposited onto the transparent electrode surface of the glass substrate in such a way as to cover the transparent electrodes, forming 60 nm-thick H232 film as a hole injection layer.

On the H232 film was deposited Compound H1 (Synthesis Example 1) to form a 20 nm-thick hole transport layer. Furthermore, the following Compound EM1 was deposited thereon to form a 40 nm-thick emitting layer. At the same time, as light-emitting molecules, the following styryl group-containing amine compound D1 was deposited at 40:2 EM1 to D1 weight ratio.

The following Compound Alq was deposited thereon to a thickness of 10 nm. This layer functions as an electron injection layer. Thereafter, Lithium (Li source: SAES Getters), a reductive dopant, and Alq were simultaneously deposited to form a Alq:Li film (thickness: 10 nm) as an electron injection layer (cathode). On the Alq:Li film, aluminum was deposited to form a metallic cathode. In this way an organic EL device was manufactured.

After storing the organic EL device at 105° C. for 8 hours, its luminous efficiency was measured and light color was observed. Brightness was measured with a spectroradiometer (Minolta CS1000), calculating the luminous efficiency at 10 mA/cm². Moreover, the luminescence half-life was measured at an initial brightness of 5,000 cd/m² and under constant DC drive at room temperature. The results are listed in Table 1.

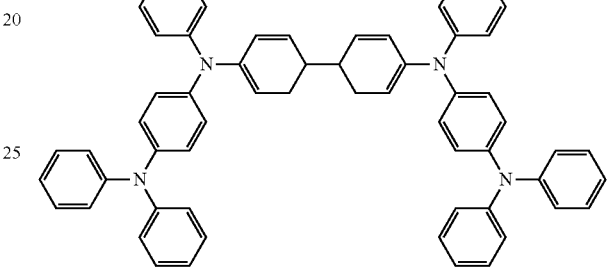

H232

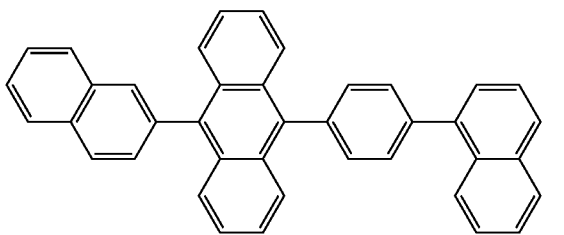

EM1

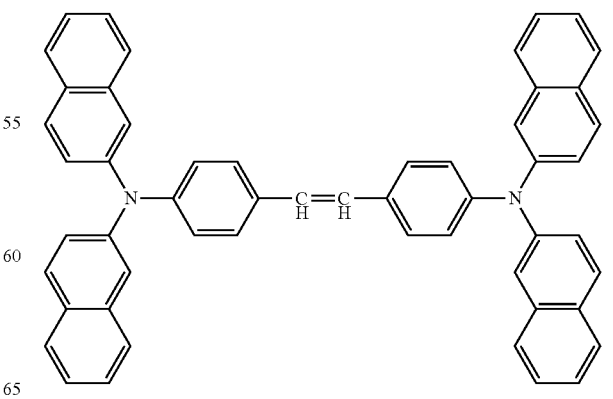

D1

-continued

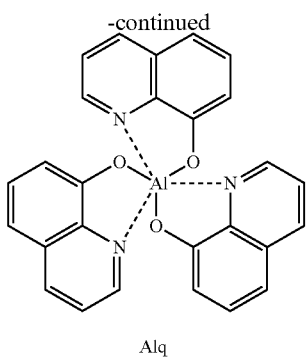

Alq

Examples 2 to 4

Manufacture of Organic EL Device

Organic EL devices were manufactured as in Example 1 except that as hole transport material Compounds H2, H3 and H5 synthesized above were used instead of Compound H1.

After storage at 105° C. for 8 hours, the organic EL devices thus manufactured were measured for their luminous efficiency, light color, and luminescence half-life (initial brightness: 5,000 cd/m², constant DC drive, room temperature) as in Example 1. The results are listed in Table 1.

Example 5

Manufacture of Organic EL Device

An organic EL device was manufactured as in Example 2 except that the following arylamine compound D2 (where "Me" is methyl group) was used instead of styryl group-containing amine compound D1.

After storage at 105° C. for 8 hours, the organic EL device thus manufactured was measured for its luminous efficiency, light color, and luminescence half-life (initial brightness: 5,000 cd/m², constant DC drive, room temperature) as in Example 1. The results are listed in Table 1.

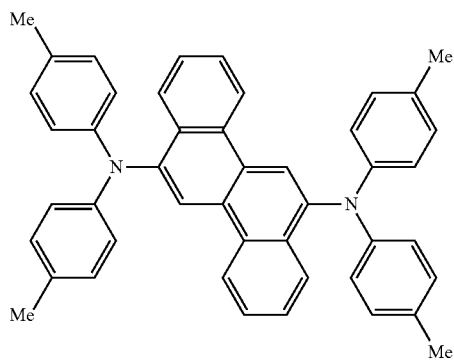

D2

Comparative Examples 1 to 5

Manufacture of Organic EL Device

Organic EL devices were manufactured as in Example 1 except that as hole transport material Comparative Compounds 1 to 5 were used instead of Compound H1.

After storage at 105° C. for 8 hours, the organic EL devices thus manufactured were measured for their luminous efficiency, light color, and luminescence half-life (initial brightness: 5,000 cd/m², constant DC drive, room temperature) as in Example 1. The results are listed in Table 1.

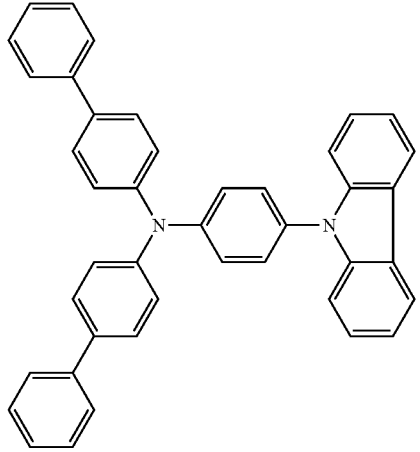

Comparative Compound 1

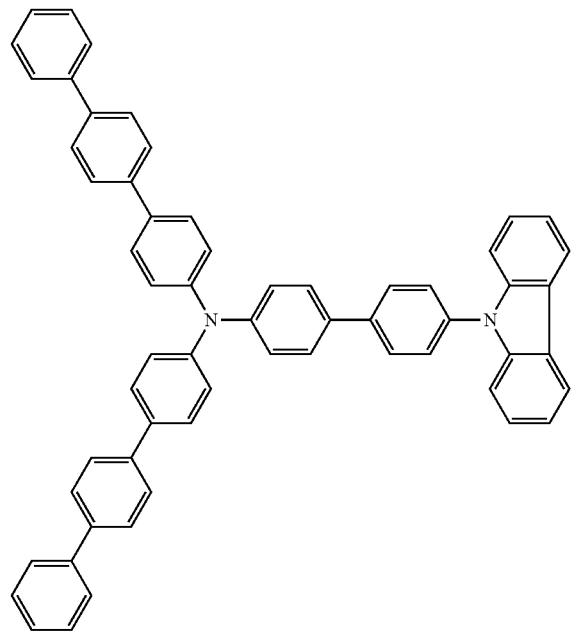

Comparative Compound 2

Comparative Compound 3

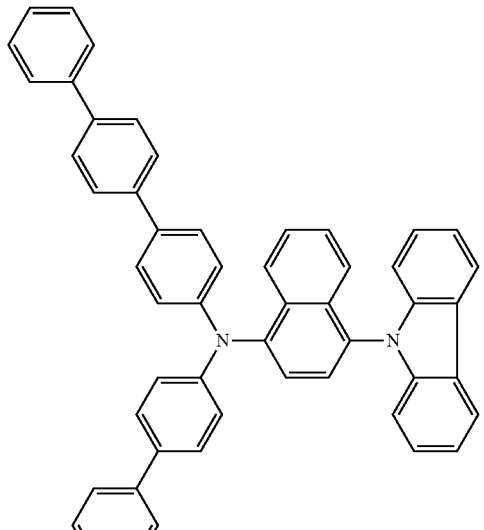

Comparative Compound 4

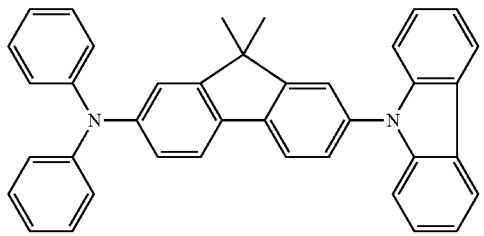

Comparative Compound 5

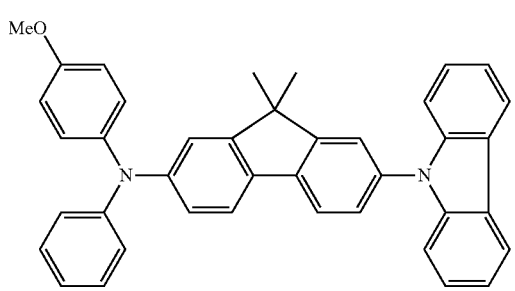

Comparative Example 6

Manufacture of Organic EL Device

An organic EL device was manufactured as in Example 5 except that as hole transport material Comparative Compound 4 was used instead of Compound H1.

After storage at 105° C. for 8 hours, the organic EL device thus manufactured was measured for its luminous efficiency, light color, and luminescence half-life (initial brightness: 5,000 cd/m², constant DC drive, room temperature) as in Example 1. The results are listed in Table 1.

TABLE 1

| Examples | Hole transport material | Luminous efficiency (cd/A) | Light color | Half-life (h) |
|---|---|---|---|---|
| Ex. 1 | H1 | 6.3 | Blue | 430 |
| Ex. 2 | H2 | 6.2 | Blue | 470 |
| Ex. 3 | H3 | 6.4 | Blue | 440 |
| Ex. 4 | H5 | 6.3 | Blue | 390 |
| Ex. 5 | H2 | 6.3 | Blue | 460 |
| Comp. Ex. 1 | Comparative Compound 1 | 4.2 | Blue | 130 |
| Comp. Ex. 2 | Comparative Compound 2 | 5.4 | Blue | 240 |
| Comp. Ex. 3 | Comparative Compound 3 | 5.6 | Blue | 190 |
| Comp. Ex. 4 | Comparative Compound 4 | 3.9 | Blue | 160 |
| Comp. Ex. 5 | Comparative Compound 5 | 3.1 | Blue | 90 |
| Comp. Ex. 6 | Comparative Compound 4 | 4.0 | Blue | 160 |

Example 6

Manufacture of Organic EL Device

An organic EL device was manufactured as in Example 1 except that a 10 nm-thick layer of the following acceptor compound was deposited between the anode and H232 layer, and that the thickness of the H232 layer was changed to 50 nm.

After storage at 105° C. for 8 hours, the organic EL device thus manufactured was measured for its luminous efficiency, light color, and luminescence half-life (initial brightness: 5,000 cd/m², constant DC drive, room temperature) as in Example 1. Luminous efficiency was 5.4 cd/A, light color was blue, and half-life was 410 hours.

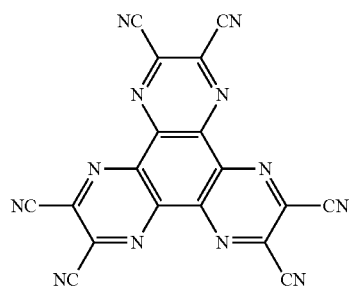

Acceptor Compound

Comparative Example 7

Manufacture of Organic EL Device

An organic EL device was manufactured as in Example 6 except that as hole transport material Comparative Compound 4 was used instead of Compound H1.

After storage at 105° C. for 8 hours, the organic EL device thus manufactured was measured for its luminous efficiency, light color, and luminescence half-life (initial brightness: 5,000 cd/m², constant DC drive, room temperature) as in Example 1. Luminous efficiency was 3.5 cd/A, light color was blue, and half-life was 110 hours.

Industrial Applicability

Aromatic amine derivatives of the present invention can realize a long-life organic EL device having high luminous efficiency even after high temperature storage.

The invention claimed is:

1. An aromatic amine derivative represented by the following general formula (1):

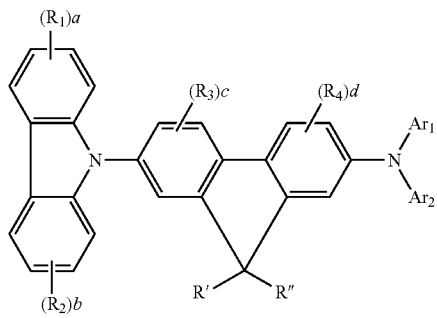

(1)

where $R_1$ to $R_4$ represent a straight or branched $C_{1-10}$ alkyl group, $C_{3-10}$ cycloalkyl group, $C_{1-10}$ alkoxy group, $C_{3-10}$ trialkylsilyl group, $C_{18-30}$ triarylsilyl group, $C_{8-15}$ alkylarylsilyl group, or aryl group having 6 to 14 nuclear carbon atoms;

a and b each independently represent an integer of 0 to 4;

c and d each independently represent an integer of 0 to 3;

adjacent groups of $R_1(s)$, $R_2(s)$, $R_3(s)$ and $R_4(s)$ may be joined together to form a saturated or unsaturated ring, provided that $R_3$ and $R_4$ do not join together to form an aromatic ring;

R' and R" represent a straight or branched $C_{1-12}$ alkyl group or $C_{3-10}$ cycloalkyl group;

$Ar_1$ is represented by the following general formula (2);

$Ar_2$ is represented by the following general formula (3), and $Ar_1$ and $Ar_2$ are different groups,

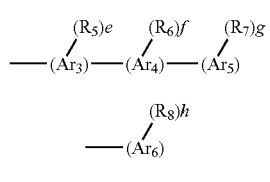

(2)

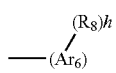

(3)

where $Ar_3$ to $Ar_6$ each independently represent an arylene group having 6 to 14 nuclear carbon atoms;

$R_5$ to $R_7$ represent a hydrogen atom, straight or branched $C_{1-10}$ alkyl group, $C_{3-10}$ cycloalkyl group, $C_{1-10}$ alkoxy group, $C_{3-10}$ trialkylsilyl group, $C_{18-30}$ triarylsilyl group, $C_{8-15}$ alkylarylsilyl group, aryl group having 6 to 14 nuclear carbon atoms, or biphenyl group;

$R_8$ represents a hydrogen atom;

e and f each independently represent an integer of 1 to 4;

g and h each independently represent an integer of 1 to 5;

when e, f, g or h represents an integer of 2 or larger, $R_5$s, $R_6$s, or $R_7$s may be the same or different;

adjacent groups of $R_5(s)$, $R_6(s)$, and $R_7(s)$ may be joined together to form a saturated ring.

2. The aromatic amine derivative according to claim 1, wherein $Ar_1$ is represented by the following general formula (4), and $Ar_2$ is represented by the following general formula (5):

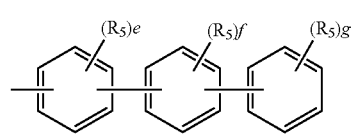

(4)

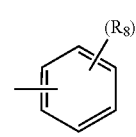

(5)

where $R_5$ to $R_8$, and e, f, g and h are defined the same as those in general formulas (2) and (3).

3. The aromatic amine derivative according to claim 1, wherein $Ar_1$ is represented by the following general formula (6) or (7), and $Ar_2$ is represented by the following general formula (5):

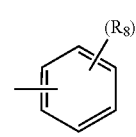

(5)

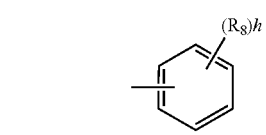

(6)

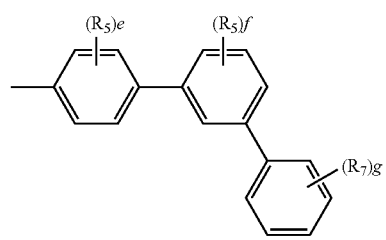

(7)

where $R_5$ to $R_8$, and e, f, g and h are defined the same as those in general formulas (2) and (3).

4. The aromatic amine derivative according to claim 3, wherein $R_5$ to $R_7$ in general formula (6) or (7) are hydrogen atom.

5. The aromatic amine derivative according to any one of claims 1, 2, 3 and 4, wherein the aromatic amine derivative is a material for an organic electroluminescent device.

6. The aromatic amine derivative according to any one of claims 1, 2, 3 and 4, wherein the aromatic amine derivative is a hole transport material for an organic electroluminescent device.

7. An organic electroluminescent device comprising:
a cathode;
an anode; and
one or more organic thin layers interposed between the anode and cathode, the organic thin layers including at least an emitting layer,
wherein at least one of the organic thin layers contains the aromatic amine derivative according to claim 1 either alone or as a component of a mixture.

8. An organic electroluminescent device comprising:
a cathode;
an anode; and
one or more organic thin layers interposed between the anode and cathode, the organic thin layers including at least an emitting layer,
wherein the organic thin layers include a hole transport layer, and the hole transport layer contains the aromatic amine derivative according to claim 1 either alone or as a component of a mixture.

9. An organic electroluminescent device comprising:
a cathode;
an anode; and
one or more organic thin layers interposed between the anode and cathode, the organic thin layers including at least an emitting layer,
wherein the organic thin layers include a plurality of hole transport layers, and one of the hole transport layers which directly contacts the emitting layer contains the aromatic amine derivative according to claim 1, either alone or as a component of a mixture.

10. An organic electroluminescent device comprising:
a cathode;
an anode; and
one or more organic thin layers interposed between the anode and cathode, the organic thin layers including at least an emitting layer,
wherein the organic thin layers include a hole injection layer, and the hole injection layer contains the aromatic amine derivative according to claim 1 either alone or as a component of a mixture.

11. The organic electroluminescent device according to any one of claims 7 to 10, wherein the emitting layer contains a styrylamine compound and/or an arylamine compound.

12. The organic electroluminescent device according to any one of claims 7 to 10, wherein the organic thin layers include a plurality of hole injection layers or hole transport layers, and at least one layer selected from the plurality of hole injection layers and hole transport layers contains an acceptor material.

13. The organic electroluminescent device according to any one of claims 7 to 10, wherein the organic electroluminescent device emits blue light.

14. The aromatic amine derivative according to any one of claims 1, 2, and 3, wherein $R_5$ to $R_7$ represent a hydrogen atom, straight or branched $C_{1-10}$ alkyl group, $C_{3-10}$ trialkylsilyl group, $C_{18-30}$ triarylsilyl group, or aryl group having 6 to 14 nuclear carbon atoms.

15. The aromatic amine derivative according to claim 1, wherein each of $Ar_3$ to $Ar_5$ represents an arylene group selected from the group consisting of the residual divalent groups of benzene, naphthalene, anthracene, phenanthrene, toluene, p-t-butylbenzene, p-(2-phenylpropyl)benzene, 3-methylnaphthalene, and 4-methylnaphthalene.

* * * * *